(12) United States Patent
Maisano et al.

(10) Patent No.: US 8,808,368 B2
(45) Date of Patent: *Aug. 19, 2014

(54) IMPLANTATION OF REPAIR CHORDS IN THE HEART

(75) Inventors: Francesco Maisano, Milan (IT); Eran Miller, Moshav Beit Elazari (IL); Oz Cabiri, Macabim-Reut (IL); Yaron Herman, Givat Ada (IL); Yoseph Weitzman, Tel Aviv (IL); Yossi Gross, Moshav Mazor (IL)

(73) Assignee: Valtech Cardio, Ltd., Or Yehuda (IL)

( * ) Notice: Subject to any disclaimer, the term of this patent is extended or adjusted under 35 U.S.C. 154(b) by 336 days.

This patent is subject to a terminal disclaimer.

(21) Appl. No.: 12/548,991

(22) Filed: Aug. 27, 2009

(65) Prior Publication Data

US 2010/0161042 A1    Jun. 24, 2010

Related U.S. Application Data

(63) Continuation-in-part of application No. 12/435,291, filed on May 4, 2009, and a continuation-in-part of application No. 12/341,960, filed on Dec. 22, 2008.

(51) Int. Cl.
| | |
|---|---|
| A61F 2/24 | (2006.01) |
| A61B 17/04 | (2006.01) |
| A61B 17/00 | (2006.01) |
| A61B 17/122 | (2006.01) |

(52) U.S. Cl.
CPC ....... *A61F 2/2466* (2013.01); *A61B 2017/0496* (2013.01); *A61B 17/0401* (2013.01); *A61F 2250/0007* (2013.01); *A61F 2/2457* (2013.01); *A61B 2017/0441* (2013.01); *A61B 2017/0406* (2013.01); *A61B 2017/00243* (2013.01); *A61B 2017/0464* (2013.01); *A61B 2017/0414* (2013.01); *A61B 17/122* (2013.01); *A61B 2017/0409* (2013.01); *A61F 2/2487* (2013.01)
USPC ..................................................... 623/2.11

(58) Field of Classification Search
USPC .............. 623/2.11, 23.72; 606/139–150, 151, 606/213, 232
See application file for complete search history.

(56) References Cited

U.S. PATENT DOCUMENTS

| | | | |
|---|---|---|---|
| 4,602,911 | A | 7/1986 | Ahmadi et al. |
| 4,625,727 | A | 12/1986 | Leiboff |

(Continued)

FOREIGN PATENT DOCUMENTS

| | | |
|---|---|---|
| WO | 92/05093 | 4/1992 |
| WO | WO 01/26586 | 4/2001 |

(Continued)

OTHER PUBLICATIONS

O'Reilly S et al., "Heart valve surgery pushes the envelope," Medtech Insight 8(3):73, 99-108 (2006).

(Continued)

*Primary Examiner* — Melanie Tyson
(74) *Attorney, Agent, or Firm* — Kilpatrick Townsend & Stockton LLP

(57) ABSTRACT

A method is provided, including positioning, at an intraventricular site of a ventricle of a patient, a spool coupled to a first end portion of a longitudinal member and coupling a second end portion of the longitudinal member to a portion of tissue facing a lumen of the ventricle. Other embodiments are also described.

34 Claims, 54 Drawing Sheets

(56) References Cited

U.S. PATENT DOCUMENTS

| | | |
|---|---|---|
| 4,778,468 A | 10/1988 | Hunt et al. |
| 4,917,698 A | 4/1990 | Carpenter et al. |
| 5,061,277 A | 10/1991 | Carpentier et al. |
| 5,104,407 A | 4/1992 | Lam et al. |
| 5,108,420 A | 4/1992 | Marks |
| 5,306,296 A | 4/1994 | Wright et al. |
| 5,450,860 A | 9/1995 | O'Connor |
| 5,477,856 A | 12/1995 | Lundquist |
| 5,669,919 A | 9/1997 | Sanders et al. |
| 5,674,279 A | 10/1997 | Wright et al. |
| 5,843,120 A | 12/1998 | Israel et al. |
| 5,876,373 A | 3/1999 | Giba et al. |
| 5,961,440 A | 10/1999 | Schweich et al. |
| 5,961,539 A | 10/1999 | Northrup, III et al. |
| 6,045,497 A | 4/2000 | Schweich et al. |
| 6,050,936 A | 4/2000 | Schweich et al. |
| 6,059,715 A | 5/2000 | Schweich et al. |
| 6,165,119 A | 12/2000 | Schweich et al. |
| 6,251,092 B1 | 6/2001 | Qin et al. |
| 6,319,281 B1 | 11/2001 | Patel |
| 6,332,893 B1 | 12/2001 | Mortier et al. |
| 6,406,420 B1 | 6/2002 | McCarthy et al. |
| 6,451,054 B1 | 9/2002 | Stevens |
| 6,524,338 B1 | 2/2003 | Gundry |
| 6,537,314 B2 | 3/2003 | Langberg et al. |
| 6,564,805 B2 | 5/2003 | Garrison et al. |
| 6,569,198 B1 | 5/2003 | Wilson et al. |
| 6,589,160 B2 | 7/2003 | Schweich et al. |
| 6,602,288 B1 | 8/2003 | Cosgrove |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,629,921 B1 | 10/2003 | Schweich et al. |
| 6,651,671 B1 | 11/2003 | Donlon et al. |
| 6,682,558 B2 | 1/2004 | Tu et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,711,444 B2 | 3/2004 | Koblish |
| 6,718,985 B2 | 4/2004 | Hlavka et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,510 B2 | 7/2004 | Vidlund et al. |
| 6,786,924 B2 | 9/2004 | Ryan et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,482 B2 | 6/2005 | McCarthy et al. |
| 6,986,775 B2 | 1/2006 | Morales et al. |
| 6,989,028 B2 | 1/2006 | Lashinski et al. |
| 7,004,176 B2 | 2/2006 | Lau |
| 7,011,669 B2 | 3/2006 | Kimblad |
| 7,011,682 B2 | 3/2006 | Lashinski et al. |
| 7,037,334 B1 | 5/2006 | Hlavka et al. |
| 7,101,395 B2 | 9/2006 | Tremulis |
| 7,112,207 B2 | 9/2006 | Allen et al. |
| 7,125,421 B2 | 10/2006 | Tremulis et al. |
| 7,159,593 B2 | 1/2007 | McCarthy |
| 7,169,187 B2 | 1/2007 | Datta et al. |
| 7,175,660 B2 | 2/2007 | Cartledge et al. |
| 7,186,262 B2 | 3/2007 | Saadat |
| 7,189,199 B2 | 3/2007 | McCarthy et al. |
| 7,226,467 B2 | 6/2007 | Lucatero et al. |
| 7,238,191 B2 | 7/2007 | Bachmann |
| 7,294,148 B2 | 11/2007 | McCarthy |
| 7,297,150 B2 | 11/2007 | Cartledge et al. |
| 7,311,728 B2 | 12/2007 | Solem et al. |
| 7,316,710 B1 | 1/2008 | Cheng et al. |
| 7,329,280 B2 | 2/2008 | Bolling et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,452,376 B2 | 11/2008 | Lim et al. |
| 7,455,690 B2 | 11/2008 | Cartledge et al. |
| 7,507,252 B2 | 3/2009 | Lashinski et al. |
| 7,530,995 B2 | 5/2009 | Quijano |
| 7,549,983 B2 | 6/2009 | Roue et al. |
| 7,563,267 B2 | 7/2009 | Goldfarb et al. |
| 7,563,273 B2 | 7/2009 | Goldfarb et al. |
| 7,588,582 B2 | 9/2009 | Starksen et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,871,433 B2 | 1/2011 | Lattouf |
| 7,927,370 B2 | 4/2011 | Webler |
| 7,993,368 B2 | 8/2011 | Gambale et al. |
| 2002/0087048 A1 | 7/2002 | Brock et al. |
| 2002/0103532 A1 | 8/2002 | Langberg et al. |
| 2002/0173841 A1 | 11/2002 | Ortiz et al. |
| 2002/0177904 A1 | 11/2002 | Huxel et al. |
| 2003/0050693 A1 | 3/2003 | Quijano et al. |
| 2003/0105519 A1 | 6/2003 | Fasol et al. |
| 2003/0167062 A1 | 9/2003 | Gambale et al. |
| 2003/0204195 A1 | 10/2003 | Keane et al. |
| 2003/0233142 A1 | 12/2003 | Morales et al. |
| 2004/0024451 A1 | 2/2004 | Johnson et al. |
| 2004/0122514 A1 | 6/2004 | Forgarty et al. |
| 2004/0148021 A1 | 7/2004 | Cartledge et al. |
| 2004/0172046 A1* | 9/2004 | Hlavka et al. ................ 606/142 |
| 2004/0176788 A1 | 9/2004 | Opolski |
| 2004/0181287 A1 | 9/2004 | Gellman |
| 2004/0193191 A1 | 9/2004 | Starksen |
| 2004/0236419 A1 | 11/2004 | Milo |
| 2005/0004668 A1 | 1/2005 | Aklog et al. |
| 2005/0016560 A1 | 1/2005 | Voughlohn |
| 2005/0055087 A1 | 3/2005 | Starksen |
| 2005/0090827 A1 | 4/2005 | Gedebou |
| 2005/0125002 A1 | 6/2005 | Baran et al. |
| 2005/0171601 A1 | 8/2005 | Cosgrove et al. |
| 2005/0177228 A1 | 8/2005 | Solem et al. |
| 2005/0203606 A1 | 9/2005 | VanCamp |
| 2005/0216039 A1 | 9/2005 | Lederman |
| 2005/0288781 A1 | 12/2005 | Moaddeb et al. |
| 2006/0025787 A1 | 2/2006 | Morales et al. |
| 2006/0069429 A1 | 3/2006 | Spence et al. |
| 2006/0129166 A1 | 6/2006 | Lavelle |
| 2006/0149280 A1 | 7/2006 | Harvie et al. |
| 2006/0161265 A1 | 7/2006 | Levine et al. |
| 2006/0241656 A1 | 10/2006 | Starksen et al. |
| 2006/0241748 A1 | 10/2006 | Lee et al. |
| 2006/0282161 A1 | 12/2006 | Huyn et al. |
| 2006/0287716 A1 | 12/2006 | Banbury et al. |
| 2007/0016287 A1 | 1/2007 | Cartledge et al. |
| 2007/0027536 A1 | 2/2007 | Mihaljevic et al. |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0080188 A1 | 4/2007 | Spence et al. |
| 2007/0083168 A1 | 4/2007 | Whiting et al. |
| 2007/0112422 A1 | 5/2007 | Dehdashtian |
| 2007/0118151 A1* | 5/2007 | Davidson ................ 606/144 |
| 2007/0118154 A1 | 5/2007 | Crabtree |
| 2007/0118213 A1* | 5/2007 | Loulmet ................ 623/2.1 |
| 2007/0162111 A1 | 7/2007 | Fukamachi et al. |
| 2007/0198082 A1 | 8/2007 | Kapadia et al. |
| 2007/0219558 A1 | 9/2007 | Deutsch |
| 2007/0239208 A1 | 10/2007 | Crawford |

(56) References Cited

U.S. PATENT DOCUMENTS

| | | |
|---|---|---|
| 2007/0250160 A1 | 10/2007 | Rafiee |
| 2007/0255400 A1 | 11/2007 | Parravicini et al. |
| 2007/0282375 A1 | 12/2007 | Hindrichs et al. |
| 2008/0004697 A1 | 1/2008 | Lichtenstein et al. |
| 2008/0035160 A1 | 2/2008 | Wodson et al. |
| 2008/0086203 A1 | 4/2008 | Roberts |
| 2008/0091257 A1 | 4/2008 | Andreas et al. |
| 2008/0195126 A1 | 8/2008 | Solem |
| 2008/0208265 A1 | 8/2008 | Frazier et al. |
| 2008/0262609 A1 | 10/2008 | Gross et al. |
| 2008/0288044 A1 | 11/2008 | Osborne |
| 2009/0043153 A1* | 2/2009 | Zollinger et al. ............. 600/37 |
| 2009/0088837 A1 | 4/2009 | Gillinov |
| 2009/0171439 A1 | 7/2009 | Nissl |
| 2009/0177266 A1 | 7/2009 | Powell et al. |
| 2009/0326648 A1 | 12/2009 | Machold et al. |
| 2010/0023117 A1 | 1/2010 | Yoganathan |
| 2010/0023118 A1 | 1/2010 | Medlock |
| 2010/0076499 A1 | 3/2010 | McNamara et al. |
| 2010/0130992 A1 | 5/2010 | Machold et al. |
| 2010/0161041 A1 | 6/2010 | Maisano et al. |
| 2010/0161047 A1 | 6/2010 | Cabiri |
| 2010/0174358 A1 | 7/2010 | Rabkin et al. |
| 2010/0179574 A1 | 7/2010 | Longoria et al. |
| 2010/0234935 A1 | 9/2010 | Bashiri et al. |
| 2010/0280603 A1 | 11/2010 | Maisano |
| 2010/0324598 A1 | 12/2010 | Anderson |
| 2011/0029066 A1 | 2/2011 | Gilad |
| 2011/0082538 A1 | 4/2011 | Dahlgren et al. |
| 2011/0093002 A1 | 4/2011 | Rucker et al. |
| 2011/0106245 A1 | 5/2011 | Miller et al. |
| 2011/0184510 A1 | 7/2011 | Maisano et al. |
| 2011/0190879 A1 | 8/2011 | Bobo et al. |
| 2011/0282361 A1 | 11/2011 | Miller |
| 2011/0288635 A1 | 11/2011 | Miller |

FOREIGN PATENT DOCUMENTS

| | | |
|---|---|---|
| WO | WO 02/085251 | 10/2002 |
| WO | WO 02/085252 | 10/2002 |
| WO | 2005/021063 | 3/2005 |
| WO | WO 2006/097931 | 3/2006 |
| WO | WO 2006/116558 | 11/2006 |
| WO | WO 2007/136783 | 11/2007 |
| WO | WO 2008/068756 | 6/2008 |
| WO | 2010/073246 | 7/2010 |
| WO | WO 2010/073246 | 7/2010 |
| WO | 2011/089601 | 7/2011 |

OTHER PUBLICATIONS

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Swain CP et al., "An endoscopically deliverable tissue-transfixing device for securing biosensors in the gastrointestinal tract," Gastrointestinal Endoscopy 40(6):730-734 (1994).

Odell JA et al., "Early Results of a Simplified Method of Mitral Valve Annuloplasty," Circulation 92:150-154 (1995).

An International Search Report dated Sep. 8, 2009, which issued during the prosecution of Applicant's PCT/IL09/00593.

U.S. Appl. No. 60/873,075, filed Dec. 5, 2006.

U.S. Appl. No. 60/902,146, filed Feb. 16, 2007.

U.S. Appl. No. 61/001,013, filed Oct. 29, 2007.

U.S. Appl. No. 61/132,295, filed Jun. 16, 2008.

"Two dimensional real-time ultrasonic imaging of the heart and great vessels", Mayo Clin Proc. vol. 53:271-303, 1978.

An International Search Report dated Jun. 10, 2010, which issued during the prosecution of Applicant's PCT/IL09/01209.

An Office Action dated Apr. 6, 2010, which issued during the prosecution of Applicant's U.S. Appl. No. 12/484,512.

An International Search Report and a Written Opinion, both dated Aug. 17, 2010, which issued during the prosecution of Applicant's PCT/IL10/00357.

An Office Action dated Aug. 4, 2010, which issued during the prosecution of Applicant's U.S. Appl. No. 12/341,960.

Office Action, U.S. Appl. No. 12/795,026, dated May 10, 2012.

Amendment and Extension, U.S. Appl. No. 12/563,952, dated Apr. 11, 2012.

Interview Summary, U.S. Appl. No. 12/563,952, dated Apr. 4, 2012.

Office Action, U.S. Appl. No. 12/563,952, dated Dec. 29, 2011.

An Office Action dated Nov. 14, 2011, which issued during the prosecution of U.S. Appl. No. 12/608,316.

An International Search Report dated Aug. 17, 2010, which issued during the prosecution of Applicant's PCT/IL2010/000357.

An International Preliminary Report on Patentability dated Nov. 9, 2011, which issued during the prosecution of Applicant's PCT/IL2010/000357.

An Office Action dated Jan. 23, 2012, which issued during the prosecution of U.S. Appl. No. 12/692,061.

An International Search Report dated May 19, 2011, which issued during the prosecution of Applicant's PCT/IL2011/00064.

An International Search Report dated Mar. 30, 2011, which issued during the prosecution of Applicant's PCT/IL2010/001024.

International Search Report and Written Opinion of PCT/IL2013/50992, mailed Mar. 21, 2014, 21 pages.

European Search Report of EP 11786226 mailed on Jan. 28, 2014, 6 pages.

European Search Report of EP 10772090.6 mailed on Jan. 24, 2014, 6 pages.

Notice of Allowance dated Nov. 19, 2013, which issued during the prosecution of U.S. Appl. No. 12/795,192.

An Office Action dated Dec. 16, 2013, which issued during the prosecution of U.S. Appl. No. 13/666,262.

An Office Action dated Dec. 27, 2013, which issued during the prosecution of U.S. Appl. No. 12/785,717.

* cited by examiner

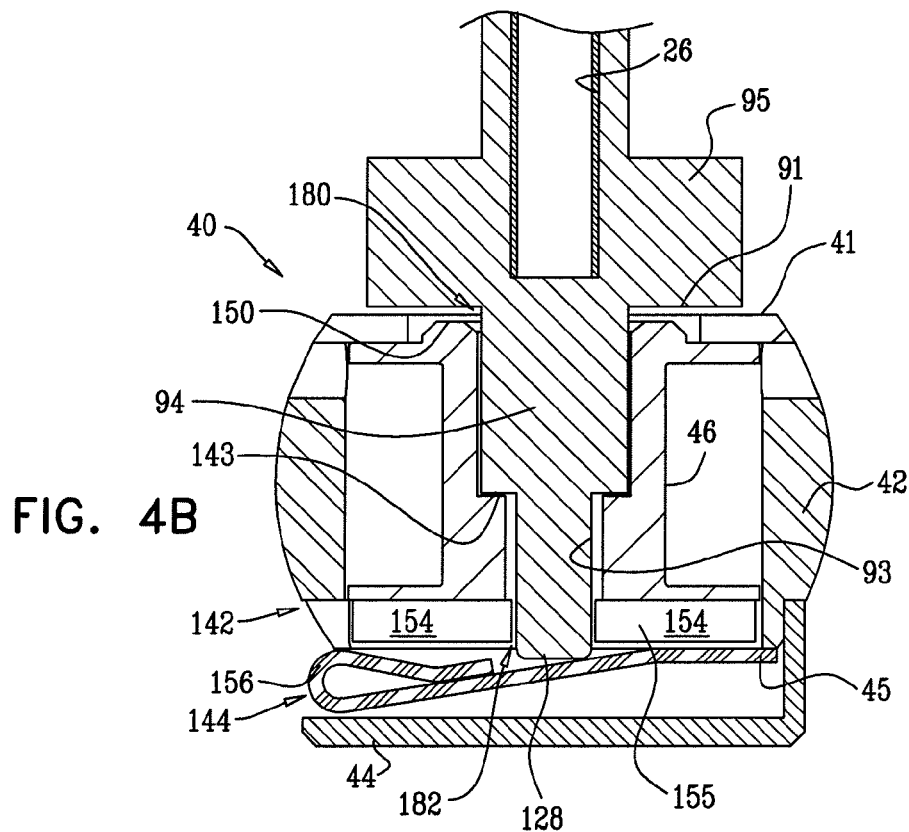
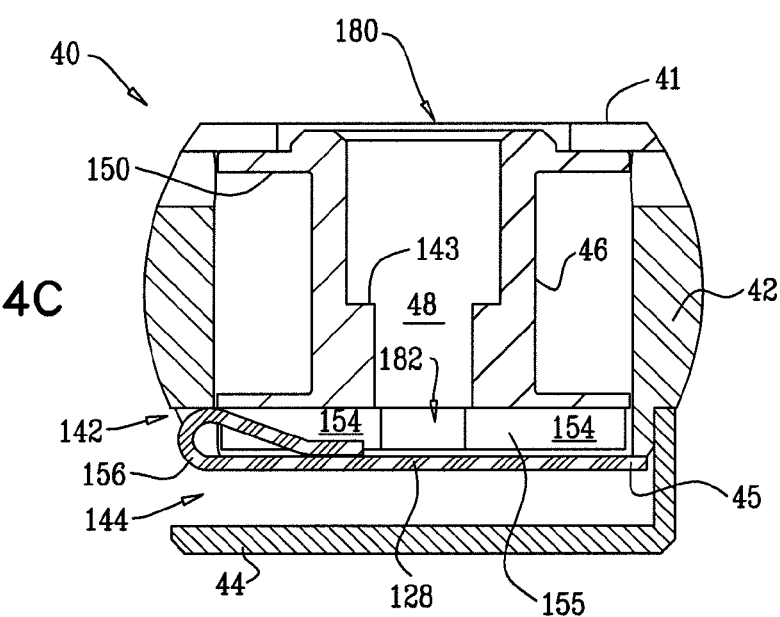

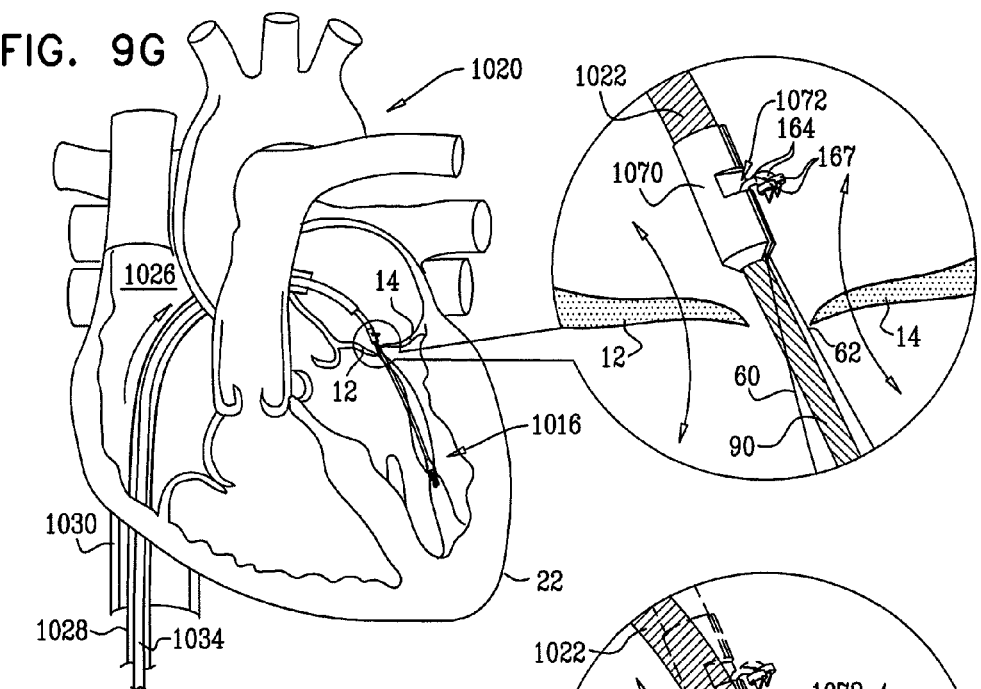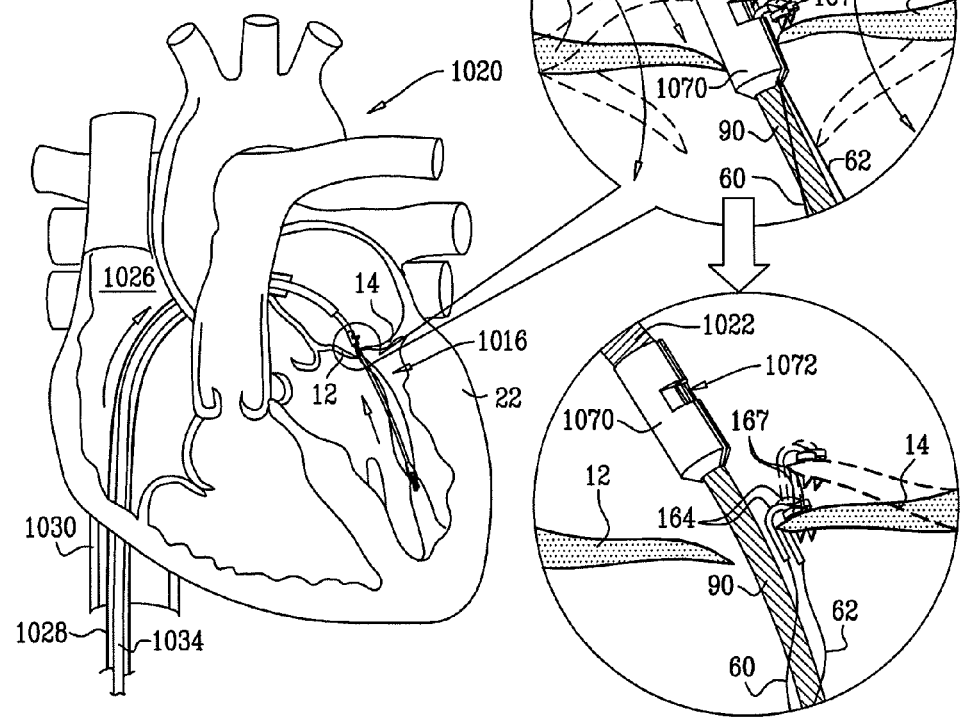

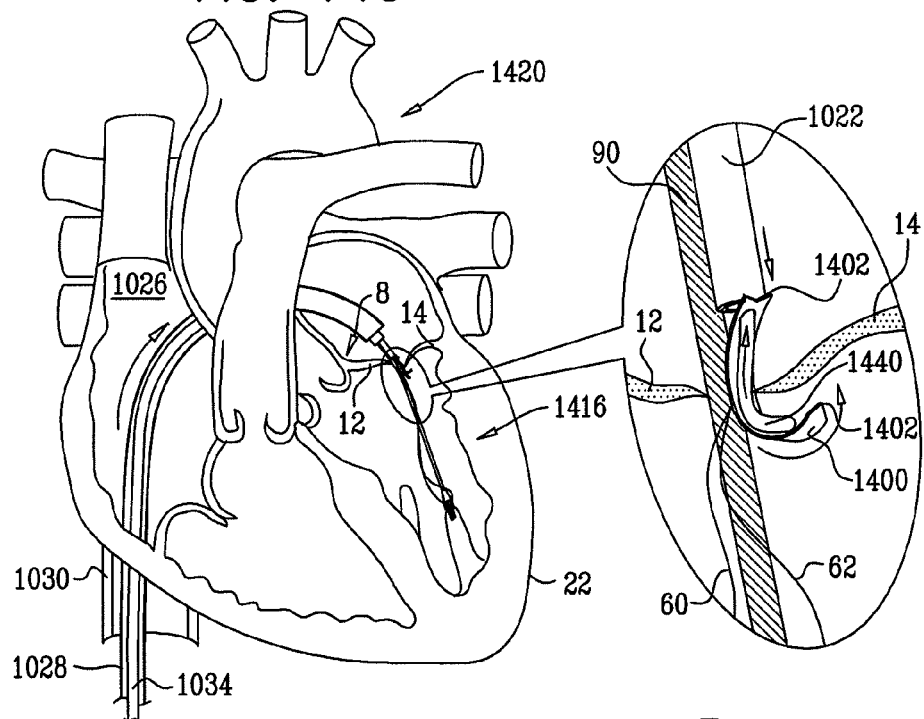
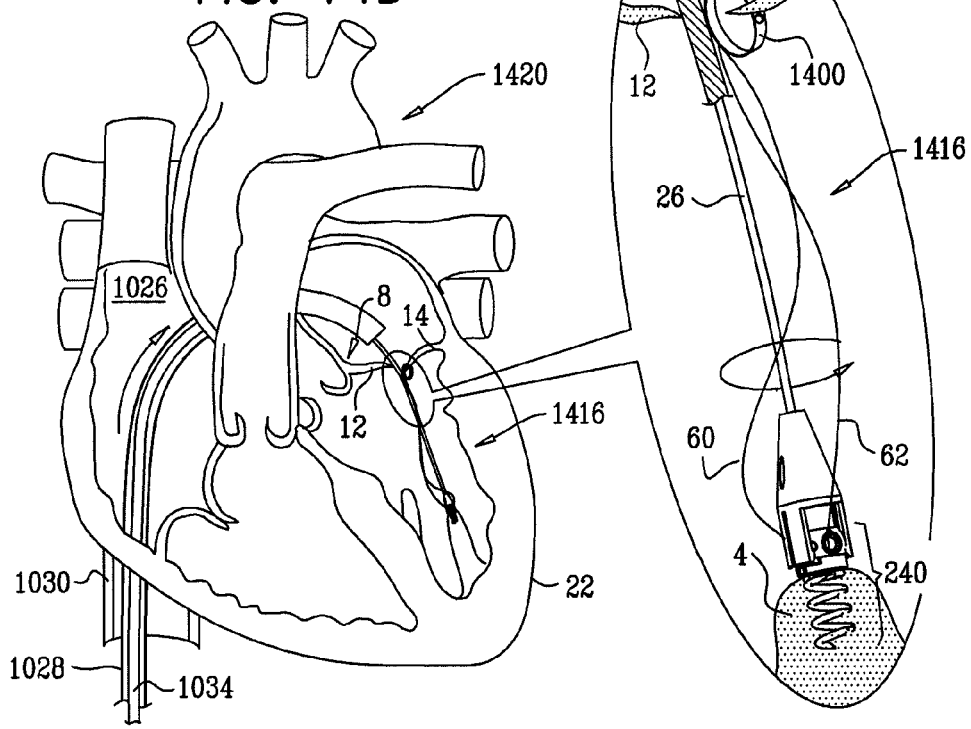

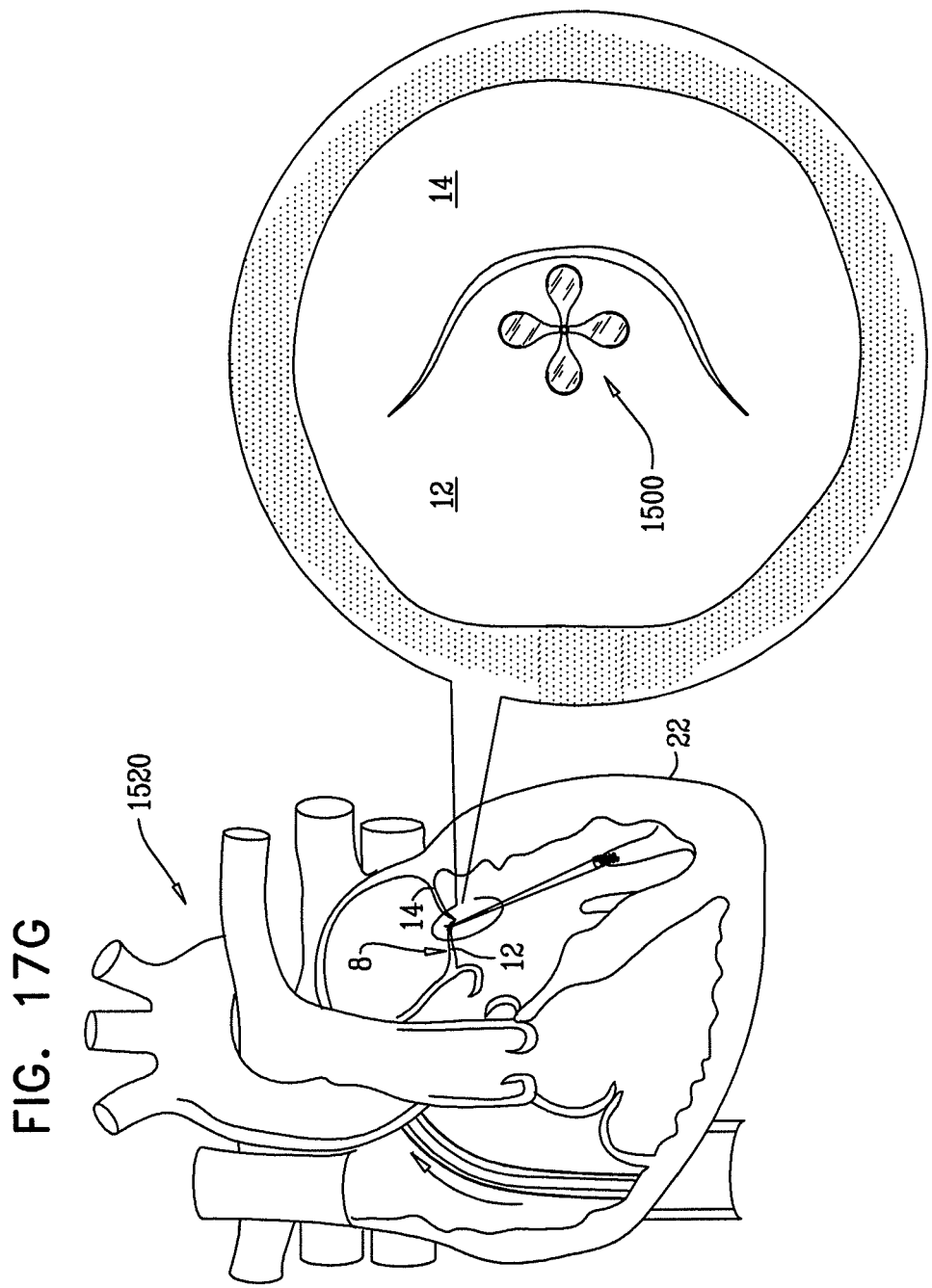

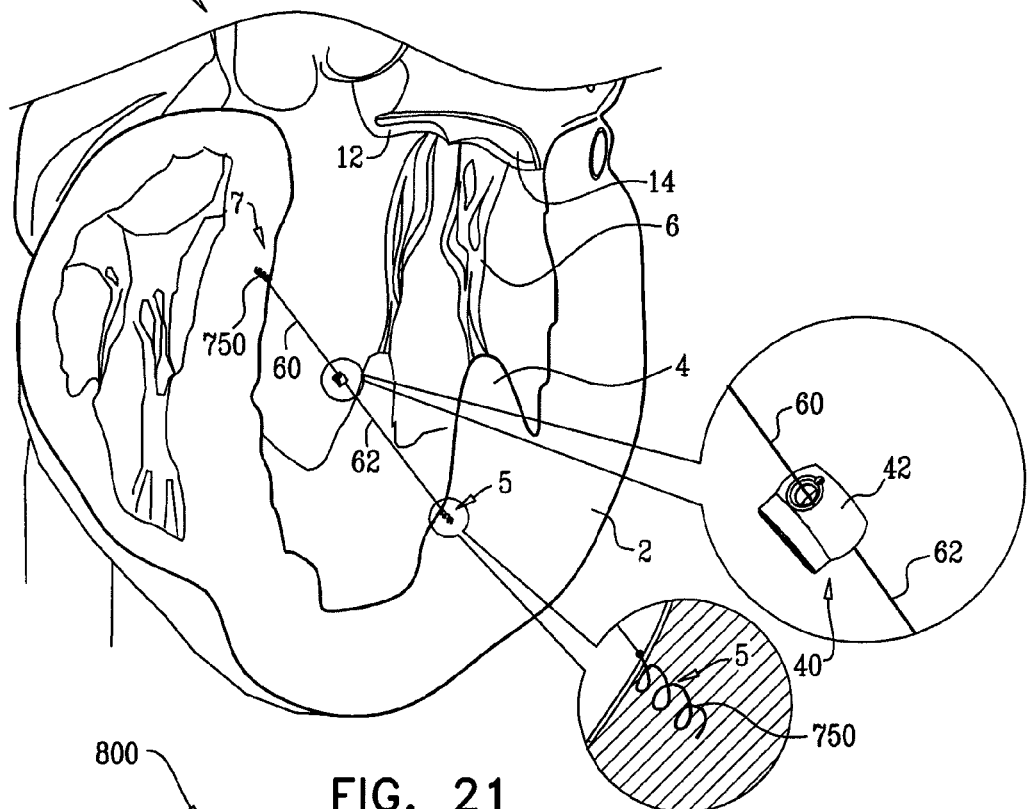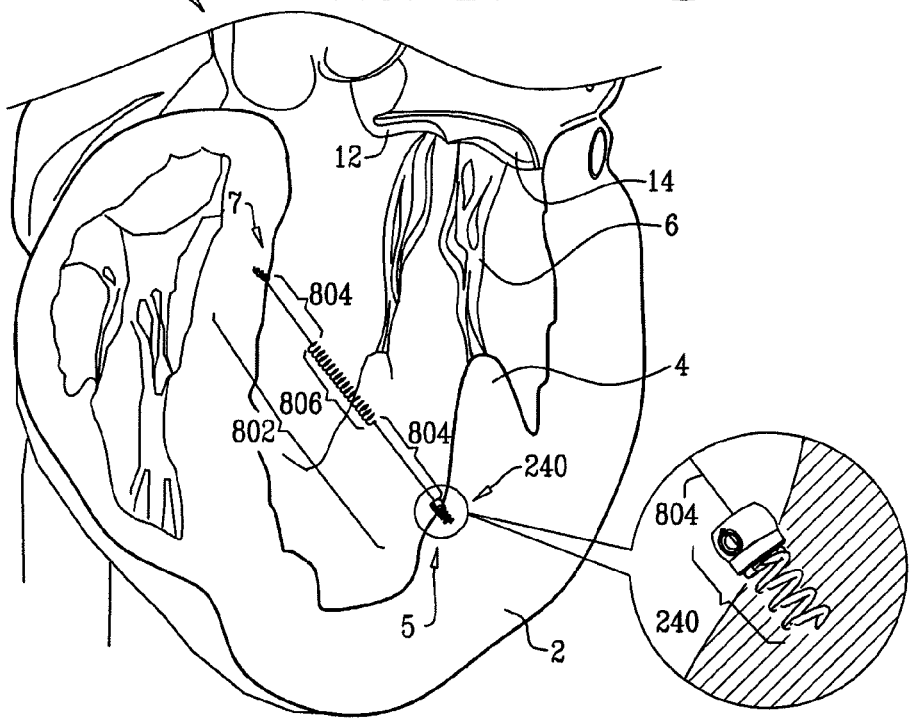

IMPLANTATION OF REPAIR CHORDS IN THE HEART

CROSS-REFERENCES TO RELATED APPLICATIONS

The present application is: a) a continuation-in-part of U.S. patent application Ser. No. 12/341,960 to Cabiri, entitled, "Adjustable annuloplasty ring and spool mechanism therefor," filed Dec. 22, 2008; and b) a continuation-in-part of U.S. patent application Ser. No. 12/435,291 to Maisano et al., entitled: "Adjustable repair chords and spool mechanism therefor," filed May 4, 2009.

Both of these applications are assigned to the assignee of the present application and are incorporated herein by reference.

FIELD OF THE INVENTION

The present invention relates in general to valve and chordae tendineae repair. More specifically, the present invention relates to repair of an atrioventricular valve and associated chordae tendineae of a patient.

BACKGROUND OF THE INVENTION

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

Chronic or acute left ventricular dilatation can lead to papillary muscle displacement with increased leaflet tethering due to tension on chordae tendineae, as well as annular dilatation.

U.S. Pat. No. 7,431,692 to Zollinger et al., which is incorporated herein by reference, describes an adjustable support pad for adjustably holding a tensioning line used to apply tension to a body organ. The adjustable support pad can include a locking mechanism for preventing slidable movement of the tensioning element in one or both directions. The locking mechanism may include spring-loaded locks, rotatable cam-like structures, and/or rotatable spool structures. The adjustable support pad may be formed from rigid, semi-rigid, and/or flexible materials, and may be formed to conform to the outer surface of a body organ. The adjustable support pad can be configured to adjustably hold one or more separate tensioning lines, and to provide for independent adjustment of one or more tensioning lines or groups thereof.

US Patent Application Publication 2007/0118151 to Davidson, which is incorporated herein by reference, describes a method and system to achieve leaflet coaptation in a cardiac valve percutaneously by creation of neochordae to prolapsing valve segments. This technique is especially useful in cases of ruptured chordae, but may be utilized in any segment of prolapsing leaflet. The technique described herein has the additional advantage of being adjustable in the beating heart. This allows tailoring of leaflet coaptation height under various loading conditions using image-guidance, such as echocardiography. This offers an additional distinct advantage over conventional open-surgery placement of artificial chordae. In traditional open surgical valve repair, chord length must be estimated in the arrested heart and may or may not be correct once the patient is weaned from cardiopulmonary bypass. The technique described below also allows for placement of multiple artificial chordae, as dictated by the patient's pathophysiology.

U.S. Pat. No. 6,626,930 to Allen et al., which is incorporated herein by reference, describes apparatus and method for the stabilization and fastening of two pieces of tissue. A single device may be used to both stabilize and fasten the two pieces of tissue, or a separate stabilizing device may be used in conjunction with a fastening device. The stabilizing device may comprise a probe with vacuum ports and/or mechanical clamps disposed at the distal end to approximate the two pieces of tissue. After the pieces of tissue are stabilized, they are fastened together using sutures or clips. One exemplary embodiment of a suture-based fastener comprises a toggle and suture arrangement deployed by a needle, wherein the needle enters the front side of the tissue and exits the blind side. In a second exemplary embodiment, the suture-based fastener comprises a needle connected to a suture. The needle enters the blind side of the tissue and exits the front side. The suture is then tied in a knot to secure the pieces of tissue. One example of a clip-based fastener comprises a spring-loaded clip having two arms with tapered distal ends and barbs. The probe includes a deployment mechanism which causes the clip to pierce and lockingly secure the two pieces of tissue.

Goar et al., which is incorporated herein by reference, describes methods, devices, and systems are provided for performing endovascular repair of atrioventricular and other cardiac valves in the heart. Regurgitation of an atrioventricular valve, particularly a mitral valve, can be repaired by modifying a tissue structure selected from the valve leaflets, the valve annulus, the valve chordae, and the papillary muscles. These structures may be modified by suturing, stapling, snaring, or shortening, using interventional tools which are introduced to a heart chamber. Preferably, the tissue structures will be temporarily modified prior to permanent modification. For example, opposed valve leaflets may be temporarily grasped and held into position prior to permanent attachment.

U.S. Pat. No. 6,752,813 to Goldfarb et al., which is incorporated herein by reference, describes methods and devices for grasping, and optional repositioning and fixation of the valve leaflets to treat cardiac valve regurgitation, particularly mitral valve regurgitation. Such grasping will typically be atraumatic providing a number of benefits. For example, atraumatic grasping may allow repositioning of the devices relative to the leaflets and repositioning of the leaflets themselves without damage to the leaflets. However, in some cases it may be necessary or desired to include grasping which pierces or otherwise permanently affects the leaflets. In some of these cases, the grasping step includes fixation.

US Patent Application Publication 2003/0105519 to Fasol et al., which is incorporated herein by reference, describes artificial chordae having a strand member and a first and second pair of sutures at either longitudinal end of the strand member. The artificial chordae is preferably a unitary unit, formed from inelastic flexible material. In one embodiment, the artificial chordae comprises multiple strand members joined together at a joined end. Different sized artificial chordae are provided sized to fit the patient's heart. The appropriately sized artificial chordae is chosen by using a chordae sizing gauge having a shaft and a transverse member, to measure the space within the patient's heart where the artificial chordae is attached.

The following patents and patent application publications may be of interest:

PCT Patent Application Publication WO 07/136,783 to Cartledge et al.
U.S. Pat. No. 5,306,296 to Wright et al.
U.S. Pat. No. 6,569,198 to Wilson et al.
U.S. Pat. No. 6,619,291 to Hlavka et al.
U.S. Pat. No. 6,764,510 to Vidlund et al.
U.S. Pat. No. 7,004,176 to Lau
U.S. Pat. No. 7,101,395 to Tremulis et al.
U.S. Pat. No. 7,175,660 to Cartledge et al.
US Patent Application Publication 2003/0050693 to Quijano et al
US Patent Application Publication 2003/0167062 to Gambale et al.
US Patent Application Publication 2004/0024451 to Johnson et al.
US Patent Application Publication 2004/0148021 to Cartledge et al.
US Patent Application Publication 2004/0236419 to Milo
US Patent Application Publication 2005/0171601 to Cosgrove et al.
US Patent Application Publication 2005/0216039 to Lederman
US Patent Application Publication 2005/0288781 to Moaddeb et al.
US Patent Application Publication 2007/0016287 to Cartledge et al.
US Patent Application Publication 2007/0080188 to Spence et al.
US Patent Application Publication 2009/0177266 to Powell et al.

The following articles may be of interest:

O'Reilly S et al., "Heart valve surgery pushes the envelope," Medtech Insight 8(3): 73, 99-108 (2006)

Dieter R S, "Percutaneous valve repair: Update on mitral regurgitation and endovascular approaches to the mitral valve," Applications in Imaging, Cardiac Interventions, Supported by an educational grant from Amersham Health pp. 11-14 (2003).

BRIEF SUMMARY OF THE INVENTION

In some embodiments of the present invention, subvalvular apparatus is provided comprising adjustable repair chords and a delivery tool for implantation thereof. The repair chords comprise one or more longitudinal members, e.g., sutures, wires, or elongate tensioning coils, which are coupled at respective first end portions thereof to an adjusting mechanism. In some embodiments, the repair chords function as artificial chordae tendineae. In other embodiments, the repair chords are used to adjust a distance between two portions of the ventricular wall.

In some embodiments of the present invention, the adjusting mechanism comprises a spool assembly. The spool assembly comprises a housing, which houses a spool to which first end portions of the longitudinal members are coupled. The housing is coupled to a tissue anchor, which facilitates implantation of the spool assembly in a first portion of tissue of the heart which faces and surrounds the ventricular lumen, such as a papillary muscle or a first portion of a ventricular wall of the heart. Second end portions of the longitudinal members are coupled (e.g., tied, sutured, clipped, or otherwise fastened) to a second portion of tissue which faces and surrounds the ventricle, such as a leaflet of an atrioventricular valve (e.g., a mitral valve or a tricuspid valve) or a second portion of the ventricular wall.

Once the second ends of the longitudinal members are coupled to the second portion of tissue of the heart that faces and surrounds the ventricle, the spool is rotated in order to adjust a length of the longitudinal member. During the rotation of the spool in a first direction thereof, the longitudinal member is wound around the spool thereby shortening and tensioning the longitudinal member. As a result, the ends of the longitudinal member coupled to the second portion of heart tissue, and consequently the second portion of tissue, are pulled toward the adjusting mechanism at the implantation site. Thus, for embodiments in which the repair chord functions as an artificial chorda tendinea, the longitudinal member replaces slackened native chordae tendineae and improves function of or restores normal function to the atrioventricular valve. For embodiments in which the repair chord is coupled to two portions of the ventricular wall, the two portions are drawn together, thereby restoring the dimensions of the heart wall to physiological dimensions, and drawing the leaflets toward one another.

In some embodiments of the present invention, the adjusting mechanism comprises a reversible locking mechanism which facilitates bidirectional rotation of the spool in order to effect both tensioning and relaxing of the longitudinal member. That is, the spool is wound in one direction in order to tighten the longitudinal member, and in an opposite direction in order to slacken the longitudinal member. Thus, the spool adjusting mechanism facilitates bidirectional adjustment of the repair chord.

In some embodiments of the present invention, the adjustable repair chords are implanted during an open-heart procedure. In these embodiments, the delivery tool comprises a handle and a multilumen shaft that is coupled at a distal end thereof to the adjusting mechanism. The delivery tool functions to advance the adjusting mechanism to the implantation site, implant the adjusting mechanism at the implantation site, and effect adjustment of the repair chord by effecting rotation of the spool. The multilumen shaft defines a primary lumen which houses an elongate torque-delivering tool and is slidable with respect to a shaft of the elongate torque-delivering tool. For embodiments in which the repair chord functions as an artificial chorda tendinea, prior to implantation of the adjusting mechanism, the distal portion of the delivery tool and the adjusting mechanism coupled thereto are advanced between the leaflets of the atrioventricular valve and into the ventricle toward the implantation site. During the implantation of the adjusting mechanism, the multilumen shaft is disposed around the portion of the torque-delivering tool that is positioned in the ventricle. Prior to the subsequent rotation of the spool, the multilumen shaft is pulled proximally with respect to the torque-delivering tool that is left in place during the pulling. The multilumen shaft is pulled such that a distal end thereof is disposed proximal to the valve and in the atrium.

The incision made in the heart is then closed around the delivery tool and the heart resumes its normal function during the adjustment of the length of the artificial chorda. The retracting of the multilumen shaft reduces a diameter of the delivery tool at the portion thereof that is disposed between the leaflets of the valve. Such reducing of the diameter reduces the interference of the portion of the delivery tool on the beating heart valve and the adjustment of the artificial chorda is performed with minimal interference to the valve by the delivery tool.

In other embodiments of the present invention, the adjustable repair chords are implanted during a transcatheter procedure. In these embodiments, the delivery tool typically comprises a surrounding shaft, which is configured to be slidable over and along a central shaft, such that the surrounding shaft surrounds a portion of the central shaft. The delivery tool is advanced through a sheath and into the left ventricle. All or a portion of the delivery tool is rotated in order to screw the anchor of the spool assembly into tissue of a papillary muscle.

The surrounding shaft is withdrawn proximally into the atrium, while maintaining the distal end of the central shaft in place and within the ventricle. The surrounding shaft is advanced distally between the leaflets. While the distal end of the central shaft is maintained in place and within the ventricle, the surrounding shaft is used to engage one or more of the leaflets with one or more leaflet-engaging elements. In order to couple the leaflet-engaging elements to the leaflet, if necessary the surgeon may manipulate the surrounding shaft (e.g., push the shaft against the leaflet, and/or slightly withdraw and advance the shaft one or more times). Alternatively or additionally, the natural motion of the leaflet may engage the leaflet with the leaflet-engaging elements. It is noted that before and after this engagement occurs, the leaflets are free to open and close during the natural cardiac cycle.

In some embodiments of the present invention, apparatus and method described herein may be used for providing artificial chordae tendineae in a left ventricle of the heart and effecting adjustment thereof. In some embodiments, apparatus and method described herein may be used for providing artificial chordae tendineae in a right ventricle of the heart and effecting adjustment thereof. In some embodiments, apparatus and method described herein may be used for providing a system to adjust a length between two portions of the heart wall.

There is therefore provided, in accordance with an embodiment of the present invention, a method, including:

positioning, at an intraventricular site of a ventricle of a patient, a spool coupled to a first end portion of a longitudinal member; and coupling a second end portion of the longitudinal member to a portion of tissue facing a lumen of the ventricle.

In an embodiment, positioning the spool includes transcatheterally advancing the spool toward the intraventricular site.

In an embodiment, positioning the spool includes advancing the spool toward the intraventricular site during an open-heart procedure.

In an embodiment, positioning the spool includes advancing the spool toward the intraventricular site during a minimally-invasive procedure.

In an embodiment, coupling the second end portion of the longitudinal member to the portion of tissue facing the ventricular lumen includes coupling the second end portion of the longitudinal member to a leaflet of an atrioventricular valve of the patient.

In an embodiment, positioning the spool includes implanting the spool at the intraventricular site.

In an embodiment, implanting the spool in the intraventricular site includes suturing the spool to the intraventricular site.

In an embodiment, the spool is coupled to a tissue anchor, and implanting the spool at the intraventricular site includes implanting the tissue anchor in tissue of the ventricle such that a distal end of the tissue anchor is disposed within the tissue of the ventricle and does not extend beyond a pericardium of a heart of the patient.

In an embodiment, the tissue facing the lumen of the ventricle is at least one leaflet of an atrioventricular valve of the patient, the longitudinal member is an artificial chorda tendinea, and the spool is coupled to the first end portion of the artificial chorda tendinea, and implanting the spool includes:

advancing, between leaflets of the atrioventricular valve and into the ventricle, at least a shaft of a delivery tool, to which shaft the spool is removably coupled, and implanting the spool at the intraventricular site; and while the shaft remains coupled to the spool after implanting the spool, coupling, using a coupling element holder of the delivery tool, at least one leaflet-engaging element to the at least one leaflet, a second end portion of the artificial chorda tendinea is coupled to the at least one leaflet-engaging element.

In an embodiment, implanting the spool at the intraventricular site includes implanting the spool at a papillary muscle of the ventricle of the patient.

In an embodiment, implanting the spool at the intraventricular site includes implanting the spool at an inner wall of the ventricle of the patient.

In an embodiment, advancing the at least the shaft includes transcatheterally advancing the at least the shaft.

In an embodiment, coupling the at least one leaflet-engaging element to the at least one leaflet includes coupling the at least one leaflet-engaging element to exactly one leaflet.

In an embodiment, coupling the at least one leaflet-engaging element to the at least one leaflet while the shaft remains coupled to the spool includes using the shaft to provide a reference force to the leaflet-engaging element.

In an embodiment, using the coupling element holder of the delivery tool includes sliding the coupling element holder with respect to the shaft.

In an embodiment, the at least one leaflet-engaging element is a butterfly clip, which includes a plurality of petals arranged around a needle, and coupling includes penetrating the needle and petals through a ventricular surface of the at least one leaflet until the needle and petals emerge from an atrial surface of the at least one leaflet, and the petals unfold and couple the clip to the at least one leaflet.

In an embodiment, the method further includes adjusting, from a site outside of a body of the patient, a length of the artificial chorda tendinea.

In an embodiment, the spool is coupled to first end portions of respective first and second artificial chordae tendineae, coupling the at least one leaflet-engaging element includes coupling at least first and second leaflet-engaging elements to respective first and second leaflets, and second end portions of the respective first and second artificial chordae tendineae are coupled to respective first and second leaflet-engaging elements.

In an embodiment, coupling the leaflet-engaging elements includes using the artificial chordae tendineae to draw together the first and second leaflets.

In an embodiment, drawing together includes drawing together the first and second leaflets using a bead through which the artificial chordae tendineae pass.

In an embodiment, the at least one leaflet-engaging element is a clip, and coupling includes clamping the clip on the at least one leaflet such that the clip engages atrial and ventricular surfaces of the leaflet.

In an embodiment, the clip includes two clip jaws, and clamping includes holding the clip jaws within respective tool jaws of the coupling element holder, and opening and closing the clip jaws using the tool jaws.

In an embodiment, the at least one leaflet-engaging element is a non-continuous ring, and coupling includes coupling the non-continuous ring to the at least one leaflet.

In an embodiment, coupling the non-continuous ring to the at least one leaflet includes initially holding the non-continuous ring in an extended position using a deforming rod, positioning the non-continuous ring in a vicinity of the at least one leaflet, and thereafter separating the deforming rod from the non-continuous ring such that the non-continuous ring assumes an annular position coupled to the at least one leaflet.

In an embodiment, the at least one leaflet-engaging element is at least one hook, and coupling includes puncturing the at least one leaflet with the at least one hook.

In an embodiment, puncturing the at least one leaflet with the at least one hook includes sliding the at least one hook proximally to an atrial surface of the at least one leaflet and subsequently puncturing the leaflet by sliding the at least one hook distally.

In an embodiment, puncturing the at least one leaflet includes sliding the at least one hook proximally to an atrial surface of the leaflet and allowing the at least one leaflet to engage the at least one hook responsively to beating of the leaflet.

In an embodiment,
positioning the spool includes positioning the spool at a first portion of tissue facing the ventricular lumen,
coupling the second end portion of the longitudinal member to the portion of tissue includes coupling the second end portion of the longitudinal member to a second portion of tissue facing the ventricular lumen, and
the method further includes:
rotating the spool,
by the rotating of the spool, winding a portion of the longitudinal member around the spool,
by the winding of the portion, shortening a length of the longitudinal member, and
by the shortening of the length of the longitudinal member, drawing together the first and second portions of the tissue facing the ventricular lumen of the patient.

In an embodiment, the method includes adjusting, from a site outside of a body of the patient, the length of the longitudinal member.

In an embodiment,
positioning the spool at the first portion of tissue includes implanting the spool at a papillary muscle of a left ventricle of the patient,
coupling the second end portion of the longitudinal member to the second portion of tissue includes coupling the second end portion of the longitudinal member to a leaflet of a mitral valve of the patient, and
drawing together the first and second portions of the tissue facing the ventricular lumen includes drawing the leaflet toward the papillary muscle.

In an embodiment,
positioning the spool at the first portion of tissue includes implanting the spool at a papillary muscle of a right ventricle of the patient,
coupling the second end portion of the longitudinal member to the second portion of tissue includes coupling the second end portion of the longitudinal member to a leaflet of a tricuspid valve of the patient, and
drawing together the first and second portions of the tissue facing the ventricular lumen includes drawing the leaflet toward the papillary muscle.

In an embodiment,
positioning the spool at the first portion of tissue includes implanting the spool at a first portion of tissue of an inner wall of a left ventricle of the patient,
coupling the second end portion of the longitudinal member to the second portion of tissue includes coupling the second end portion of the longitudinal member to a leaflet of a mitral valve of the patient, and
drawing together the first and second portions of the tissue facing the ventricular lumen includes drawing the leaflet toward the first portion of tissue of the inner wall of the ventricle.

In an embodiment,
positioning the spool at the first portion of tissue includes implanting the spool at a first portion of an inner wall of a right ventricle of the patient,
coupling the second end portion of the longitudinal member to the second portion of tissue includes coupling the second end portion of the longitudinal member to a leaflet of a tricuspid valve of the patient, and
drawing together the first and second portions of the tissue facing the ventricular lumen includes drawing the leaflet toward the first portion of tissue of the inner wall of the ventricle.

In an embodiment,
positioning the spool at the first portion of tissue includes implanting the spool at a first portion of an inner wall of the ventricle of the patient,
coupling the second end portion of the longitudinal member to the second portion of tissue includes coupling the second end portion of the longitudinal member to a second portion of the inner wall of the ventricle of the patient, and
drawing together the first and second portions of the tissue facing the ventricular lumen includes drawing the first and second portions of tissue of the inner wall of the ventricle toward one another.

In an embodiment, the method includes adjusting, from a site outside of a body of the patient, the length of the longitudinal member.

In an embodiment,
positioning the spool at the first portion of tissue includes implanting the spool at a papillary of the ventricle of the patient,
coupling the second end portion of the longitudinal member to the second portion of tissue includes coupling the second end portion of the longitudinal member to a portion of an inner wall of the ventricle of the patient, and
drawing together the first and second portions of the tissue facing the ventricular lumen includes drawing the papillary muscle and the portion of tissue of the inner wall of the ventricle toward one another.

In an embodiment, positioning the spool coupled to the first end portion of the longitudinal member includes positioning a spool coupled to at least first and second longitudinal members at respective first end portions thereof, each longitudinal member having respective second end portions thereof, and the method further includes:
coupling the second end portion of the first longitudinal member to a first portion of heart tissue facing the ventricular lumen;
coupling the second end portion of the second longitudinal member to a second portion of heart tissue facing the ventricular lumen; and
drawing the first and second portions of heart tissue toward one another.

In an embodiment, positioning the spool includes implanting the spool at a papillary muscle.

In an embodiment, positioning the spool includes implanting the spool at a portion of tissue of an inner wall of the ventricle facing the ventricular lumen.

In an embodiment,
coupling the second end portion of the first longitudinal member to the first portion of tissue includes coupling the second end portion of the first longitudinal member to a first portion of an inner wall of the ventricle,
coupling the second end portion of the second longitudinal member to the second portion of tissue includes coupling the second end portion of the second longitudinal member to a second portion of an inner wall of the ventricle, and
drawing the first and second portions of heart tissue toward one another includes drawing together the first and second portions of the inner wall of the ventricle.

In an embodiment,
coupling the second end portion of the first longitudinal member to the first portion of tissue includes coupling the second end portion of the first longitudinal member to a portion of an inner wall of the ventricle,
coupling the second end portion of the second longitudinal member to the second portion of tissue includes coupling the second end portion of the second longitudinal member to a papillary muscle of the ventricle, and
drawing the first and second portions of heart tissue toward one another includes drawing the portion of the inner wall of the ventricle and the papillary muscle toward one another.

In an embodiment,
coupling the second end portion of the first longitudinal member to the first portion of tissue includes coupling the second end portion of the first longitudinal member to a leaflet of an atrioventricular valve,
coupling the second end portion of the second longitudinal member to the second portion of tissue includes coupling the second end portion of the second longitudinal member to a papillary muscle of the ventricle, and
drawing the first and second portions of heart tissue toward one another includes drawing the leaflet and the papillary muscle toward one another.

In an embodiment,
coupling the second end portion of the first longitudinal member to the first portion of tissue includes coupling the second end portion of the first longitudinal member to a leaflet of an atrioventricular valve,
coupling the second end portion of the second longitudinal member to the second portion of tissue includes coupling the second end portion of the second longitudinal member to a portion of an inner wall of the ventricle, and
drawing the first and second portions of heart tissue toward one another includes drawing the leaflet and the portion of the inner wall toward one another.

In an embodiment,
coupling the second end portion of the first longitudinal member to the first portion of tissue includes coupling the second end portion of the first longitudinal member to a first leaflet of an atrioventricular valve,
coupling the second end portion of the second longitudinal member to the second portion of tissue includes coupling the second end portion of the second longitudinal member to a second leaflet of the atrioventricular valve, and
drawing the first and second portions of heart tissue toward one another includes drawing the first and second leaflets toward one another.

In an embodiment, the method includes advancing the spool toward the intraventricular site by advancing a portion of a delivery tool that is reversibly coupled to the spool between leaflets of an atrioventricular valve having at least first and second leaflets thereof, and positioning the spool at the intraventricular site includes manipulating the delivery tool to position the spool at the intraventricular site.

In an embodiment, the method includes, after positioning the spool:
decoupling the delivery tool from the spool,
removing the delivery tool from the ventricle, and
subsequently to the removing, accessing the spool at the intraventricular site.

In an embodiment, accessing the spool includes recoupling the delivery tool to the spool by advancing the delivery tool along at least one guide wire coupled to the spool.

In an embodiment, accessing the spool includes coupling a torque-delivering tool to the spool by advancing the torque-delivering tool through an elongate tube coupled at a first end thereof to the spool and at second end thereof to a portion of subcutaneous tissue of the patient.

In an embodiment, the method further includes, after coupling the second end portion of the longitudinal member to the portion of tissue facing the ventricular lumen:
sliding a shaft of the delivery tool with respect to a torque-delivering tool of the delivery tool, and sliding a proximal portion of the shaft into a lumen of a handle portion of the delivery tool; and
subsequently to the sliding, rotating the spool.

In an embodiment, sliding the shaft includes:
sliding the shaft until a distal portion of the shaft is disposed proximally to the atrioventricular valve, and
responsively, reducing a diameter of the portion of the delivery tool disposed between the leaflets of the valve.

In an embodiment, reducing the diameter of the portion of the delivery tool disposed between the leaflets of the valve includes reducing the diameter to between 0.8 mm and 1.5 mm.

In an embodiment,
positioning the spool includes positioning the spool coupled to a mechanical locking element having a surface coupled to the lower surface of the rotatable structure, and
the method further includes:
advancing an elongate tool through a channel provided by the spool;
unlocking the spool from the mechanical locking element by pushing a depressible portion of the surface of the locking element;
responsively to the pushing of the depressible portion, dislodging a protrusion protruding out of a plane of the surface of the mechanical element from within a recess defined by the spool; and
rotating the spool.

In an embodiment,
during a first period:
pushing the depressible portion includes maintaining the protrusion in a position in which it is dislodged from the recess; and
rotating the spool;
the method further includes, during a second period:
removing the elongate tool from within the channel and facilitating positioning of the protrusion in the recess; and
restricting rotation of the spool.

There is additionally provided, in accordance with an embodiment of the present invention apparatus including:
a delivery tool including:
a handle portion defining a handle lumen; and
a shaft (a) being slidable with respect to the handle, and (b) having a proximal portion thereof being slidable into the handle lumen during proximal sliding of the shaft;

a spool removably couplable to the distal end of the delivery tool and configured to be implanted in an intraventricular site of a ventricle of a patient; and at least one longitudinal member having opposite first and second end portions, the first end portion being coupled to the spool and the second end portion configured to be coupled to a first portion of heart tissue that surrounds a ventricular space of the ventricle of the patient, the longitudinal member configured to be wound around the spool in response to rotation of the spool, and, responsively, to draw the second end portion of the longitudinal member and the first portion of heart tissue toward the first end portion of the longitudinal member.

In an embodiment, the shaft is shaped to provide at least one secondary lumen configured for housing a section of the longitudinal member that is between the first and second end portions thereof.

In an embodiment, the longitudinal member includes expanded polytetrafluoroethylene (ePTFE).

In an embodiment, at least a portion of the longitudinal member is shaped to define a coil, and the coil is configured to apply a tensioning force to the first portion of heart tissue.

In an embodiment, the longitudinal member is coated with polytetrafluoroethylene.

In an embodiment, the apparatus includes a locking mechanism coupled to the spool and configured to restrict rotation of the spool.

In an embodiment,
the at least one longitudinal member includes at least first and second longitudinal members having respective first and second end portions thereof,
the first end portions of the first and second longitudinal members are coupled to the spool, the second end portion of the first longitudinal member is configured to be coupled to a leaflet of an atrioventricular valve,
the second end portion of the second longitudinal member is configured to be coupled to a portion of tissue of an inner wall of the ventricle, and
in response to rotation of the spool, the first and second longitudinal members are tightened and pull the leaflet toward the portion of tissue of the inner wall.

In an embodiment,
the at least one longitudinal member includes at least first and second longitudinal members having respective first and second end portions thereof,
the first end portions of the first and second longitudinal members are coupled to the spool, the second end portion of the first longitudinal member is configured to be coupled to a leaflet of an atrioventricular valve,
the second end portion of the second longitudinal member is configured to be coupled to a papillary muscle of the ventricle, and
in response to rotation of the spool, the first and second longitudinal members are tightened and pull the leaflet toward the papillary muscle.

In an embodiment,
the at least one longitudinal member includes at least first and second longitudinal members having respective first and second end portions thereof,
the first end portions of the first and second longitudinal members are coupled to the spool,
the second end portion of the first longitudinal member is configured to be coupled to a first portion of tissue of an inner wall of the ventricle,
the second end portion of the second longitudinal member is configured to be coupled to a second portion of tissue of the inner wall of the ventricle, and in response to rotation of the spool, the first and second longitudinal members are tightened and pull the first and second portions of tissue of the inner wall toward one another.

In an embodiment, the apparatus includes an elongate tube coupled at a first end to the spool and at a second end thereof to subcutaneous tissue of the patient, the elongate tube is configured to facilitate accessing of a torque-delivering tool to the spool following (a) the implantation of the spool at the intraventricular site and (b) subsequent removal of the delivery tool.

In an embodiment, the spool is configured to be coupled to a second portion of heart tissue that surrounds the ventricular space, and, in response to the rotation of the spool, the longitudinal member is configured to draw the first and second portions of heart tissue toward one another.

In an embodiment,
the first portion of heart tissue includes a first portion of an inner wall of the ventricle,
the second end portion of the longitudinal member is configured to be coupled to the first portion of the inner wall of the ventricle, and
in response to the rotation of the spool, the longitudinal member is configured to draw the first portion of the inner wall of the ventricle toward the second portion of heart tissue.

In an embodiment,
the first portion of heart tissue includes a leaflet of a mitral valve of the patient,
the second end portion of the longitudinal member is configured to be coupled to the leaflet of the mitral valve of the patient,
the second portion of heart tissue includes tissue of a papillary muscle of a left ventricle,
the spool is configured to be implanted in the tissue of the papillary muscle of the left ventricle, and
the spool is configured to adjust a length of the longitudinal member between the papillary muscle and the leaflet of the mitral valve.

In an embodiment,
the first portion of heart tissue includes a leaflet of a mitral valve of the patient,
the second end portion of the longitudinal member is configured to be coupled to the leaflet of the mitral valve of the patient,
the second portion of heart tissue includes a second portion of an inner wall of a left ventricle,
the spool is configured to be coupled to the second portion of the inner wall of the left ventricle, and
the spool is configured to adjust a length of the longitudinal member between the second portion of the inner wall and the leaflet of the mitral valve.

In an embodiment,
the first portion of heart tissue includes a leaflet of a tricuspid valve of the patient,
the second end portion of the longitudinal member is configured to be coupled to the leaflet of the tricuspid valve of the patient,
the second portion of heart tissue includes tissue of a papillary muscle of a right ventricle,
the spool is configured to be implanted in the tissue of the papillary muscle of the right ventricle, and
the spool is configured to adjust a length of the longitudinal member between the papillary muscle and the leaflet of the tricuspid valve.

In an embodiment,
the first portion of heart tissue includes a leaflet of a tricuspid valve of the patient, the second end portion of the longitudinal member is configured to be coupled to the leaflet of the tricuspid valve of the patient,
the second portion of heart tissue includes a second portion of an inner wall of a right ventricle,
the spool is configured to be coupled to the second portion of the inner wall of the right ventricle, and
the spool is configured to adjust a length of the longitudinal member between the second portion of the inner wall and the leaflet of the tricuspid valve.

In an embodiment, the apparatus includes at least one guide wire coupled to the spool, and, subsequently to the implantation of the spool, the delivery tool is configured to be:
decoupled from the spool and removed from the ventricle, and
advanceable along the guide wire.

In an embodiment, the guide wire is configured to facilitate access of a torque-delivering tool to the spool following the implantation of the spool at the intraventricular site.

In an embodiment, the apparatus includes a torque-delivering tool, the shaft is shaped to define at least a primary lumen,
the torque-delivering tool is disposed in the primary lumen and is coupled at a proximal end thereof to the handle, and
the shaft is slidable with respect to the torque-delivering tool.

In an embodiment, the delivery tool is configured to be advanceable between leaflets of an atrioventricular valve of the patient, and the shaft is slidable with respect to the torque-delivering tool in a manner that reduces a diameter of a portion of the delivery tool that is disposed between the leaflets of the valve.

In an embodiment, the handle lumen has a handle-lumen-length of between 50 mm and 100 mm, and the shaft is slidable in a first direction thereof to advance the proximal portion thereof into the lumen of the delivery tool.

In an embodiment, the distal portion of the torque-delivering tool is configured to be positioned within the ventricular space of the heart and defines a torque-delivering tool length at the distal portion of between 50 mm and 100 mm, and a ratio of the handle-lumen-length and the torque-delivering tool length at the distal portion is between 0.7:1 and 1.3:1.

In an embodiment,
the first portion of heart tissue includes an atrioventricular valve having at least first and second leaflets thereof,
the at least one longitudinal member includes at least first and second longitudinal members having respective first and second end portions thereof,
the first end portions of the first and second longitudinal members are coupled to the spool, the second end portion of the first longitudinal member is configured to be coupled to the first leaflet of the valve,
the second end portion of the second longitudinal member is configured to be coupled to the second leaflet of the valve, and
in response to rotation of the spool, the first and second longitudinal members are tightened and pull on the respective second end portions thereof toward the spool.

In an embodiment, in response to rotation of the spool in a first direction thereof, the respective first end portions of the first and second longitudinal members are configured to be wound around the spool, and, responsively, to pull the respective second end portions of the first and second longitudinal members toward the spool, and responsively to draw the first and second leaflets toward one another.

In an embodiment, the apparatus includes a housing surrounding the spool, the housing being coupled in part to a cap having a surface that is disposed in parallel with the lower surface of the spool, and the depressible portion is disposed between the lower surface of the spool and the cap.

In an embodiment, the apparatus includes a housing surrounding the spool, the housing being shaped to define a recessed portion thereof configured to receive the protrusion during the resting state of the mechanical element.

In an embodiment, the apparatus includes a torque-delivering tool disposed within a primary lumen of the shaft, the torque-delivering tool is coupled at a distal end thereof to the elongate rotation tool, and the torque-delivering tool is configured to facilitate rotation of the spool by facilitating rotation of the elongate tool.

There is yet further provided, in accordance with an embodiment of the present invention, apparatus, including:
a rotatable structure having a first end shaped to define a first opening, and a second end shaped to define a second opening, the rotatable structure being shaped to define a channel extending from the first opening to the second opening, the channel being configured for passage therethrough of an elongate tool, and the second end of the structure having a lower surface thereof shaped to:
provide at least a portion thereof having a circumference, and define one or more recesses at locations along the circumference; and
a mechanical element having a surface coupled to the lower surface of the rotatable structure, the mechanical element being shaped to provide:
a protrusion protruding out of a plane of the surface of the mechanical element, the protrusion being disposed within one of the recesses during a resting state of the mechanical element, in a manner that restricts rotation of the rotatable structure, and
a depressible portion coupled to the protrusion, the depressible portion being disposed in communication with the second opening of the lower surface, and configured to dislodge the protrusion from within the recess in response to a force applied thereto by the elongate tool.

In an embodiment,
during a first period:
the elongate tool is configured to maintain the protrusion in a position in which it is dislodged from the recess, and
the elongate tool is configured to rotate the rotatable structure, and during a second period:
the elongate tool is configured to remove the elongate tool from the channel and to position the protrusion in the recess, and
the rotatable structure is restricted from being rotated.

In an embodiment, the apparatus includes a housing surrounding the rotatable structure, the housing being coupled in part to a cap having a surface that is disposed in parallel with the lower surface of the rotatable structure, and the depressible portion is disposed between the lower surface of the rotatable structure and the cap.

In an embodiment, the apparatus includes a housing surrounding the rotatable structure, the housing being shaped to define a recessed portion thereof configured to receive the protrusion during the resting state of the mechanical element.

In an embodiment, the rotatable structure includes a spool, and the apparatus further includes a longitudinal member configured to be coupled at least a first end portion thereof to the spool and to be wrapped around the spool in response to rotation of the spool in a first direction thereof.

In an embodiment,
during a first period:
the elongate tool is configured to maintain the protrusion in a position in which it is dislodged from the recess, and the elongate tool is configured to rotate the spool, and during a second period:
the elongate tool is configured to remove the elongate tool from the channel and to position the protrusion in the recess, and
the spool is restricted from being rotated.

In an embodiment,
the spool is configured for implantation in a first portion of heart tissue that defines a ventricular lumen of the ventricle of a patient,
the longitudinal member is configured to be coupled at a second end portion thereof to a second portion of heart tissue that defines a ventricular lumen of the ventricle of the patent, and in response to rotation of the spool in a first direction thereof, the longitudinal member is configured to be wound around the spool, and, responsively, to shorten a distance between the second end portion of the longitudinal member and the spool.

There is still further provided, in accordance with an embodiment of the present invention, a method, including:
providing a rotatable structure coupled to a mechanical locking element having a surface coupled to the lower surface of the rotatable structure;
implanting the rotatable structure in cardiac tissue;
advancing an elongate tool through a channel provided by the rotatable structure;
unlocking the rotatable structure from the mechanical locking element by pushing a depressible portion of the surface of the locking element;
responsively to the pushing of the depressible portion, dislodging a protrusion protruding out of a plane of the surface of the mechanical element from within a recess defined by the rotatable structure; and
rotating the rotatable structure.

There is additionally provided, in accordance with an embodiment of the present invention, an implant delivery tool for use with an implant, the tool including:
an implant-coupling portion;
an elongate delivery tool shaft having a proximal end thereof and a distal end, the distal end being coupled at a distal end thereof to the implant-coupling portion; and
a tissue-engaging-device holder coupled along a portion of the shaft between the implant-coupling portion and the proximal end of the shaft, the tissue-engaging-device holder being shaped to define at least one coupling site for coupling the tissue-engaging-device.

In an embodiment, the apparatus includes an implant assembly including at least one longitudinal member coupled at a free end thereof to a tissue-engaging-device.

In an embodiment, the longitudinal member extends along the shaft toward the tissue-engaging-device holder, and the tissue-engaging-device holder is shaped to provide a projection thereof configured for winding excess portions of the longitudinal member therearound.

There is yet additionally provided, in accordance with an embodiment of the present invention, apparatus, including:
an intraventricular adjusting assembly configured to be implanted in an intraventricular site of a ventricle of a patient;
an elongate coupling tube coupled at a first end thereof to the intraventricular adjusting assembly and at second end thereof to a portion of subcutaneous tissue of the patient; and
an extracardiac tool configured to access the adjusting assembly from a site external to a body of the patient.

There is still yet additionally provided, in accordance with an embodiment of the present invention, a method, including:
implanting an adjusting assembly at an intraventricular site of a ventricle of a patient;
accessing the adjusting assembly by an extracardiac tool from a site external to a body of the patient by passing the tool through an elongate coupling tube that is coupled at a first end thereof to the intraventricular adjusting assembly and at second end thereof to a portion of subcutaneous tissue of the patient.

There is also provided, in accordance with an embodiment of the present invention, a method including:
advancing a distal end of a central shaft of a delivery tool between leaflets of an atrioventricular valve of a patient and into a ventricle of the patient;
while maintaining the distal end of the central shaft in place and within the ventricle:
proximally withdrawing a surrounding shaft of the delivery tool with respect to the distal end of the central shaft and toward the leaflets, which surrounding shaft surrounds a portion of the central shaft; and
using the surrounding shaft, engaging at least one of the leaflets with at least one leaflet-engaging element; and
after engaging, proximally withdrawing the distal end of the central shaft from within the ventricle.

In an embodiment, maintaining the central shaft in place and within the ventricle includes securing the distal end of the central shaft to tissue of the ventricle.

In an embodiment, engaging the at least one leaflet includes engaging exactly one leaflet.

There is further provided, in accordance with an embodiment of the present invention, apparatus, including:
at least one leaflet-engaging element;
a catheter; and
a delivery tool, which is advanceable within the catheter, and which includes a central shaft and a surrounding shaft that surrounds a portion of the central shaft and is slidable along the central shaft, a distal end of the central shaft configured to be advanced between leaflets of an atrioventricular valve of a patient and into a ventricle of the patient,
and the surrounding shaft is configured to engage at least one of the leaflets with the at least one leaflet-engaging element while the distal end of the central shaft is maintained in place and within the ventricle.

In an embodiment, the surrounding shaft is configured to engage the at least one of the leaflets by sliding with respect to the distal end of the central shaft.

In an embodiment, the surrounding shaft is configured to engage exactly one of the leaflets of the at least one leaflet-engaging element.

In an embodiment, the distal end of the central shaft is configured to be coupled to tissue of the ventricle at an intraventricular site.

There is yet further provided, in accordance with an embodiment of the present invention apparatus including:
a sheath, which is configured to be advanced into an atrium of a patient in a transcatheter procedure;
an implant assembly, which is configured to be passed through the sheath, and which includes:
at least one leaflet-engaging element;
a spool; and
at least one artificial chorda tendinea, which has opposite first and second end portions, which first end portion is coupled to the spool, and which second end portion is coupled to the at least one leaflet-engaging element; and
a delivery tool, which is configured to be passed through the sheath, and which includes:
a central shaft, which is configured to be advanced between leaflets of an atrioventricular valve of the patient and into a ventricle of the patient, and which is configured to be removably coupled to the spool, and to couple the spool at an intraventricular site of the ventricle;
a surrounding shaft, which surrounds a portion of the central shaft, and is slidable with respect to the central shaft; and
a coupling element holder, which is coupled to the surrounding shaft, and which is configured to couple the at least one leaflet-engaging element to at least one leaflet of the atrioventricular valve.

In an embodiment, the at least one artificial chorda tendinea and the spool are configured such that rotation of the spool winds the at least one artificial chorda tendinea around the spool, thereby drawing the at least one leaflet-engaging element toward the spool.

In an embodiment, the delivery tool further includes a torque-delivering tool, the central shaft is shaped to define at least one lumen, and the torque-delivering tool is disposed in the lumen and is configured to rotate the spool.

In an embodiment, the delivery tool further includes:
at least one guide wire coupled to the spool; and
a screwdriver housing, which is coupled to the central shaft in a vicinity of a distal end thereof, and which is configured to be removably coupled to the spool and advanceable along the guide wire.

In an embodiment, the at least one artificial chorda tendinea is configured such that a length thereof is adjustable from a site outside of a body of the patient.

In an embodiment,
the at least one artificial chorda tendinea includes first and second artificial chordae tendineae having respective first and second end portions,
the spool is coupled to the first end portions of the first and second artificial chordae tendineae, the at least one leaflet-engaging element includes first and second leaflet-engaging elements, which are coupled to the second end portion of the first artificial chorda tendinea and the second end portion of the second artificial chorda tendinea, respectively, and
the coupling element holder is configured to couple the first and second leaflet-engaging elements to respective first and second leaflets.

In an embodiment, the central shaft, while coupled to the spool, is configured to provide a reference force to the coupling element holder while the coupling element holder couples the at least one leaflet-engaging element to the at least one leaflet.

The present invention will be more fully understood from the following detailed description of embodiments thereof, taken together with the drawings, in which:

BRIEF DESCRIPTION OF THE DRAWINGS

FIGS. 4A-C are schematic illustrations of respective components of an adjusting mechanism of the spool assembly of FIG. 3, in accordance with an embodiment of the present invention;

FIGS. 9A-K are schematic illustrations of a system for implanting and adjusting repair chords, and a transcatheter procedure for implanting the chords in a heart, in accordance with an embodiment of the present invention;

FIGS. 14A-E are schematic illustrations of yet an additional system for implanting and adjusting repair chords, and a transcatheter procedure for implanting the chords in a heart, in accordance with an embodiment of the present invention;

FIGS. 17A-G are schematic illustrations of still another system for implanting and adjusting repair chords, and a transcatheter procedure for implanting the chords in a heart, in accordance with an embodiment of the present invention;

FIGS. 19, 20A-B, and 21 are schematic illustrations of the repair chords used to draw portions of a ventricular wall toward one another, in accordance with an embodiment of the present invention;

DETAILED DESCRIPTION OF THE INVENTION

Figure 1:
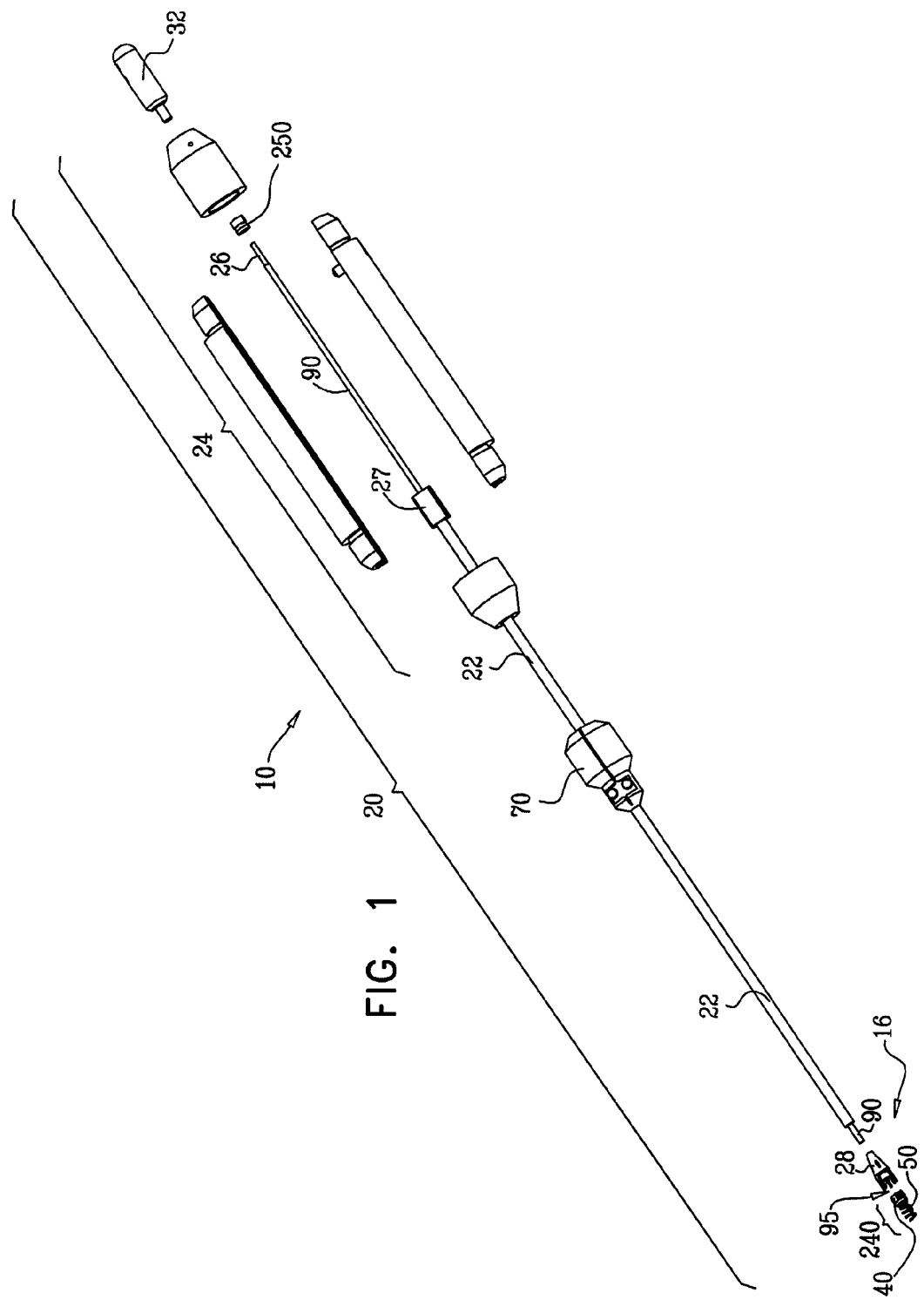
FIG. 1 is a schematic illustration of respective portions of a delivery tool system for implanting and adjusting repair chords, in accordance with an embodiment of the present invention.
Figure 2:
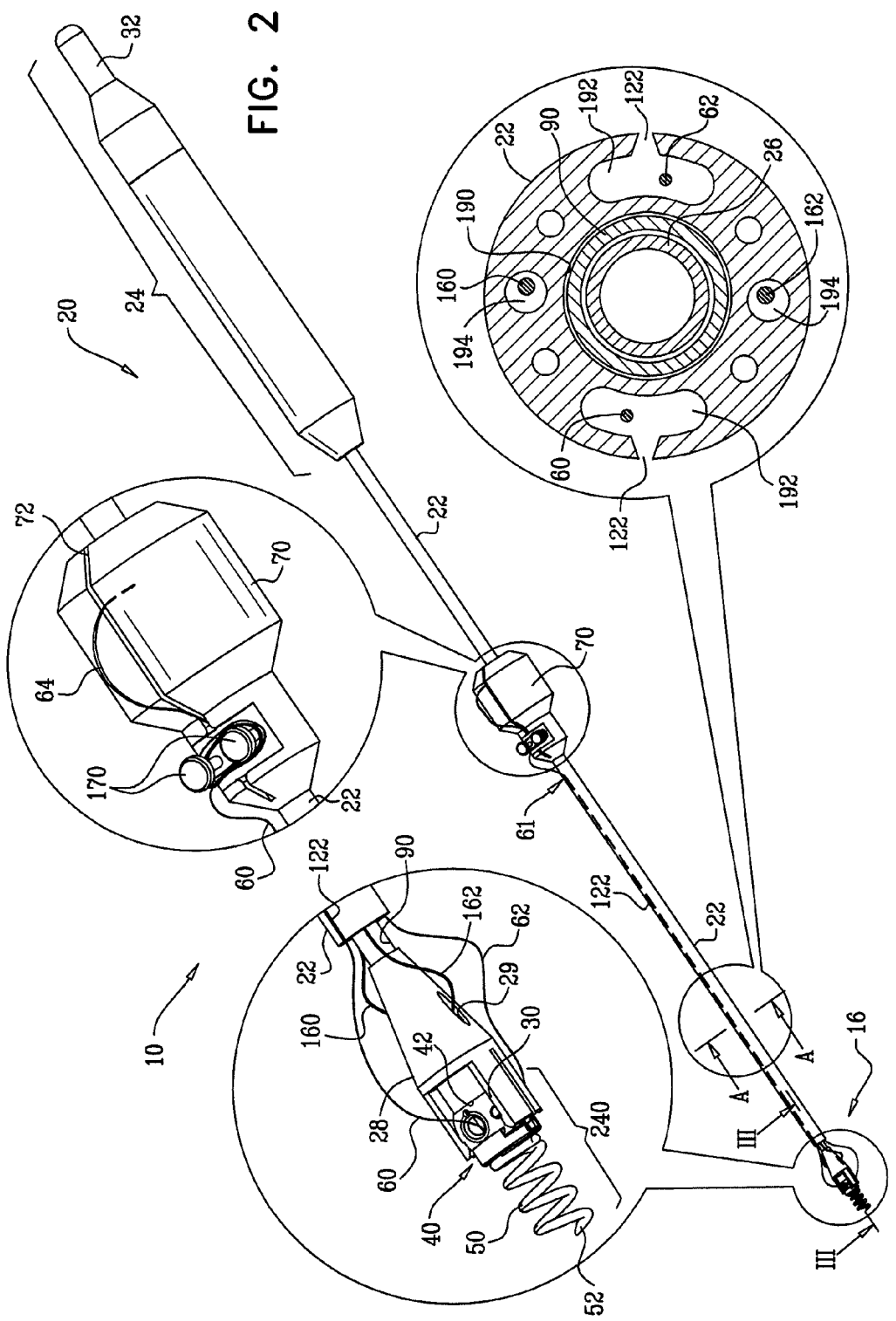
FIG. 2 is a schematic illustration of the delivery tool system of FIG. 1, in accordance with an embodiment of the present invention.

Reference is now made to FIGS. 1-2, which are schematic illustrations of a system 10 comprising apparatus for implanting and adjusting repair chords in a heart of a patient, in accordance with an embodiment of the present invention. FIG. 1 is a schematic illustration of a portion of the respective components of system 10 showing the relationship between the components. System 10 comprises a delivery tool 20 having a proximal handle portion 24 and an elongate multi-lumen shaft 22. System 10 further comprises an implant assembly 16, which comprises a spool assembly 240 that is reversibly couplable to a distal portion of delivery tool 20. Spool assembly 240 comprises an adjusting mechanism 40 that is coupled to a tissue anchor 50. Tissue anchor 50 is shown as a helical anchor by way of illustration and not limitation, and may comprise staples, clips, spring-loaded anchors, or other tissue anchors known in the art. Alternatively, spool assembly 240 does not include tissue anchor 50 and is, instead, sutured to a portion of tissue of a ventricle wall which faces a ventricular lumen of a heart of a patient.

Shaft 22 comprises a multilumen shaft defining a primary lumen surrounding a torque-delivering tool 26 which is surrounded by an overtube 90 (as shown in the transverse cross-section of tool 22 in FIG. 2). Torque-delivering tool 26 is coupled at a proximal end thereof to a rotating structure 32 that is coupled to handle 24 and, in response to rotation thereof, functions to deliver torque to torque-delivering tool 26. Torque-delivering tool 26 rotates in response to rotation of rotating structure 32 and delivers torque to adjusting mechanism 40 coupled to the distal end of tool 20.

(In this context, in the specification and in the claims, "proximal" means closer to the orifice through which tool 20 is originally placed into the body of the subject, and "distal" means further from this orifice.)

FIG. 2 shows delivery tool 20 in its assembled state. Implant assembly 16 comprises longitudinal members 60 and 62 which function as the repair chords that are ultimately implanted in the heart of the patient. Respective first end portions of longitudinal members 60 and 62 are coupled to a spool that is housed within a spool housing 42 of spool assembly 240. Thus, implant assembly 16 comprises spool assembly 240 and longitudinal members 60 and 62. Each longitudinal member 60 and 62 has a free end that is coupled to a respective suture needle 64. The pointed tips of each needle 64 are disposed within a respective slit 72 of a needle holder 70. Each longitudinal member 60 and 62 extends from its first portions thereof, through a respective secondary lumen 192 of multilumen shaft 22 (as shown in the transverse cross-section of shaft 22) toward needle holder 70. Needle holder 70 is shaped to provide knobs 170 for looping portions of each longitudinal member 60 and 62 therearound. During delivery of spool assembly 240 to the implantation site in the ventricle of the patient, portions of longitudinal members 60 and 62 are wound around knobs 170 of needle holder 70 and needles 64 are disposed within slits 72 of needle holder 70 so as to facilitate atraumatic delivery of spool assembly 240 to the implantation site. During the implantation of longitudinal members 60 and 62 in the heart of the patient, needles 64 are extracted from slits 72, and longitudinal members 60 and 62 are unwound from knobs 170. Unwinding longitudinal members 60 and 62 extends longitudinal members 60 and 62 and provides the operating physician with enough slack to suture respective portions of longitudinal members 60 and 62 to heart tissue (e.g., a valve leaflet or a portion of the ventricle wall) that faces and surrounds the ventricular lumen of the heart.

Typically, longitudinal members 60 and 62 comprise a flexible and/or superelastic material, e.g., ePTFE, nitinol, PTFE, polyester, stainless steel, or cobalt chrome. In some embodiments, longitudinal members 60 and 62 are coated with polytetrafluoroethylene (PTFE) or with PTFE. In some embodiments, longitudinal members 60 and 62 comprise at least one wire/suture portion and at least one portion that comprises an elongate tensioning coil. For example, longitudinal members 60 and 62 may comprise an elongate coil between two wire/suture portions.

For some applications, following initial implantation, the length of longitudinal members 60 and 62 are adjusted (either shortened or lengthened) from a site outside the patient's body. For example, the length may be adjusted by applying RF or ultrasound energy to the members.

Shaft 22 defines longitudinal slits 122 that run parallel with respect to a longitudinal axis of tool 20. Once longitudinal members 60 and 62 are unwound from knobs 170, they are pulled from within lumens 192, via slits 122, and away from the longitudinal axis of tool 20 in order to release longitudinal members 60 and 62 from within shaft 22.

A distal portion of delivery tool 20 comprises a screwdriver housing 28 which houses a screwdriver tool, as is described hereinbelow. Housing 28 is shaped to define graspers 30 which reversibly grasp housing 42 of adjusting mechanism 40 of spool assembly 240. Graspers 30 have a tendency to compress toward one another, and thus are clamped around housing 42. As shown in the enlarged distal portion of tool 22, longitudinal members 60 and 62 of implant assembly 16 emerge from within housing 42. The spool disposed within housing 42 is not shown for clarity of illustration; however, it is to be noted that respective portions of longitudinal members 60 and 62 are coupled to the spool. One or more (e.g., a pair, as shown) of guide wires 160 and 162 are (1) coupled at respective first ends thereof to housing 42 and extend (2) through respective proximal openings 29 in screwdriver housing 28, (3) through respective secondary lumens 194 of multilumen shaft 22 (as shown in the transverse cross-section of shaft 22), and (4) are coupled at respective second ends thereof to handle portion 24. In these applications, following implantation and adjustment of the repair chords, as described hereinbelow, guide wires 160 and 162 may be cut and pulled away from housing 42. For some applications, guide wires 160 and 162 are reversibly coupled to housing 42 by being looped through a portion of the housing. In these applications, following implantation and adjustment of the repair chords, as described hereinbelow, guide wires 160 and 162 may be pulled away from housing 42.

Figure 3:
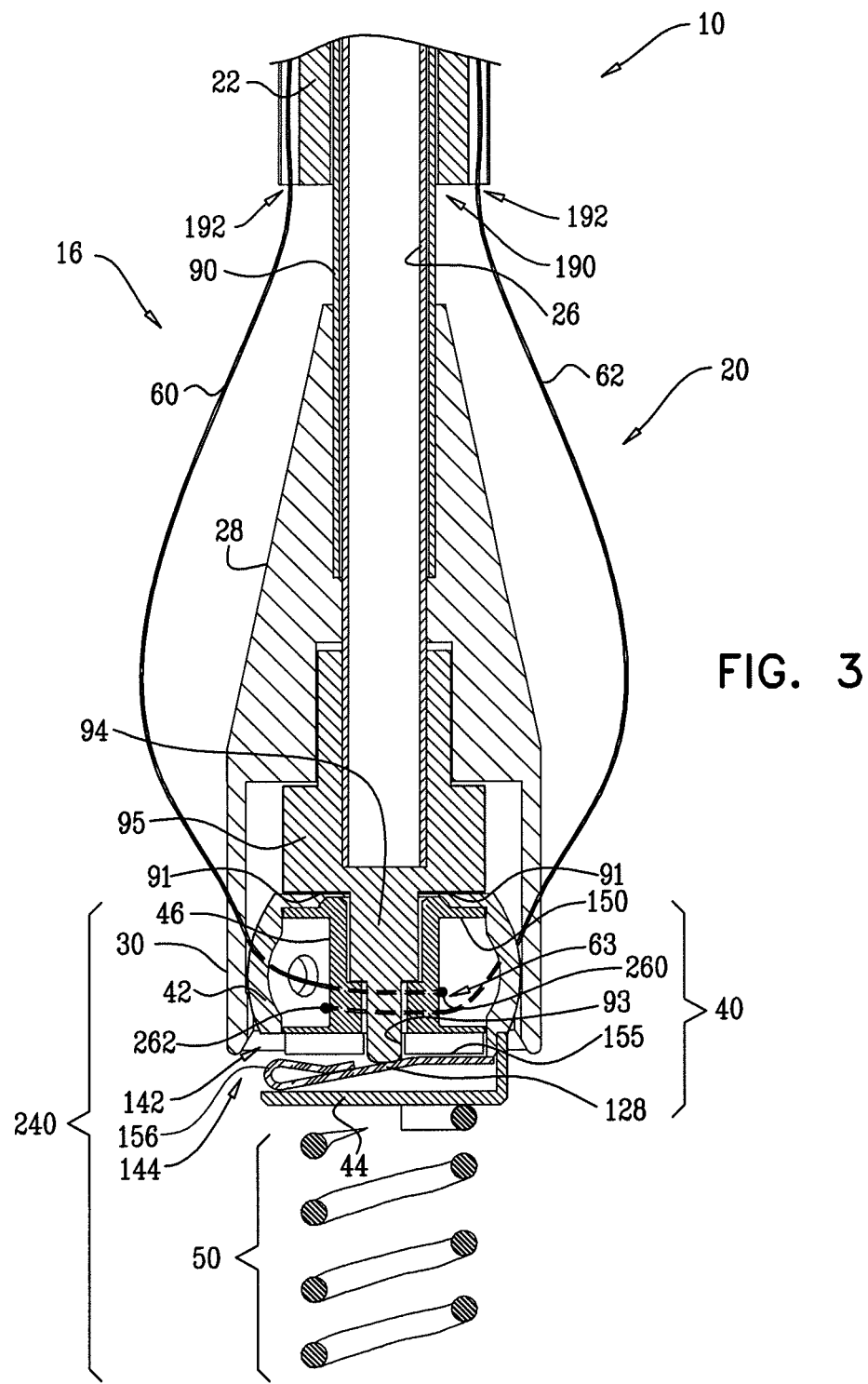
FIG. 3 is a schematic illustration of a spool assembly coupled to a distal end of the delivery tool of FIG. 1, in accordance with an embodiment of the present invention.

FIG. 3 shows a cross-sectional image of a distal portion of tool 20 and spool assembly 240 that is coupled to delivery tool 20 via graspers 30 of screwdriver housing 28, in accordance with an embodiment of the present invention. Spool assembly 240 comprises an adjusting mechanism 40 that is coupled to, e.g., welded to, a helical tissue anchor 50. Adjusting mechanism 40 comprises a housing 42 which houses a rotatable structure, or a spool 46. Spool 46 has a cylindrical body that is disposed in parallel with respect to the longitudinal axis of tool 20 by way of illustration and not limitation. Respective portions 63 of longitudinal members 60 and 62 are coupled to (e.g., welded to, knotted to, looped within, or otherwise fastened to) spool 46 at coupling sites 260 and 262, respectively.

Longitudinal members 60 and 62 extend externally to screwdriver housing 28 and through respective secondary lumens 192 of multilumen shaft 22. It is to be noted that although two longitudinal members 60 and 62 are shown as being coupled to spool 46, any suitable number of longitudinal members may be coupled to spool 46. In some embodiments, only one longitudinal member is coupled at a first end thereof to spool 46, and the second end of the longitudinal member is configured to be attached to heart tissue, e.g., a leaflet of an atrioventricular valve or a portion of the ventricular wall. In some embodiments, the atrioventricular valve includes a mitral valve of the patient. In some embodiments, the atrioventricular valve includes a tricuspid valve of the patient. For some applications, the one longitudinal member may be looped within spool 46 in a manner in which a middle portion thereof is looped within the spool and respective portions thereof extend from spool 46 along shaft 22 in their respective lumens 192. In such an embodiment, the one longitudinal member defines two free ends which are coupled to suture needles and are ultimately attached to, e.g., sutured to, heart tissue.

A distal end of shaft 22 is disposed proximally to a proximal end of screwdriver housing 28. As described hereinabove, torque-delivering tool 26 and overtube 90 that surrounds torque-delivering tool 26 are disposed within primary lumen 190 of shaft 22. Screwdriver housing 28 is shaped to define a primary lumen which receives a distal portion of torque-delivering tool 26 and a distal portion of overtube 90. During delivery of spool assembly 240 to the implantation site in the ventricle, a distal end of overtube 90 is disposed within housing 28 proximally to a distal end of torque-delivering tool 26. A distal portion of torque-delivering tool 26 is disposed within a screwdriver head 95 that is disposed within housing 28. Screwdriver head 95 defined a recess for receiving the distal portion of torque-delivering tool 26. Screwdriver head 95 is shaped to provide a spool-rotating portion 94 which fits within a channel defined by spool 46. Spool-rotating portion 94 is shaped in accordance with the shape of the channel defined by spool 46 such that rotation of torque-delivering tool 26 delivers torque to and rotates screwdriver head 95. In response to the rotation of screwdriver head 95, spool-rotating portion 94 pushes against the wall of spool 46 that defines the channel extending therethrough, and responsively, spool 46 is rotated.

Reference is now made to both FIGS. 2 and 3. As shown in FIG. 2, guide wires 160 and 162 extend from spool housing 42 and through openings 29 defined in screwdriver housing 28. Since guide wires 160 and 162 are disposed within lumens of multilumen shaft 22 that are orthogonal with respect to lumens 192 (which surround longitudinal members 60 and 62), guide wires 160 and 162 are not shown in FIG. 3. Similarly, the openings 29 of screwdriver housing 28 are not shown in FIG. 3. It is to be noted that screwdriver housing is shaped to define a respective secondary lumen which surrounds each guide wire 160 and 162 and extend from spool housing 42 toward each proximal opening 29 in screwdriver housing 28. These secondary lumens run in parallel with respect to the primary lumen defined by housing 28 that surrounds torque-delivering tool 26 and overtube 90.

Figure 4A:
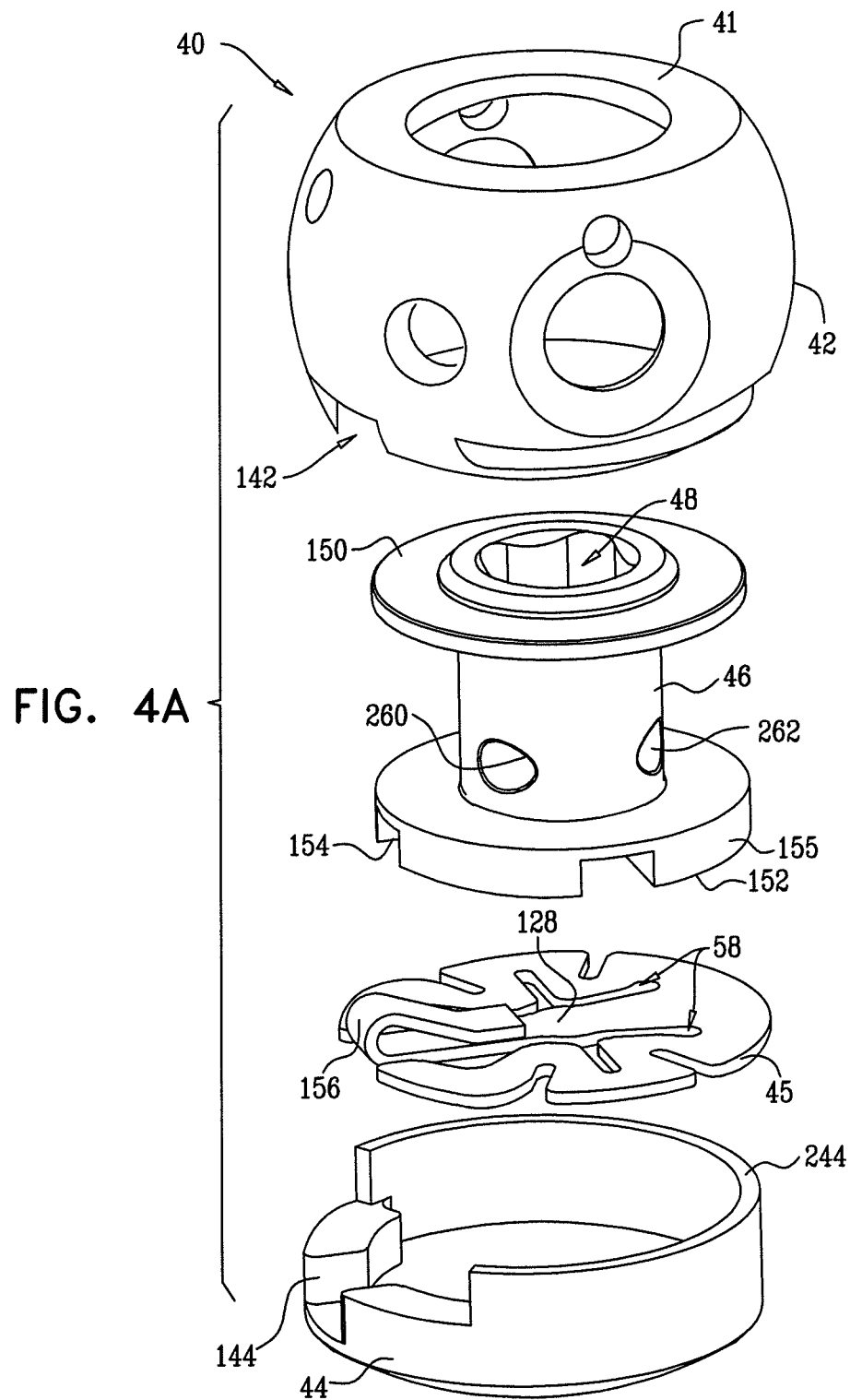

FIG. 4A shows a relationship among individual components of adjusting mechanism 40, in accordance with an embodiment of the present invention. Adjusting mechanism 40 is shown as comprising spool housing 42 which defines an upper surface 41 and a recessed portion 142. Spool 46 is configured to be disposed within housing 42 and defines an upper surface 150, a lower surface 152 and a cylindrical body portion disposed vertically between surfaces 150 and 152. Spool 46 is shaped to provide a driving interface, e.g., a channel 48, which extends from an opening provided by upper surface 150 to an opening provided by lower surface 152. Channel 48 of the driving interface is shaped to define a hexagonal channel or a channel having another shape. The cylindrical body portion of spool 46 is shaped to define holes 260 and 262 which function as respective coupling sites for coupling longitudinal members 60 and 62 to spool 46. In some embodiments, system 10 described herein comprises only one longitudinal member which is looped through spool 46 via holes 260 and 262.

Coupling sites 260 and 262 may be shaped to define holes, as shown, or slits through which respective portions of longitudinal members 60 and 62 are looped therethrough. In some embodiments, respective portions of longitudinal members 60 and 62 are looped through coupling sites 260 and 262 such that their ends are disposed within channel 48 of spool 46. The ends of longitudinal members 60 and 62 are knotted within channel 48 so as to fix the ends within channel 48 and prevent their release from spool 46. In some embodiments, coupling sites 260 and 262 are shaped to define male projections, e.g., knobs or hooks, around which respective portions of longitudinal members 60 and 62 are ensnared or looped and thereby coupled to spool 46.

Lower surface 152 of spool 46 is shaped to define one or more (e.g., a plurality, as shown) recesses 154 which define structural barrier portions 155 of lower surface 152. It is to be noted that any suitable number of recesses 154 may be provided, e.g., between 1 and 10 recesses, circumferentially with respect to lower surface 152 of spool 46.

A locking mechanism 45 is coupled to lower surface 152 and is coupled, e.g., welded, at least in part to a lower surface of spool housing 42. Typically, locking mechanism 45 defines a mechanical element having a planar surface that defines slits 58. It is to be noted that the surface of locking mechanism 45 may also be curved, and not planar. Locking mechanism 45 is shaped to provide a protrusion 156 which projects out of a plane defined by the planar surface of the mechanical element. Slits 58 define a depressible portion 128 of locking mechanism 45 that is disposed in communication with and extends toward protrusion 156. Depressible portion 128 is moveable in response to a force applied thereto typically by screwdriver head 95, as shown in detail hereinbelow with reference to FIGS. 4B-C.

It is to be noted that the planar, mechanical element of locking mechanism 45 is shown by way of illustration and not limitation and that any suitable mechanical element having or lacking a planar surface but shaped to define at least one protrusion may be used together with locking mechanism 45.

A cap 44 is provided that is shaped to define a planar surface and an annular wall having an upper surface 244 thereof. Upper surface 244 of the annular wall is coupled to, e.g., welded to, a lower surface provided by spool housing 42. The annular wall of cap 44 is shaped to define a recessed portion 144 of cap 44 that is in alignment with recessed portion 142 of spool housing 42.

Reference is now made to FIGS. 4B-C, which are schematic illustrations of adjusting mechanism 40 in respective locking states thereof, in accordance with an embodiment of the present invention. It is to be noted that longitudinal members 60 and 62 that are typically coupled to spool 46, are not shown for clarity of illustration. FIG. 4B shows adjusting mechanism 40 in an unlocked configuration in which protrusion 156 of locking mechanism 45 is disposed within recessed portion 144 of cap 44. FIG. 4C shows the locked state of spool 46 by the positioning of protrusion 156 within a recess 154 of spool 46.

Reference is again made to FIGS. 3 and 4B-C. FIG. 4B shows adjusting mechanism 40 in an unlocked state thereof, as shown in FIG. 3. During (1) the delivery of spool assembly 240 to the implantation site in a first portion of tissue defining the ventricular lumen of the patient, (2) the attachment of the longitudinal members to a second portion of heart tissue that faces surrounds the ventricular lumen of the patient, and (3) the subsequent rotation of spool 46 to adjust a length between the first and second portions of heart tissue, adjusting mechanism 40 is disposed in an unlocked state, as shown in FIGS. 3 and 4B. As shown in FIG. 4C, spool 46 is shaped to provide a first opening 180 at upper surface 150 thereof and a second opening 182 at a lower surface 152 thereof. Spool 46 defines a channel 48 that extends from first opening 180 toward second opening 182.

FIGS. 3 and 4B show adjusting mechanism 40 in an unlocked state thereof in which screwdriver head 95 is disposed within channel 48 of spool 46. Screwdriver head 95 comprises an elongate body shaped to define a proximal generally cylindrical structure and spool-rotating portion 94 which fits within channel 48 defined by spool 46. Spool-rotating portion 94 is shaped to define a distal force applicator 93 which is disposed proximally to and in communication with depressible portion 128 of locking mechanism 45. In the unlocked state of adjusting mechanism 40, screwdriver head 95 is disposed with respect to housing 42 in a manner in which a distal end of force applicator 93 extends beyond second opening 182 of spool 46 and pushes against depressible portion 128 of locking mechanism 45. Depressible portion 128 is thus pushed downward, as shown.

Channel 48 of spool 46 is shaped to accommodate the dimensions of spool-rotating portion 94 and force application 93 of screwdriver head 95. Spool-rotating portion 94 has a width that is wider than the force applicator 93. In turn, channel 48 of spool 46 is shaped to accommodate spool-rotating portion 94 and force application 93 defining an upper portion and a lower portion thereof in which the upper portion of channel 48 is wider than the lower portion. The narrower lower portion of channel 48 ensures that force applicator 93 is not advanced distally beyond a certain point as the narrower lower portion of channel 48 restricts passage therethrough of the upper, wider portion of spool-rotating portion 94. Screwdriver head 95 is shaped to define a shelf portion 91 which rests against upper surface 41 of spool housing 42. Similarly, spool-rotating portion 94 is shaped to define a shelf portion 143 which rests against a horizontal wall of spool 46 which defines a portion of channel 48. During the unlocked state of adjusting mechanism 40, screwdriver head 95 is disposed in a manner in which shelf portion 91 thereof rests against upper surface 41 of spool housing 42, and shelf 143 of spool-rotating portion 94 rests against the horizontal wall of channel 48, as shown.

During the unlocked state of adjusting mechanism 40, depressible portion 128 is maintained in a pushed state by force applicator 93. In such a state, protrusion 156 of locking mechanism 45 is maintained in a pushed state toward the planar surface of cap 44. It is to be noted that the surface of cap 44 may also be curved, and not planar. As described hereinabove, cap 44 is shaped to provide a recessed portion 144 for receiving protrusion 156 in its pushed-down state. As depressible portion 128 is pushed downward, protrusion 156 is freed from within a recess 154 defined by structural barrier portions 155 of the lower portion of spool 46. Additionally, protrusion 156 is freed from within recessed portion 142 provided by spool housing 42. Responsively, adjusting mechanism 40 is unlocked, and spool 46 may be rotated by screwdriver head 95 in either clockwise or counter-clockwise directions in response to torque delivered to head 95 by torque-delivering tool 26 coupled thereto. In response to the torque, spool-rotating portion 94 of screwdriver head 95 engages and pushes against the wall defining channel 48 in order to rotate spool 46.

Cap 44 functions to restrict distal pushing of depressible portion 128 beyond a desired distance so as to inhibit deformation of locking mechanism 45. Once adjustment mechanism 40 is implanted in heart tissue, cap 44 also provides an interface between adjusting mechanism 40 and the heart tissue. This prevents interference of heart tissue on adjusting mechanism 40 during the locking and unlocking thereof. Additionally, cap 44 prevents damage to heart tissue by depressible portion 128 as it is pushed downward.

FIG. 4C shows adjusting mechanism 40 in a locked state thereof in which locking mechanism 45 is shown in a resting state thereof. In the resting state of locking mechanism 45, depressible portion 128 is disposed in a horizontal position (i.e., perpendicularly with respect to a longitudinal axis of channel 48) in response to removal of screwdriver head 95 from within channel 48 of spool 46. Depressible portion 128 has a tendency to assume the horizontal position, as shown, and in the absence of a downward pushing force applied to depressible portion 128 by screwdriver head 95, depressible portion 128 returns to its horizontal position from its pushed-down state, as shown in FIG. 4B. In this horizontal position, protrusion 156 of locking mechanism 45 is removed from recessed portion 144 of cap 44 and is returned within a recess 154 of spool 46 and thereby restricts movement of spool 46 and locks adjusting mechanism 40. Additionally, protrusion 156 of locking mechanism 45 returns in part within recessed portion 142 of spool housing 42. Thus, recessed portion 142 of spool housing 42 provides supplemental locking of locking mechanism 45.

Figure 5A:
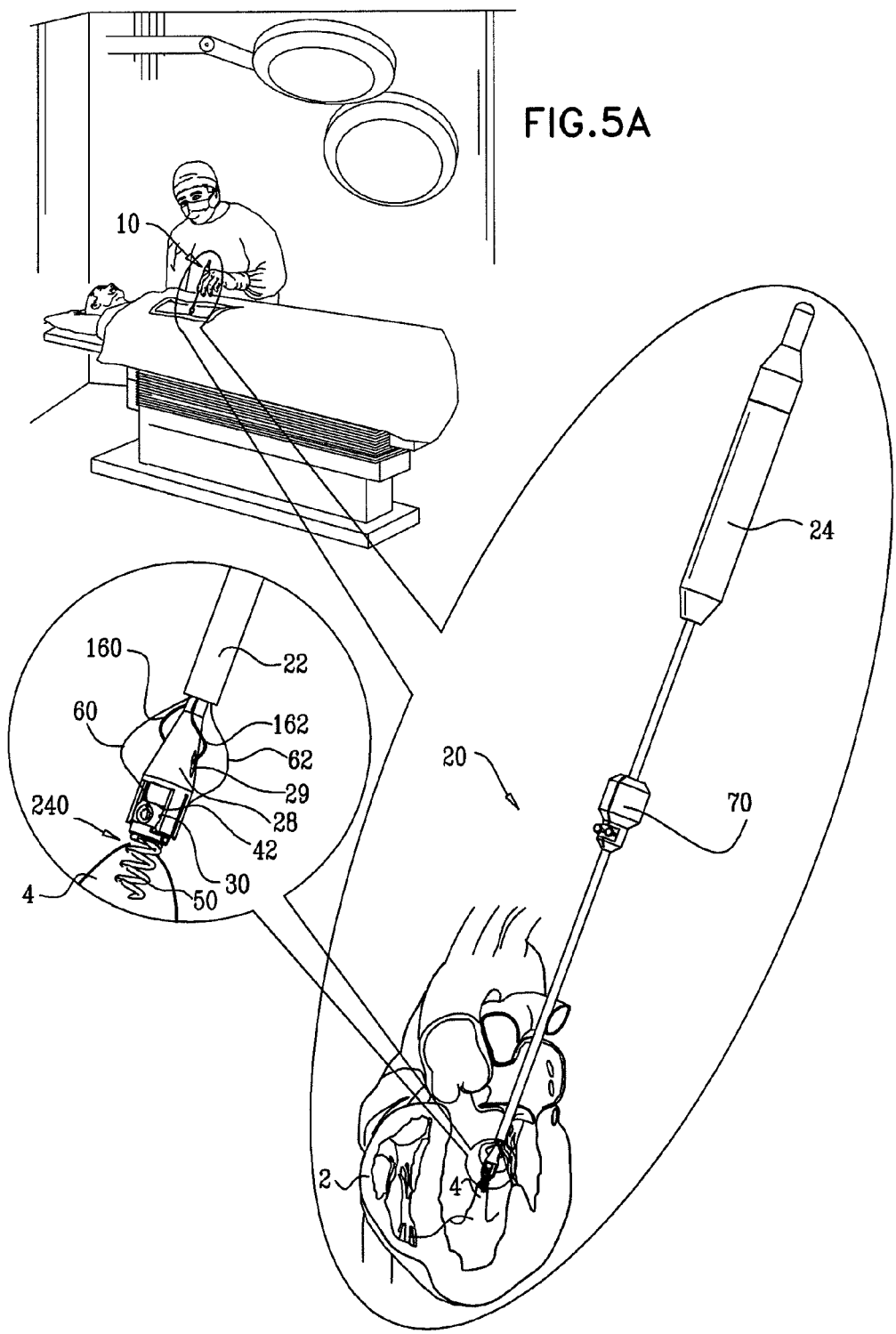
FIGS. 5A-G are schematic illustrations of a procedure for using the delivery tool to implant the spool assembly at a papillary muscle and adjust the repair chords, in accordance with an embodiment of the present invention.

Reference is now made to FIGS. 5A-G, which are schematic illustrations of a method for implantation of spool assembly 240 and longitudinal members 60 and 62 of system 10 in the heart of the patient, in accordance with an embodiment of the present invention. FIG. 5A shows an open heart procedure in which an operating physician positioning tool 20 in a heart 2 of a patient and implanting spool assembly 240 in tissue of a papillary muscle 4 of the left ventricle of heart 2. FIG. 5A shows the general relative perspective of tool 20 with respect to heart 2. It is to be noted that FIGS. 5A-G are not drawn to scale in order to illustrate clearly the function of tool 20 in heart 2.

Figure 5B:
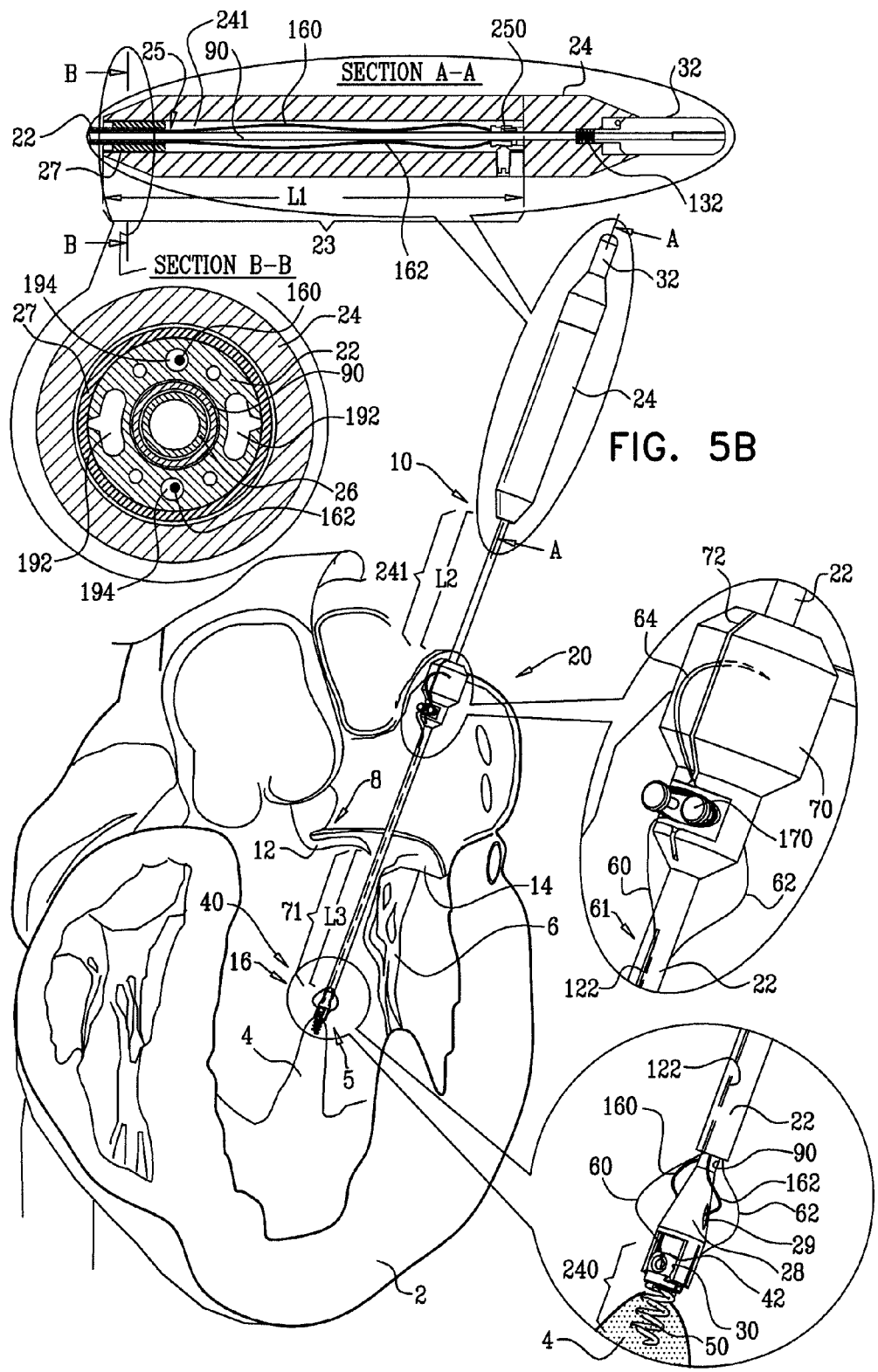

FIG. 5B shows a distal portion of tool 20 disposed within the left ventricle of heart 2. The operating physician advances a distal portion 71 of tool 20 between leaflets 12 and 14 of a mitral valve 8. Tool 20 is disposed with respect to heart 2 in a manner in which needle holder 70 is disposed outside of heart 2. As shown in the enlarged portion of needle holder 70, needle 64 of longitudinal member 60 is disposed within slit 72 of needle holder 70. Additionally, longitudinal member 60 is looped around knobs 170 of needle holder 70 such that knobs 170 gather excess portions of longitudinal member 60. Longitudinal member 60 emerges from within slit 122 defined by multilumen shaft 22 at a proximal opening 61 of slit 122. Longitudinal member 62 is also shown as emerging from within its respective slit in shaft 22. The needle coupled to longitudinal member 62 is also housed within a slit provided by needle holder 70 (needle not shown for clarity of illustration).

Delivery tool 20 is rotated in order to screw helical anchor 50 of spool assembly 240 into tissue of papillary muscle 4 at an intraventricular implantation site 5. Spool assembly 240 is coupled to cardiac tissue in a manner in which spool housing 42 and spool 46 are disposed within the ventricular lumen at the intraventricular implantation site. Tissue anchor 50 is screwed into the cardiac tissue in a manner in which it is disposed fully within the heart tissue, e.g., papillary muscle, endocardium, or myocardium, and does not extend beyond a pericardium of the heart. Papillary muscle 4 includes a portion of cardiac tissue which faces and surrounds the left ventricular lumen of heart 2. In response to rotation of tool 20, spool assembly 240 is implanted at a first implantation site 5. In the enlarged view of the distal portion of tool 20 and spool assembly 240, longitudinal members 60 and 62 (coupled to spool 46) and guide wires 160 and 162 (coupled to housing 42) are shown as emerging from housing 42 and are fed within their secondary respective lumens of multilumen shaft 22.

Guide wires 160 and 162 extend within their respective lumens 194 of shaft 22 and toward handle 24. Handle 24 is shaped to provide a handle lumen 23 thereof, as shown in the enlarged longitudinal cross-sectional image of handle 24 (section A-A). A guide wire grasper 250 is disposed within lumen 23 and is coupled to the proximal ends of each guide wire 160 and 162. Handle lumen 23 has a handle-lumen-length L1 of between 50 mm and 100 mm, e.g., 70 mm. A proximal end 25 of multilumen shaft 22 is disposed at a distal portion of lumen 23.

A proximal portion 241 of multilumen shaft 22 (i.e., the portion of shaft 22 that is disposed immediately distal to proximal end 25 of shaft 22) is configured to slide within lumen 23. Proximal portion 241 of shaft 22 slides within lumen 23 when the operating physician grasps shaft 22 and slides shaft 22 proximally. Proximal portion 241 of shaft 22 also has a shaft-length L2 such that proximal portion 241 fits within handle lumen 23, as is described hereinbelow. A guide 27 is coupled to proximal end 25 of shaft 22 and is advanced proximally within lumen 23 in response to proximal sliding of portion 241 of shaft 22 within lumen 23. Ultimately, in response to the sliding of proximal portion 241 of shaft 22 within lumen 23 of handle 24, distal portion 71 of shaft 22 slides proximally with respect to overtube 90 such that distal portion 71 is disposed entirely within the left atrium of the patient, i.e., not within the left ventricle (as shown in FIG. 5D).

As shown, following the proximal sliding of shaft 22, needle holder 70 is positioned proximally and adjacently to the distal end of handle 24.

Section B-B shows a transverse cross-section of delivery tool 22 at a distal portion of handle 24. Section B-B shows handle 24 which surrounds guide 27. Guide 27, in turn, surrounds a proximal end of multilumen shaft 22. Torque-delivering tool 26 surrounded by overtube 90 are disposed within the primary lumen of shaft 22. As shown, guide members 160 and 162 are disposed within secondary lumens 194 of shaft 22. Secondary lumens 192 (which house longitudinal members 60 and 62 at the portion of tool between needle holder 70 and the distal end of shaft 22) are empty at handle 24 because longitudinal members 60 and 62 exit lumens 192 distally to needle holder 70.

As shown in Section A-A, handle 24 comprises a torque facilitator (e.g., a spring) 132 that is coupled to and surrounds a proximal portion of torque-delivering tool 26. Torque-delivering tool 26 extends proximally within handle 24 to rotating structure 32 at the proximal end of handle 24.

Figure 5C:
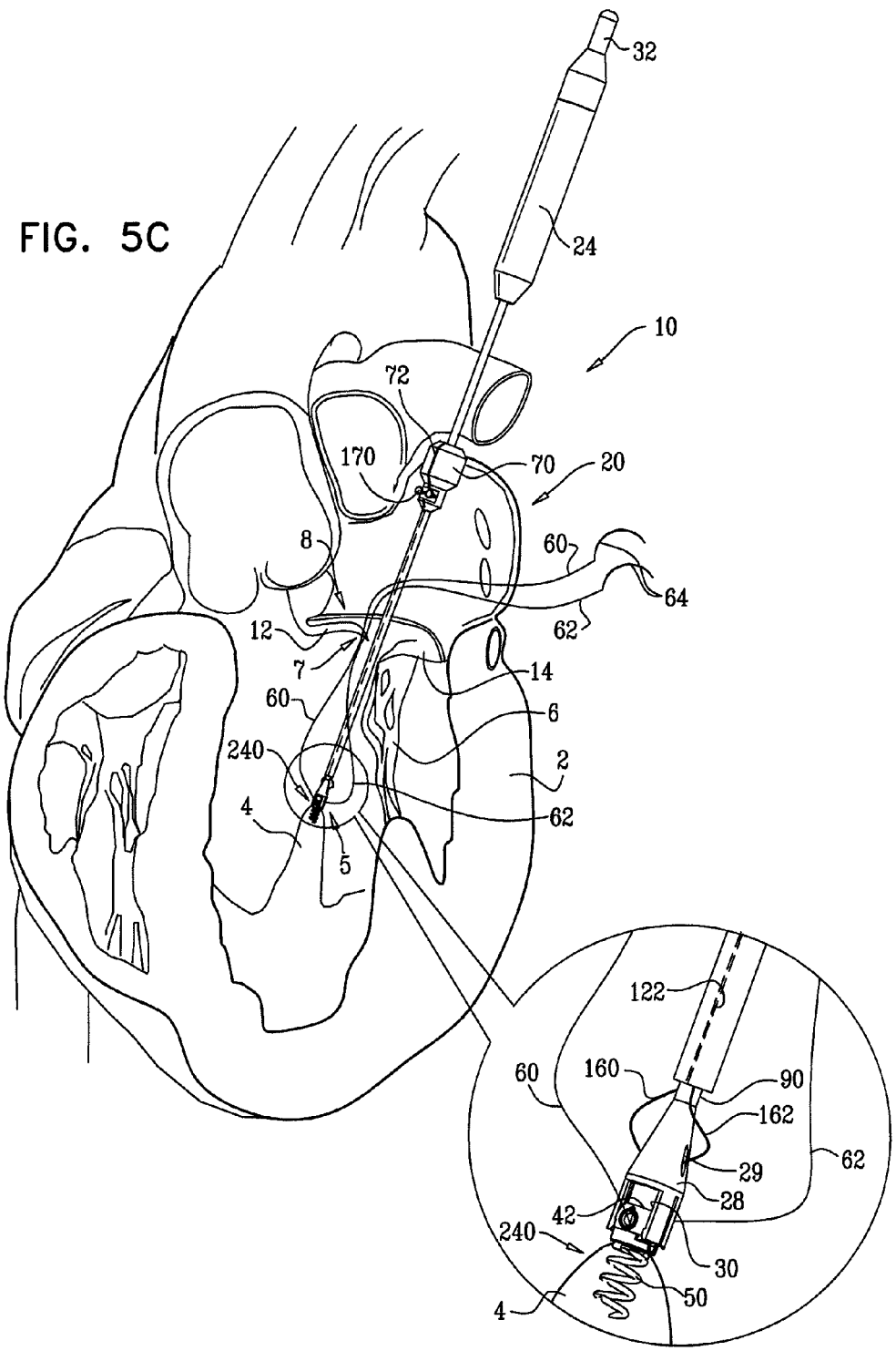
Figure 5D:
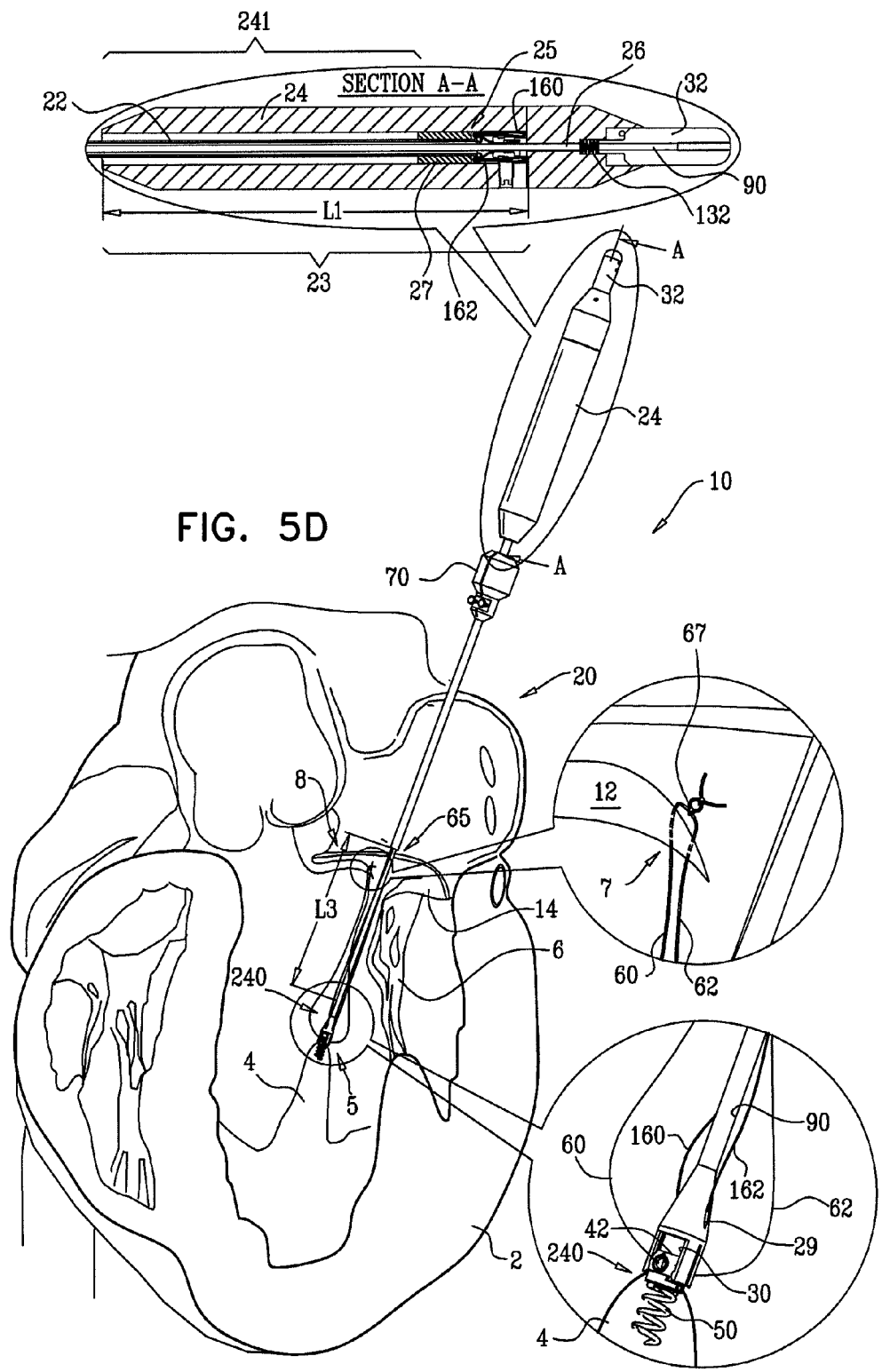

FIG. 5C shows the extracting of longitudinal members 60 and 62 from within their respective lumens 192 of shaft 22. Needles 64 are pulled from within slits 72 of needle holder 70. Then, longitudinal members 60 and 62 are unwound from knobs 170 of needle holder 70 and pulled away from the longitudinal axis of shaft 22 along slits 122 of shaft 22. Following the extracting of longitudinal members 60 and 62 from their respective lumens 192, needles 64 are held outside heart 2 so as not to puncture tissue of the heart. The free ends of longitudinal members 60 and 62, which are coupled to needles 64 are then sutured to leaflet 12 at a second implantation site 7 at a portion of heart tissue which faces and surrounds the ventricular lumen of heart 2.

FIG. 5D shows longitudinal members 60 and 62 coupled to leaflet 12 at second implantation site 7. Longitudinal members 60 and 62 are knotted together using suture knots 67, and excess portions of longitudinal members 60 and 62 are cut away from knot 67. It is to be noted that although knot 67 is used to couple longitudinal members 60 and 62 to leaflet 12, any suitable anchor may be used. For example, longitudinal member 60 may comprise a male clip at its free end and longitudinal member 62 may comprise a female clip at its free end. In such an embodiment, longitudinal members 60 and 62 are clipped at their free ends to leaflet 12.

Following the coupling of longitudinal members 60 and 62 to leaflet 12, shaft 22 is slid proximally to expose a portion of overtube 90 and torque-delivering tool 26. During the proximal sliding of shaft 22, proximal portion 241 of shaft 22 is slid within lumen 23 of handle 24. Handle-lumen-length L1 of lumen 23 of handle 24 is long enough to accommodate shaft-length L2 of proximal portion 241 of shaft 22. In response to the sliding of shaft 22, the distal portion of the exposed overtube 90 and torque-delivering tool 26 defines a torque-delivering tool length L3 at a distal portion thereof that is equal to shaft-length L2 of proximal portion 241 of shaft 22. Thus, handle-lumen-length L1, shaft-length L2 at proximal portion 241 of shaft 22, and torque-delivering tool length L3 at the distal portion thereof are equal and have a ratio of between 0.7:1 and 1.3:1.

Shaft-length L2 of proximal portion 241 of shaft 22 is such that when portion 241 slides within lumen 23 of handle 24 as shaft 22 is slid proximally along overtube 90, a distal-most end 65 of shaft 22 is disposed proximally to mitral valve 8 (i.e. distal-most end 65 of shaft 22 is disposed in the left atrium of heart 2). Typically, multilumen shaft 22 has a diameter of between 1.5 mm and 4 mm, typically, 3 mm, and overtube 90 has a diameter of between 0.8 mm and 1.5 mm, typically, 1.5 mm. Sliding of shaft 22 to position distal-most end 65 of shaft 22 in the left atrium, thus reduces the diameter of tool 20 between leaflets 12 and 14 of valve 8.

Following the sliding, the incision is closed around tool 20 using a purse string stitch, for example. The patient is removed from the cardiopulmonary bypass pump and heart 2 is allowed to resume its normal function. While heart 2 is beating, spool 46 of adjustment mechanism 40 may then be rotated in order to adjust a length of longitudinal members 60 and 62, and responsively, a distance between first and second implantation sites 5 and 7 is adjusted. The adjustment of longitudinal members is typically performed with the aid of imaging, such as fluoroscopy, transesophageal echo, and/or echocardiography.

Sliding of shaft 22 thus reduces the diameter of the portion of tool 20 that is disposed between leaflets 12 and 14, and thus, reduces interference of tool 20 on the beating of valve 8 as longitudinal members 60 and 62 are adjusted.

Figure 5E:
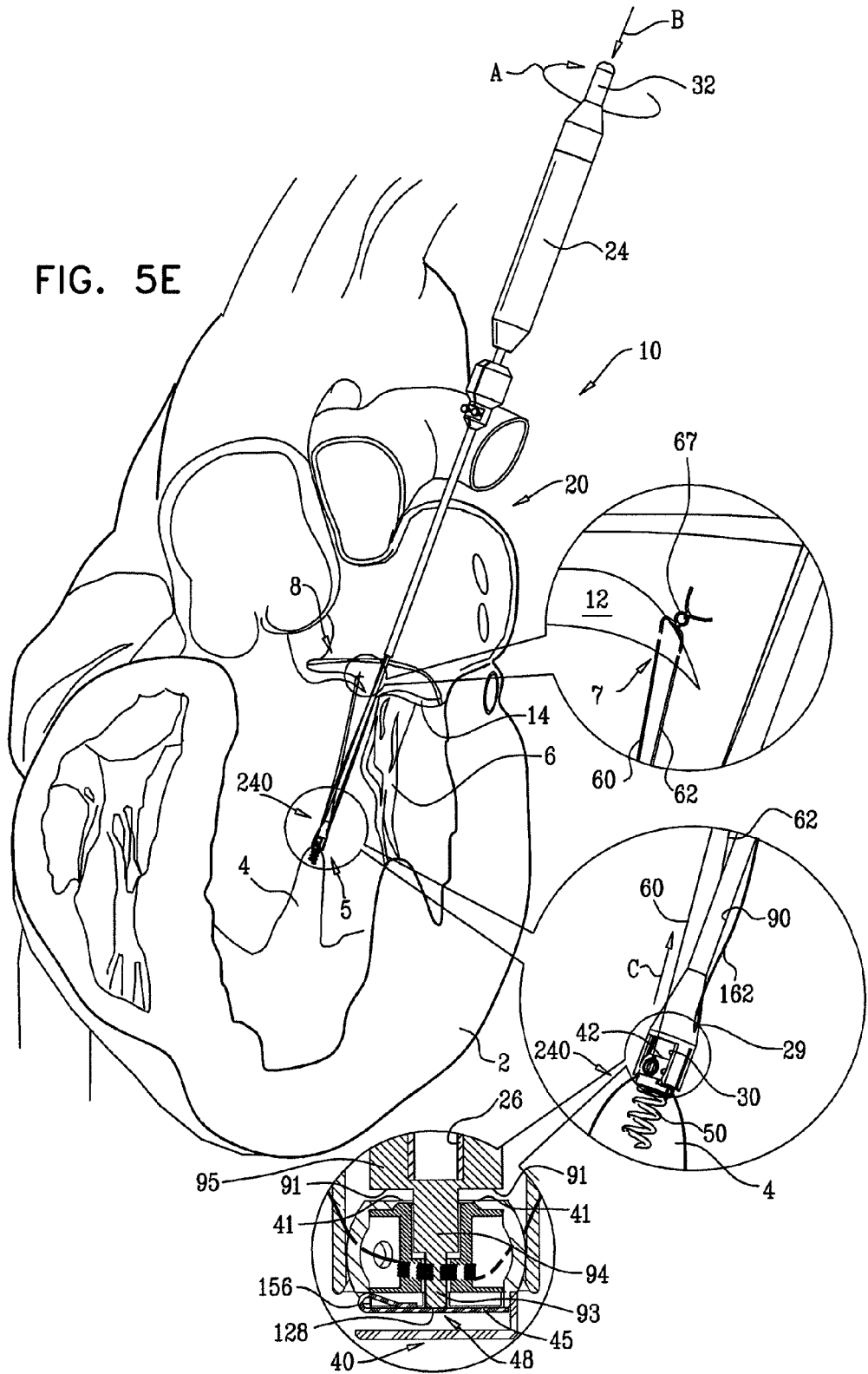

Reference is now made to FIGS. 3 and 5E. FIG. 5E shows the adjustment of longitudinal members 60 and 62 by adjusting mechanism 40 and delivery tool 20. During the adjustment of longitudinal members 60 and 62, locking mechanism 45 of adjustment mechanism 40 is disposed in an unlocked state with respect to spool 46 (as shown in FIG. 3). Rotating structure 32 is rotated in a first direction thereof, as indicated by arrow A. In response to the rotation of structure 32, torque-delivering tool 26 is rotated. Responsively, screwdriver head 95 that is coupled to the distal end of torque-delivering tool 26 is rotated and spool-rotating portion 94 pushes against the wall defining channel 48 of spool 46. Such pushing applies an annular force to the spool which facilitates rotation of spool 46 in a first direction thereof.

In response to the rotation of spool 46 in the first direction, as indicated by arrow A, respective first portions of longitudinal members 60 and 62 are wrapped around spool 46, as shown in the enlarged cross-sectional image of adjusting mechanism 40. As longitudinal members 60 and 62 are wrapped around spool 46, respective second portions of members 60 and 62 (i.e., the portions which are coupled to second implantation site 7) are pulled toward adjusting mechanism 40 implanted at first implantation site 5. This draws the second portions of longitudinal member 60 and 62 and leaflet 12 toward the first portions of longitudinal members 60 and 62 that are wrapped around spool 46. Responsively, the respective lengths of longitudinal members 60 and 62 between the second portions thereof and spool 46 are shortened and longitudinal members 60 and 62 are tightened.

Since spool 46 is unlocked (as shown in FIG. 3), spool 46 may be rotated in a second direction that is opposite the direction used to tighten longitudinal members 60 and 62 (i.e., in the direction that is opposite that which is indicated by arrow A in FIG. 5E). Rotating spool 46 in the second direction unwinds longitudinal members 60 and 62 from around spool 46 and thereby elongates the portions of longitudinal members 60 and 62 between first and second implantation sites 5 and 7.

Overtube 90 comprises a tube which surrounds torque-delivering tool 26. Since shaft 22 is retracted proximally (as shown) during the adjustment of longitudinal members 60 and 62, overtube 90 functions to provide rigidity and stability to torque-delivering tool 26 as it delivers torque to spool 46. Overtube 90 comprises a flexible material, e.g., polyamide, ePTFE, or PTFE. In some embodiments, the material of overtube 90 is braided. For some applications, overtube 90 is coated with PTFE.

As shown in FIG. 5E, longitudinal members 60 and 62 are pulled tight from their relaxed state (shown in FIG. 5D) in response to rotation facilitated by adjusting mechanism 40. Longitudinal members 60 and 62 are pulled until they resemble native chordae tendineae 6, and thus longitudinal members 60 and 62 function to replace the defective and stretched native chordae tendineae and restore normal functionality to heart valve 8.

Reference is again made to FIGS. 3 and 5E. FIG. 3 shows screwdriver head 95 being shaped to provide a horizontal shelf portion 91 which rests against upper surface 41 of spool housing 42. Similarly, spool-rotating portion 94 is shaped to define a shelf portion 143 which rests against a horizontal wall of spool 46 which defines a portion of channel 48. During the unlocked state of adjusting mechanism 40 (as shown in FIG. 3), screwdriver head 95 is disposed in a manner in which shelf portion 91 thereof rests against upper surface 41 of spool housing 42, and shelf 143 of spool-rotating portion 94 rests against the horizontal wall of channel 48, as shown.

Following the adjustment of the respective lengths of longitudinal members 60 and 62, delivery tool 20 is decoupled from spool assembly 240. The operating physician pushes on rotating structure 32, in the direction as indicated by arrow B in FIG. 5E. The proximal portion of handle 24 is shaped to define a recessed portion for receiving a distal portion of rotating structure 32 in response to the pushing thereof. Pushing on rotating structure 32 thereby pushes torque-delivering tool 26 coupled thereto. Responsively, screwdriver head 95 that is coupled to torque-delivering tool 26 is pushed distally. As screwdriver head 95 is pushed, shelf portion 91 pushes against upper surface 41 of housing 42 in order to facilitate pulling of tool 20 away from spool assembly 240. Responsively, screwdriver head 95 and graspers 30 are distanced from housing 42, as shown in the enlarged cross-sectional image of adjustment mechanism 40.

Graspers 30 are resiliently biased to angle inward and surround the curved outer wall of housing 42. Following the pushing of shelf portion 91 of screwdriver head 95 against upper surface 41 of housing 42, tool 20 is pulled proximally in the direction as indicated by arrow C in the enlarged image of spool assembly 240 and the distal portion of tool 20. During the pulling proximally of tool 240, the curved wall of housing 42 pushes against resilient graspers 30 in order to radially push graspers 30. Such pushing radially of graspers 30 helps further decouple tool 20 from spool assembly 240.

During the decoupling of tool 20 from spool assembly 46, spool-rotating portion 94 and distal force applicator 93 of screwdriver head 95 are pulled proximally such that the distal end of force applicator 93 is disposed proximally to and does not apply a pushing force to depressible portion 128 of locking mechanism 45. In the absence of the downward pushing force by screwdriver head 95, depressible portion 128 returns to its resting state, i.e., perpendicular with respect to the longitudinal axis of channel 48. As depressible portion 128 returns to its resting state, protrusion 156 is introduced within one of the plurality of recesses 154 of lower surface 152 of spool 46 and thereby locks and restricts rotation of spool 46.

Figure 5F:
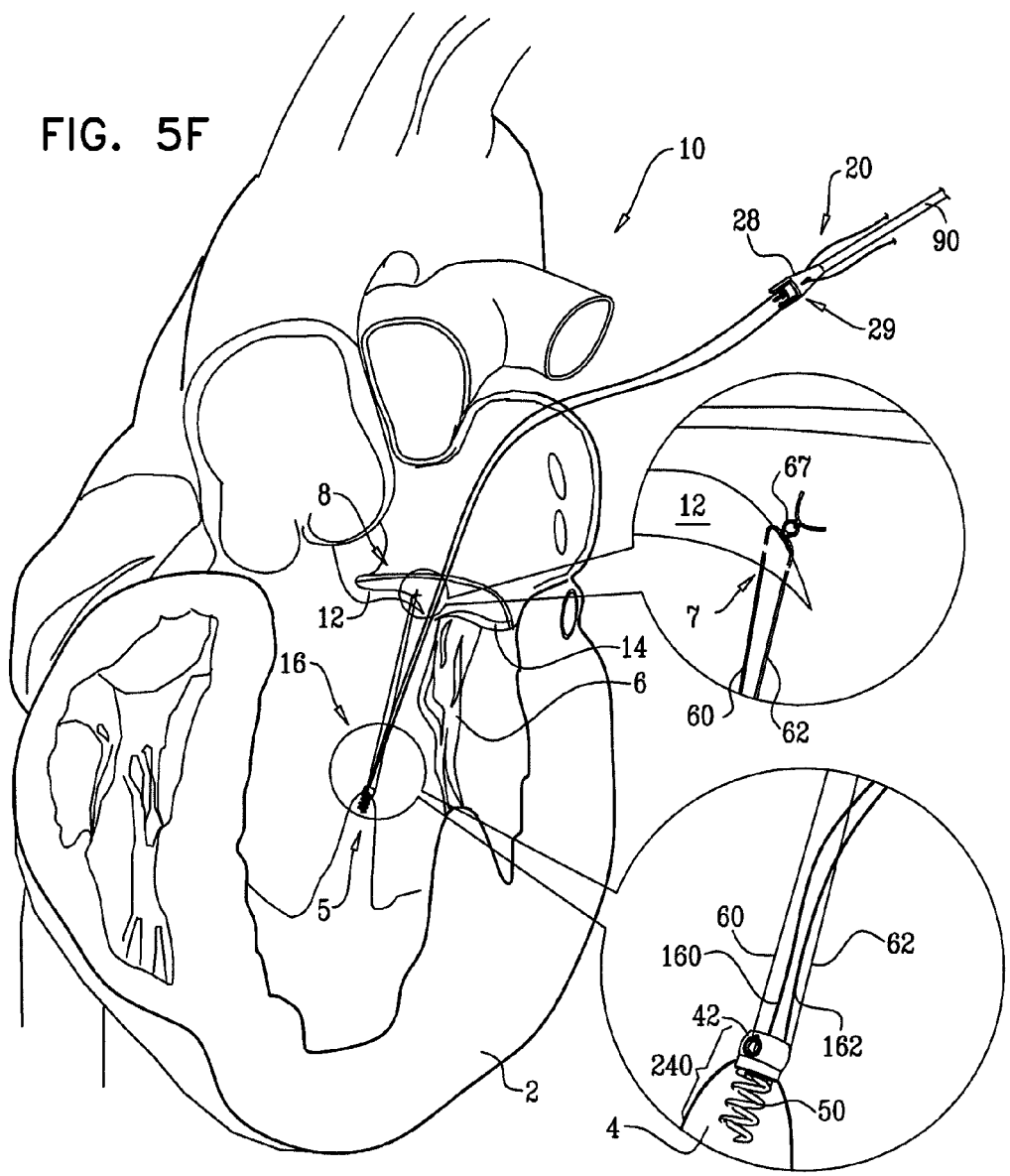

FIG. 5F shows delivery tool 20 being pulled away from heart 2 and ultimately outside of the body of the patient. Delivery tool 20 slides along guide wires 160 and 162 which pass through openings 29 in screwdriver housing 28 of tool 20. Guide wires 160 and 162 are left partially within heart 2 and provide an access to implantation site 5. Sliding of tool 20 along guide wires 160 and 162 frees heart 2 of any tool.

Once free of tool 20, the operating physician may then repair any other defect in the heart without any obstruction and interference by tool 20. In some cases, the operating physician introduces a second spool assembly 240 into another implantation site in the left ventricle and repairs another portion of heart 2. In some embodiments, the second spool assembly is implanted in a second papillary muscle of the ventricle and the longitudinal member(s) coupled thereto are coupled at their free ends to either leaflet 12 or 14. The longitudinal member(s) then function as secondary artificial chorda(e) tendinea(e).

In some embodiments, the second spool assembly 240 is coupled to a first portion of the ventricle wall (i.e., and not to the papillary muscle) at the base of the papillary muscle, or at another portion of the ventricle wall which faces and surrounds the ventricular lumen of heart 2. In some embodiments, the free ends of the longitudinal member(s) coupled to the second spool assembly are coupled to either leaflet 12 or 14 (as shown hereinbelow with reference to FIG. 8). Alternatively, the free ends of the longitudinal member(s) are coupled to a second portion of the ventricle wall (as shown hereinbelow with reference to FIGS. 20A-B) in order to draw the first and second portions the ventricle wall toward one another.

In either embodiment, guide wires 160 and 162 remain coupled to housing 42 during and following the initial procedure including the implantation of spool assembly and adjustment of longitudinal members 60 and 62. Guide wires 160 and 162 enable the operating physician to access implantation site 5 at any time during and after the initial procedure. During the initial implantation procedure delivery tool 20 may remain coupled to guide wires 160 and 162 and slide in and out of heart 2. The physician is able to slide tool 20 toward spool assembly 240 and facilitate supplemental rotation of spool 46 and adjustment of longitudinal members 60 and 62. Following the adjustment, tool 20 is slid out of heart 2 and is decoupled from guide wires 160 and 162.

Figure 5G:
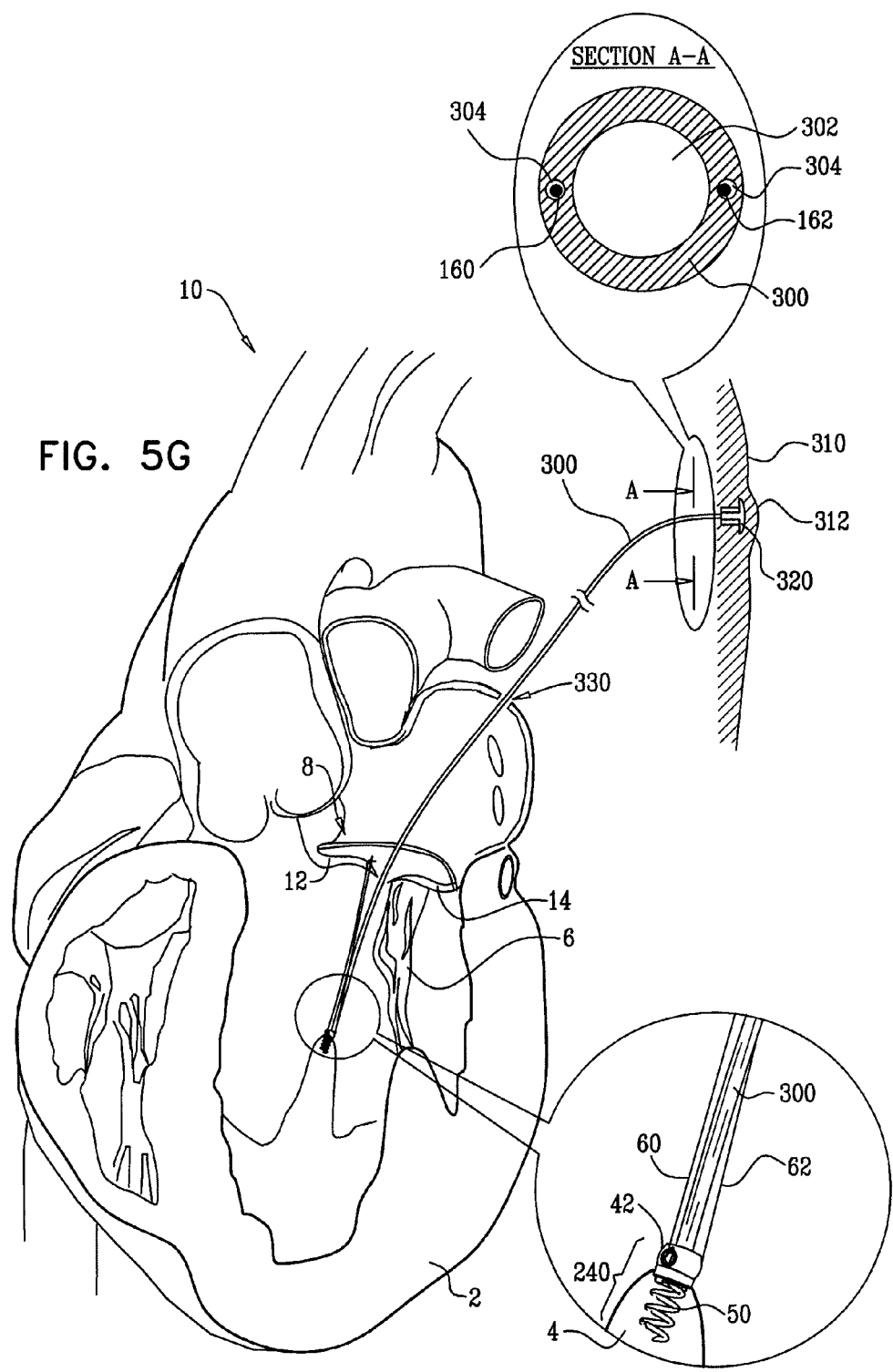

FIG. 5G shows a multilumen guide tube 300 coupled at a distal end thereof to spool assembly 240. Guide tube 300 defines a primary lumen 302 and respective secondary lumens 304 which surround guide wires 160 and 162. Following the removal of tool 20, guide tube 300 is advanced toward implantation site 5 along guide wires 160 and 162.

Guide tube 300 is advanced along guide wires 160 and 162 through an opening 330 in heart 2, and ultimately toward implantation site 5. A distal end of guide tube 300 is coupled to spool housing 42 of spool assembly 240, and a proximal end of guide tube 300 is coupled to a portion of subcutaneous tissue of the patient. A port 320 is coupled to a proximal end of guide tube 300 and is implanted subcutaneously beneath skin 310 of the patient typically in the vicinity of the ribcage. Port 320 projects slightly under skin 310 to create a bump 312.

Figure 6:
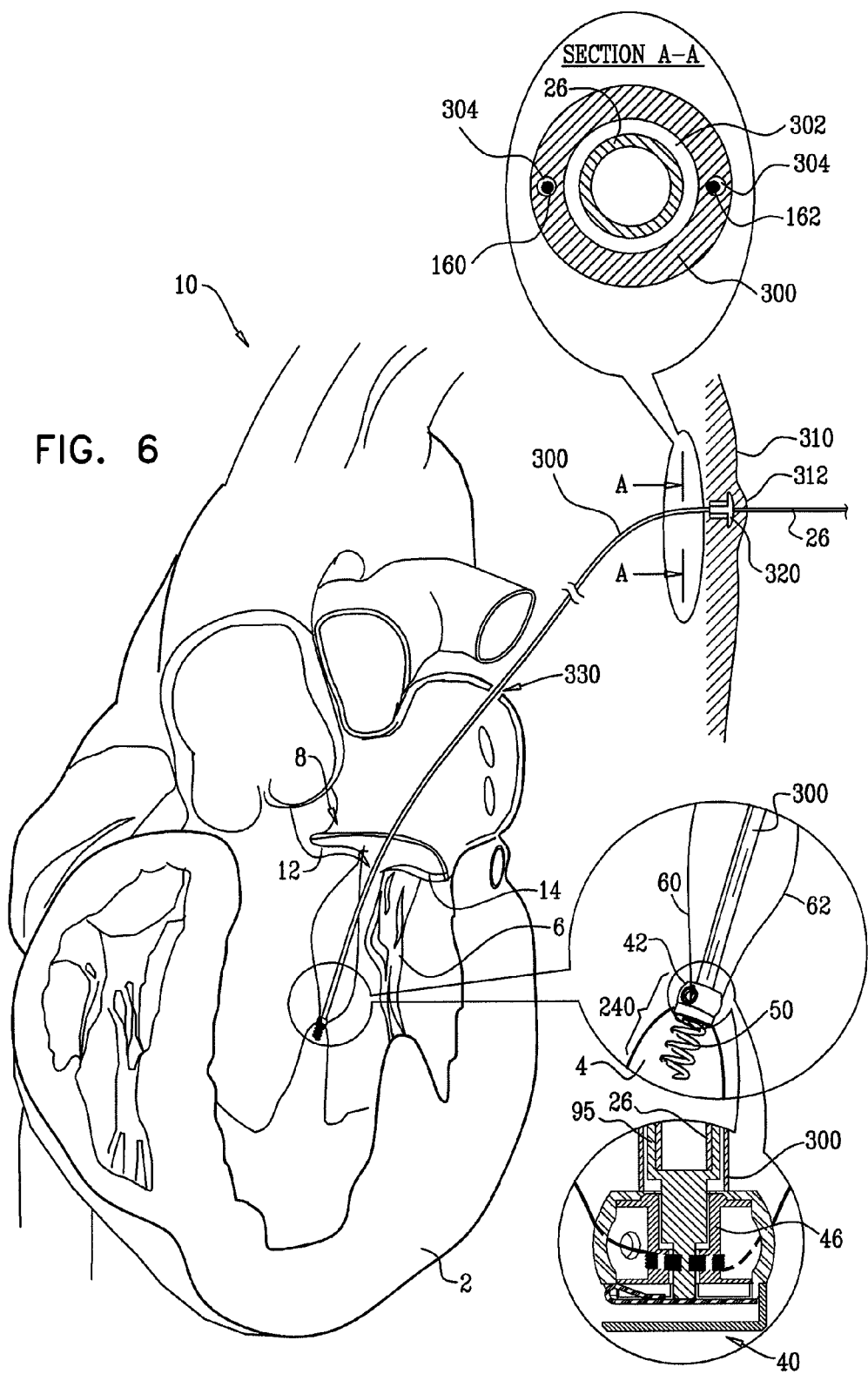
FIG. 6 is a schematic illustration of a port mechanism being coupled to the spool assembly, in accordance with an embodiment of the present invention.

FIG. 6 is a schematic illustration of extracardiac apparatus comprising torque-delivering tool 26 accessing spool assembly 240 via port 320, in accordance with an embodiment of the present invention. The physician feels for bump 312 of skin 310 and creates a small incision in the tissue in order to access port 320. Torque-delivering tool 26 is advanced through primary lumen 302 of guide tube 300 (as shown in the transverse cross-sectional image of guide tube 300) and accesses adjusting mechanism 40 of spool assembly 240 from a site outside the body of the patient.

The operating physician may access spool assembly 240 via port 320, at a later stage following initial implantation of assembly 240 in order to readjust longitudinal members 60 and 62. For example, in the event that longitudinal members 60 and 62 are loosened (as shown) and need to be tightened, spool assembly 240 may be accessed in order to tighten longitudinal members 60 and 62.

Torque-delivering tool 26 is coupled at a distal end thereof to screwdriver head 95. Screwdriver head 95 accesses spool 46 of adjustment mechanism 40 and rotates spool 46 (in a manner as described hereinabove) in order to adjust longitudinal members 60 and 62. The readjustment procedure is typically performed with the aid of imaging, such as fluoroscopy, transesophageal echo, and/or echocardiography.

Figure 7:
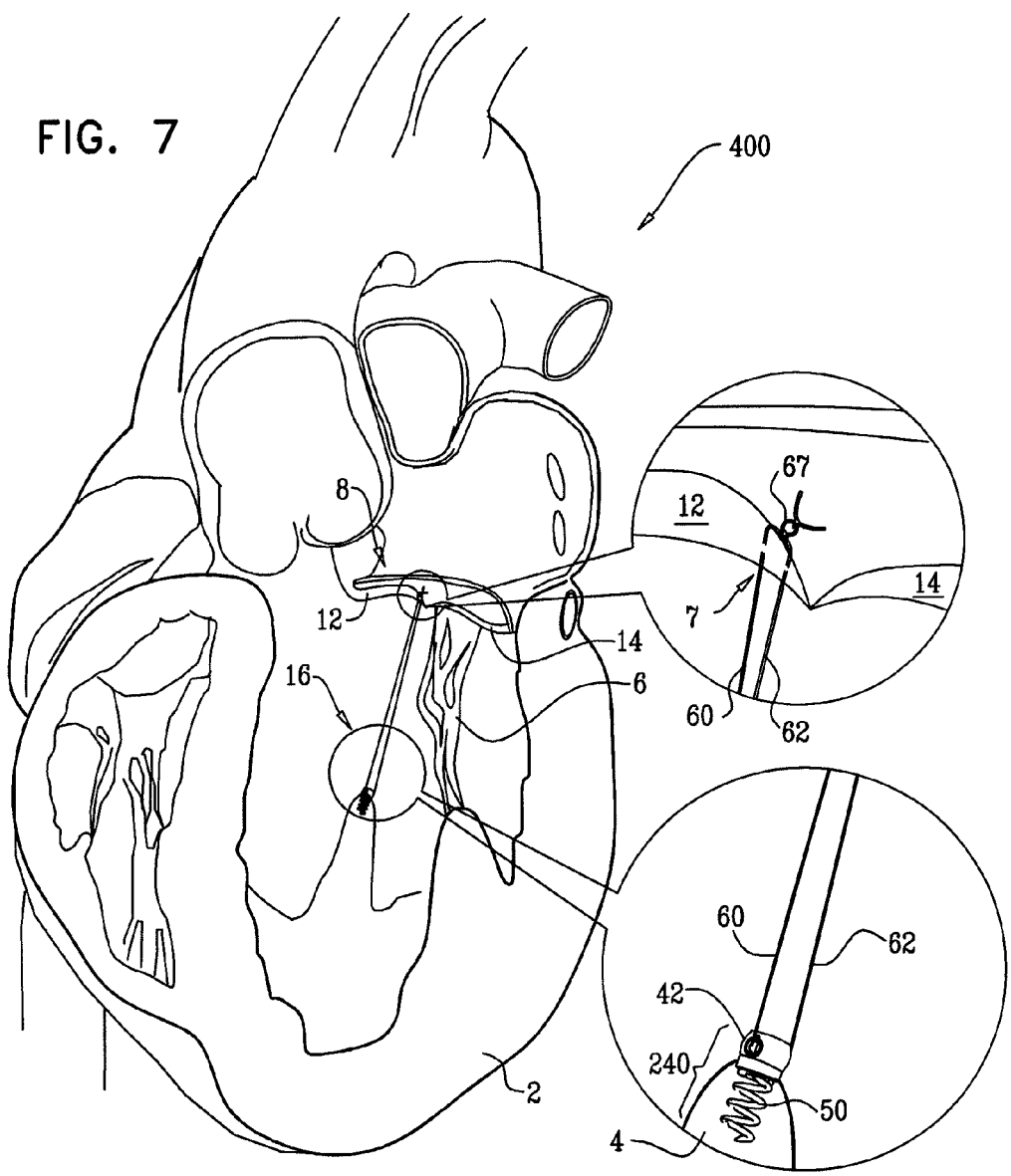
FIG. 7 is a schematic illustration of the spool assembly and the repair chords, in accordance with an embodiment of the present invention.

Reference is now made to FIG. 7, which is a schematic illustration of a system 400 for implanting spool assembly 240 and adjusting longitudinal members 60 and 62, as described hereinabove with reference to FIGS. 5A-G, with the exception that guide wires 160 and 162 do not remain partially disposed within heart 2, in accordance with an embodiment of the present invention. In this embodiment, guide wires 160 and 162 are used only during the initial implantation of spool assembly 240 and adjustment of longitudinal members 60 and 62. Guide wires 160 and 162 in this embodiment facilitate the removal of tool 20 from heart 2 and the replacement of tool 20 in heart 2 during the initial procedure.

Figure 8:
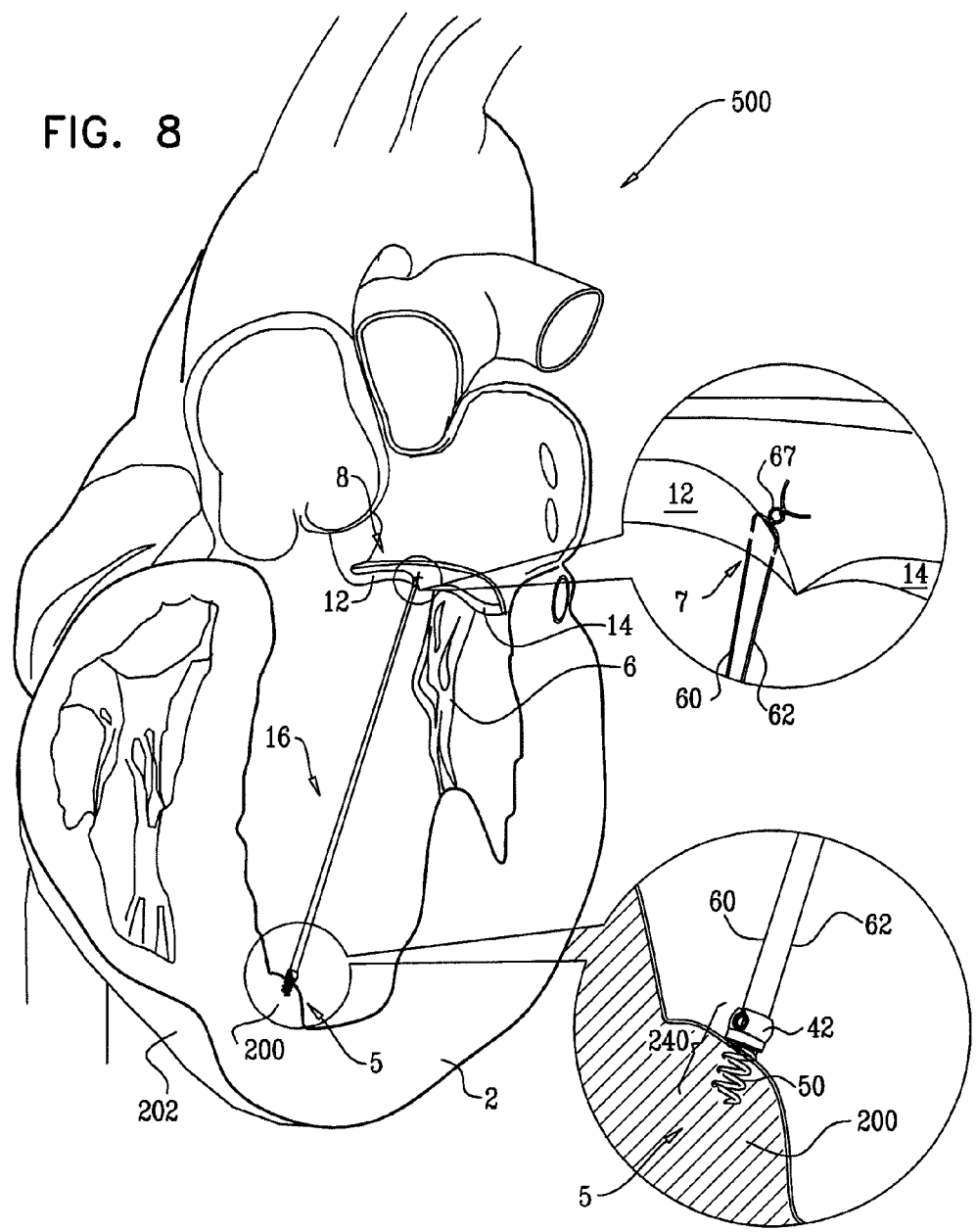
FIG. 8 is a schematic illustration of the adjusting mechanism being implanted at a portion of a ventricular wall, in accordance with an embodiment of the present invention.

FIG. 8 is a schematic illustration of a system 500 for implanting spool assembly 240 and adjusting longitudinal members 60 and 62, as described hereinabove with reference to FIGS. 5A-G, with the exception that spool assembly is implanted in a portion 200 of the heart wall of the ventricle, in accordance with an embodiment of the present invention. Portion 200 of the heart wall includes a portion of the wall which faces and surrounds the ventricular lumen of heart 2.

Tissue anchor 50 is screwed into the cardiac tissue in a manner in which it is disposed fully within portion 200 of the heart tissue, e.g., endocardium or myocardium, and does not extend beyond a pericardium 202 of heart 2.

Reference is now made to FIGS. 9A-K, which are schematic illustrations of a system for implanting and adjusting repair chords, and a transcatheter procedure for implanting the chords in a heart, in accordance with an embodiment of the present invention. The procedure is typically performed with the aid of imaging, such as fluoroscopy, transesophageal echo, and/or echocardiography.

Figure 9A:
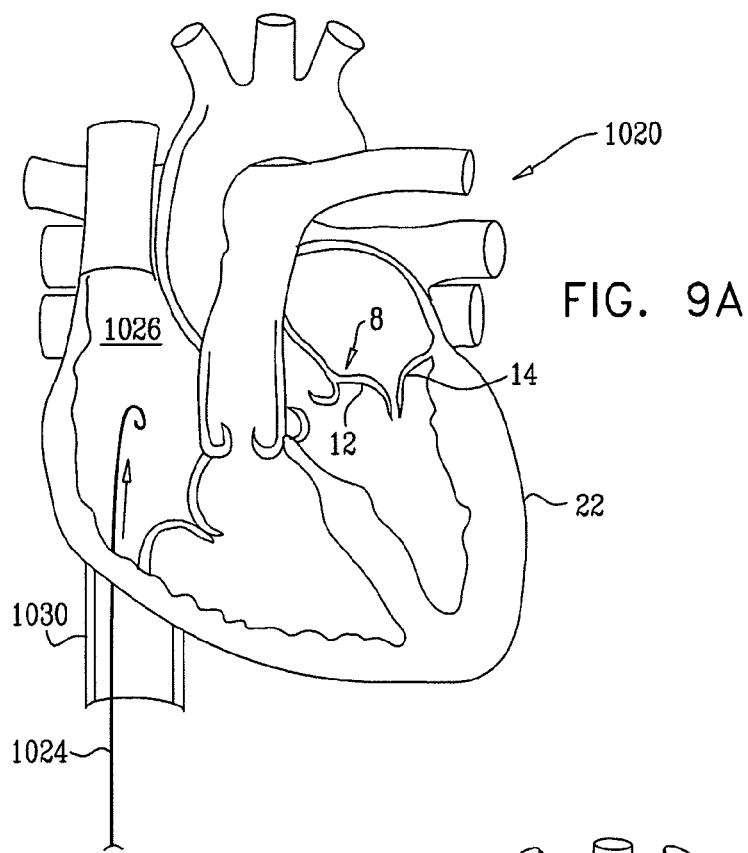

The procedure typically begins with the advancing of a semi-rigid guide wire 1024 into a right atrium 1026 of the patient, as shown in FIG. 9A.

Figure 9B:
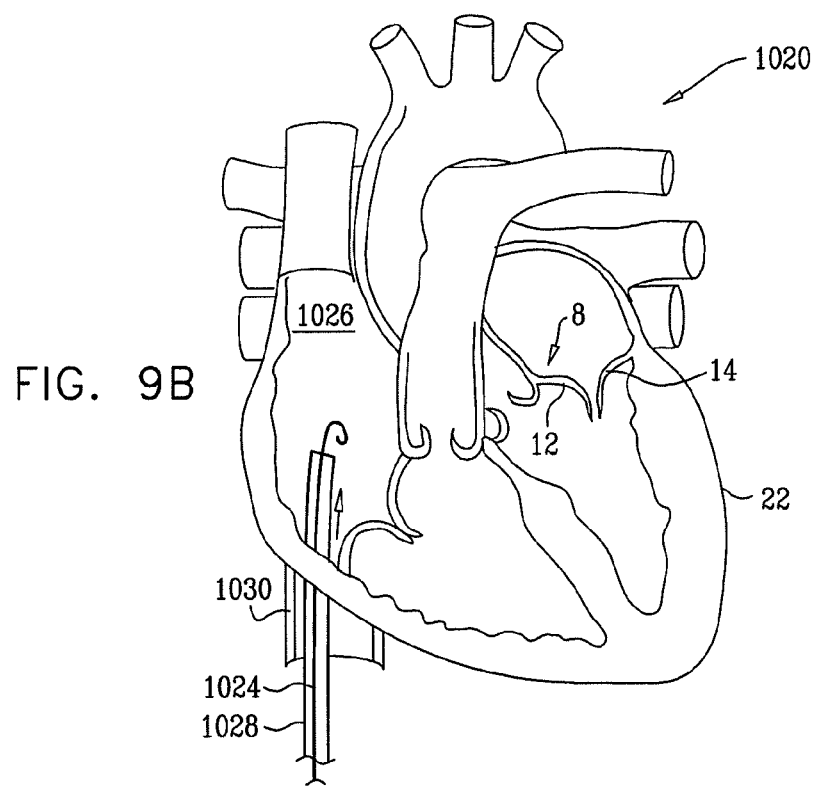
Figure 9C:
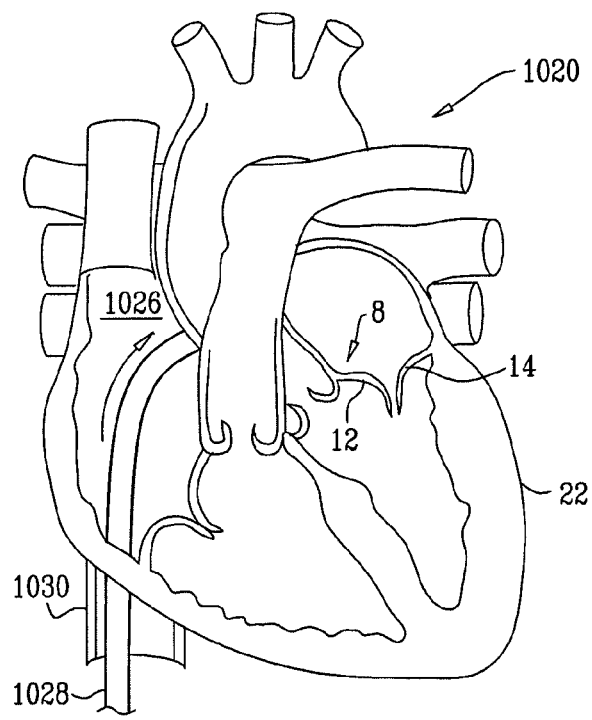

As shown in FIG. 9B, guide wire 1024 provides a guide for the subsequent advancement of a sheath 1028 therealong and into right atrium 1026. Once sheath 1028 has entered the right atrium, guide wire 1024 is retracted from the patient's body. Sheath 1028 typically comprises a 14-20 F sheath, although the size may be selected as appropriate for a given patient. Sheath 1028 is advanced through vasculature into the right atrium using a suitable point of origin typically determined for a given patient. For example:

sheath 1028 may be introduced into the femoral vein of the patient, through an inferior vena cava 1030, into right atrium 1026, and into the left atrium transseptally, typically through the fossa ovalis;

sheath 1028 may be introduced into the basilic vein, through the subclavian vein to the superior vena cava, into right atrium 1026, and into the left atrium transseptally, typically through the fossa ovalis; or sheath 1028 may be introduced into the external jugular vein, through the subclavian vein to the superior vena cava, into right atrium 1026, and into the left atrium transseptally, typically through the fossa ovalis.

In an embodiment of the present invention, sheath 1028 is advanced through inferior vena cava 1030 of the patient (as shown) and into right atrium 1026 using a suitable point of origin typically determined for a given patient.

Sheath 1028 is advanced distally until the sheath reaches the interatrial septum.

Figure 9D:
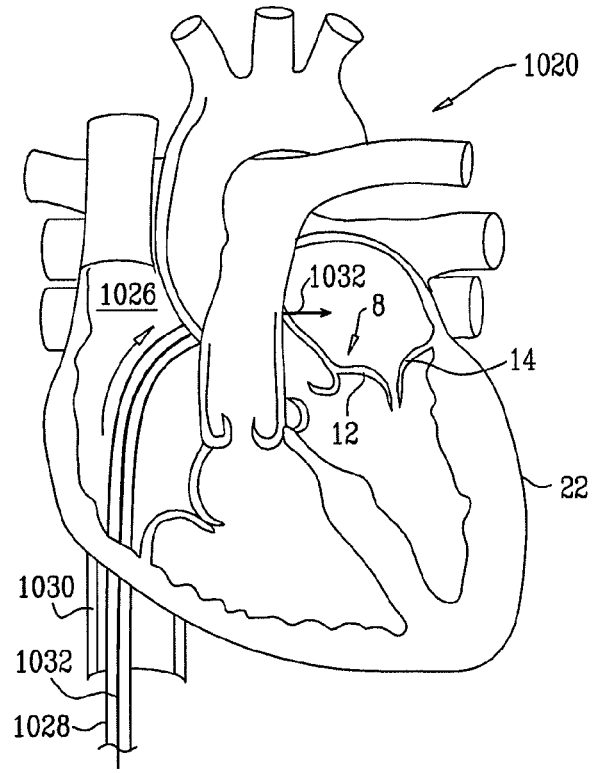

As shown in FIG. 9D, a resilient needle 1032 and a dilator (not shown) are advanced through sheath 1028 and into the heart. In order to advance sheath 1028 transseptally into the left atrium, the dilator is advanced to the septum, and needle 1032 is pushed from within the dilator and is allowed to puncture the septum to create an opening that facilitates passage of the dilator and subsequently sheath 1028 therethrough and into the left atrium. The dilator is passed through the hole in the septum created by the needle. Typically, the dilator is shaped to define a hollow shaft for passage along needle 1032, and the hollow shaft is shaped to define a tapered distal end. This tapered distal end is first advanced through the hole created by needle 1032. The hole is enlarged when the gradually increasing diameter of the distal end of the dilator is pushed through the hole in the septum.

Figure 9E:
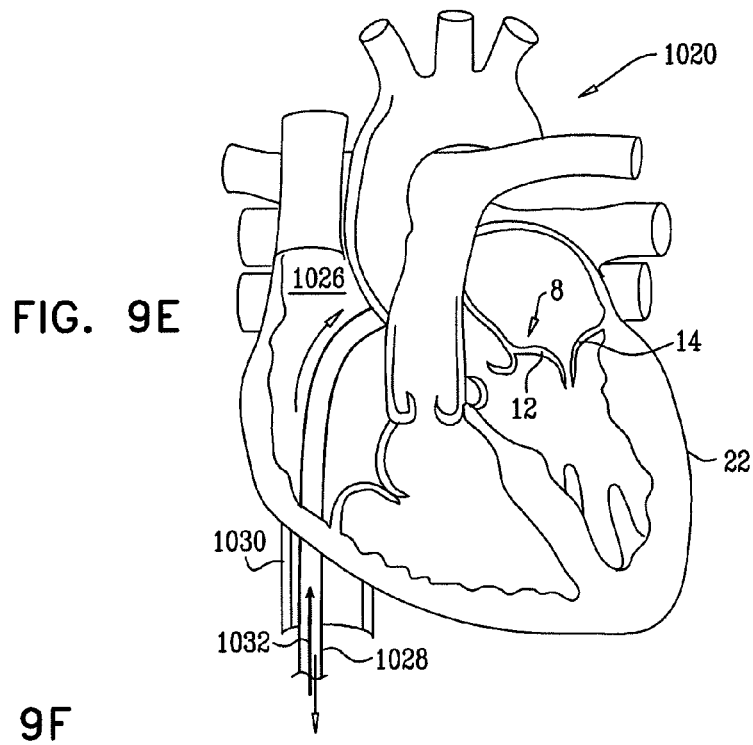

The advancement of sheath 1028 through the septum and into the left atrium is followed by the extraction of the dilator and needle 1032 from within sheath 1028, as shown in FIG. 9E.

Figure 9F:
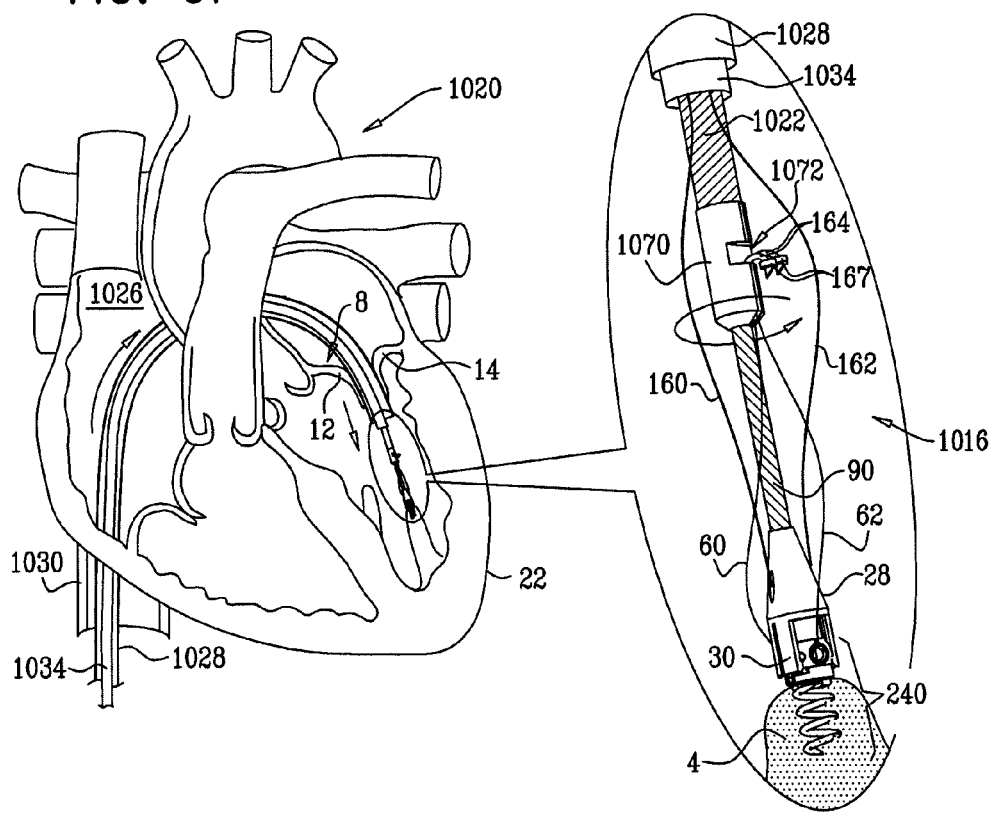
Figure 91:
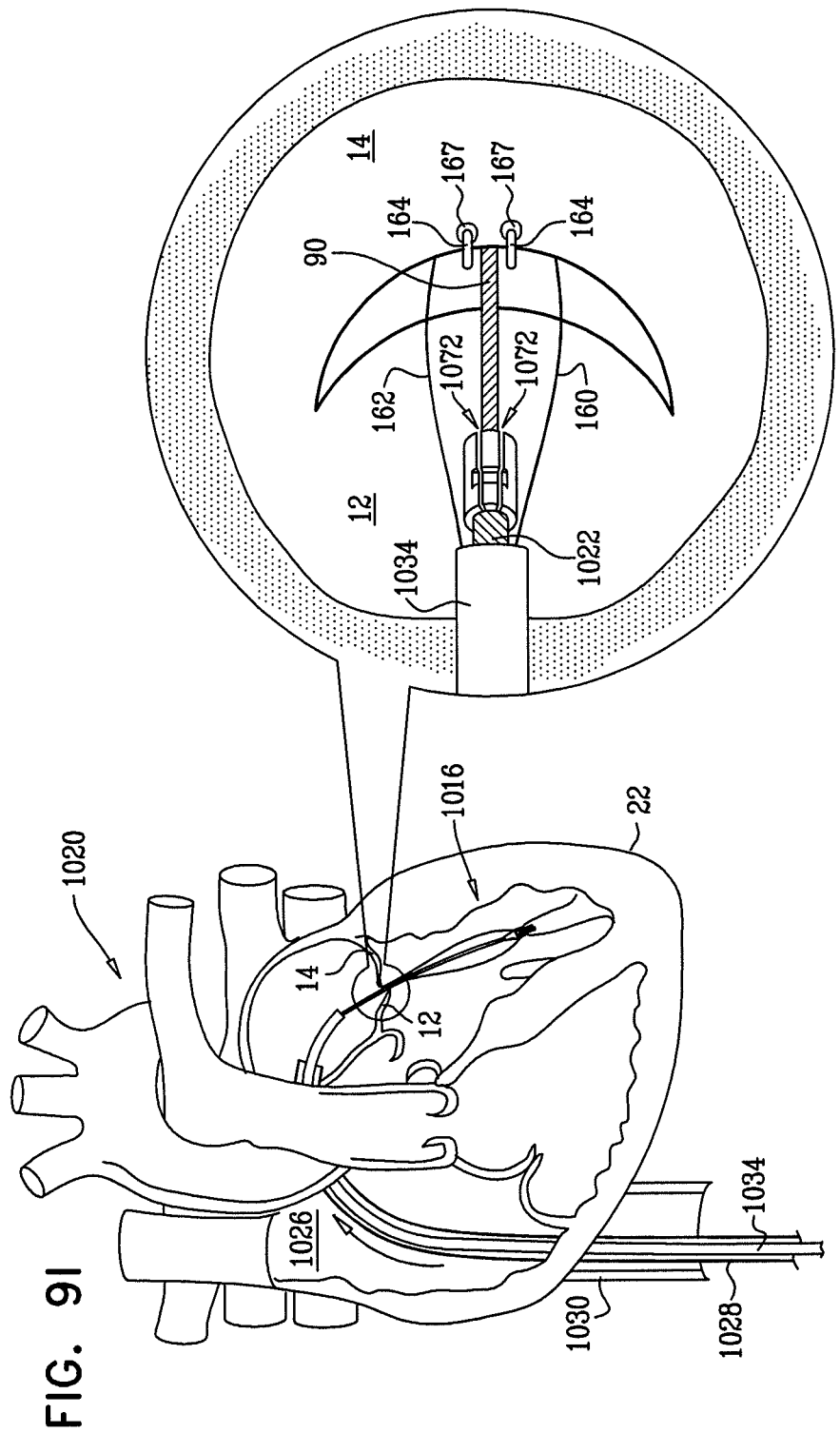

As shown in FIG. 9F, the system comprises a delivery tool 1020 and an implant assembly 1016. Delivery tool 1020 comprises a surrounding shaft 1022, which is configured to be slidable over and along a central shaft 90, such that the surrounding shaft surrounds a portion of the central shaft. Surrounding shaft 1022 typically comprises a coupling element holder 1070, which is fixed to surrounding shaft 1022 in a vicinity of the distal end of shaft 1022. A distal portion of delivery tool 1020 comprises screwdriver housing 28, as described hereinabove. The delivery tool further comprises an advancement tube 1034, which is configured to hold the other elements of the delivery tool as the delivery tool is advanced through sheath 1028.

Other than as described hereinbelow, implant assembly 1016 is generally similar to implant assembly 16, described hereinabove with reference to FIGS. 1-8. Among other features, implant assembly 1016 comprises spool assembly 240 and longitudinal members 60 and 62. Instead of suture needles 64 of implant assembly 16, implant assembly 1016 comprises one or more leaflet-engaging elements, such as surgical hooks 164, which are coupled to respective proximal ends of longitudinal member 60 and 62, and are disposed with respective slits 1072 of coupling element holder 1070. Optionally, each of the hooks comprises a respective pledget 167, which may help facilitate tissue growth between the hooks and the leaflet. Pledgets 167 may also function to prevent tearing of the leaflets. Alternative leaflet-engaging elements are described hereinbelow with reference to FIGS. 10A-G, 11A-E, 12A-G, 14A-E, 15A-C, 16A-B, 17A-G, 18A-D, and 23A-I.

As shown in FIG. 9F, delivery tool 1020 and implant assembly 1016 are advanced through sheath 1028 into the left ventricle. All or a portion of the delivery tool is rotated (e.g., central shaft 90) in order to screw the helical anchor of spool assembly 240 into tissue of papillary muscle 4.

As shown in FIG. 9G, surrounding shaft 1022 and coupling element holder 1070 are withdrawn proximally into the left atrium, while maintaining the distal end of central shaft 90 in place and within the ventricle.

As shown in FIGS. 9H and 9I (which is a view from the left atrium), surrounding shaft 1022 and coupling element holder 1070 are advanced distally between leaflets 12 and 14. While the distal end of central shaft 90 is maintained in place and within the ventricle, coupling element holder 1070 of surrounding shaft 1022 is used to engage exactly one of leaflets 12 and 14 with one or more of surgical hooks 164. In order to couple the hooks to the leaflet, if necessary the surgeon may manipulate holder 1070. For example, the surgeon may push the holder against the leaflet, and/or slightly withdraw and advance the holder one or more times. Alternatively or additionally, the natural motion of the leaflet may engage the leaflet with the hooks. It is noted that before and after this engagement occurs, leaflets 12 and 14 are free to open and close during the natural cardiac cycle. The reference force provided by central shaft 90 helps the holder engage the leaflet, in part because stabilization of central shaft 90 provides a stabilized path over which surrounding shaft 1022 advances and withdraws. The positioning of coupling element holder 1070 between the leaflets, with the hooks oriented toward one of the leaflets, helps ensure that the surgical hooks engage exactly one of the leaflets. Typically, but not necessarily, the hooks engage the leaflet by puncturing the leaflet.

Figure 9J:
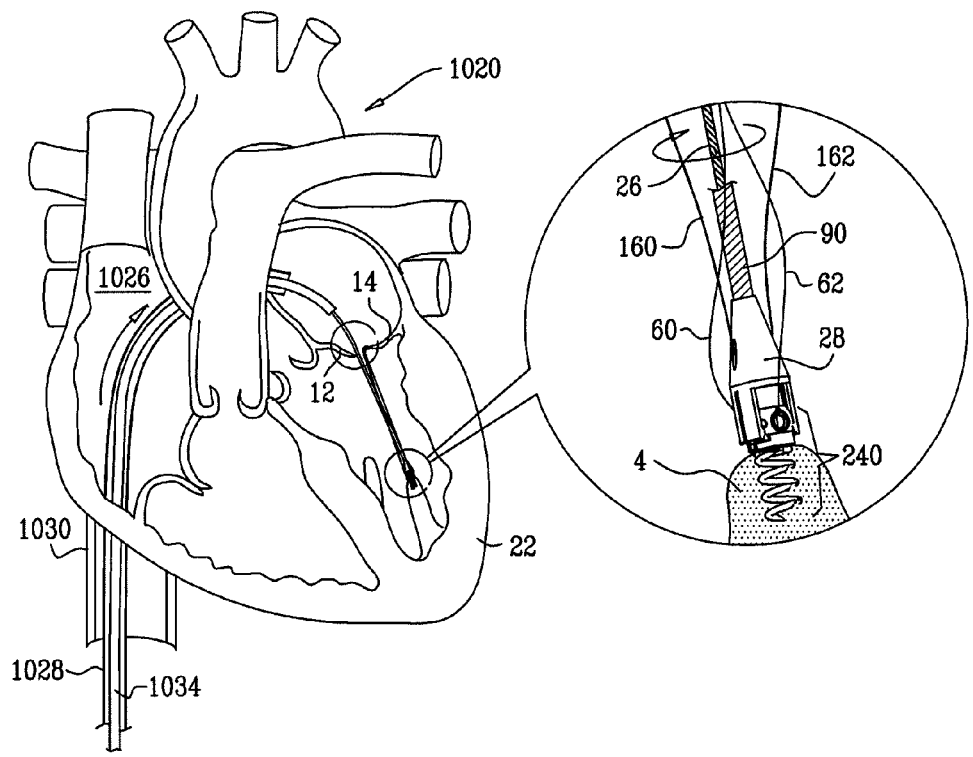

As shown in FIG. 9J, torque-delivering tool 26 (within central shaft 90) is rotated to rotate spool 46 of spool assembly 240, thereby wrapping longitudinal members 60 and 62 around spool 46, and shortening the effective length of the longitudinal members, as described hereinabove. This shortening has the effect of bringing the prolapsed leaflet (leaflet 14 in the figures) toward the ventricle.

Figure 9K:
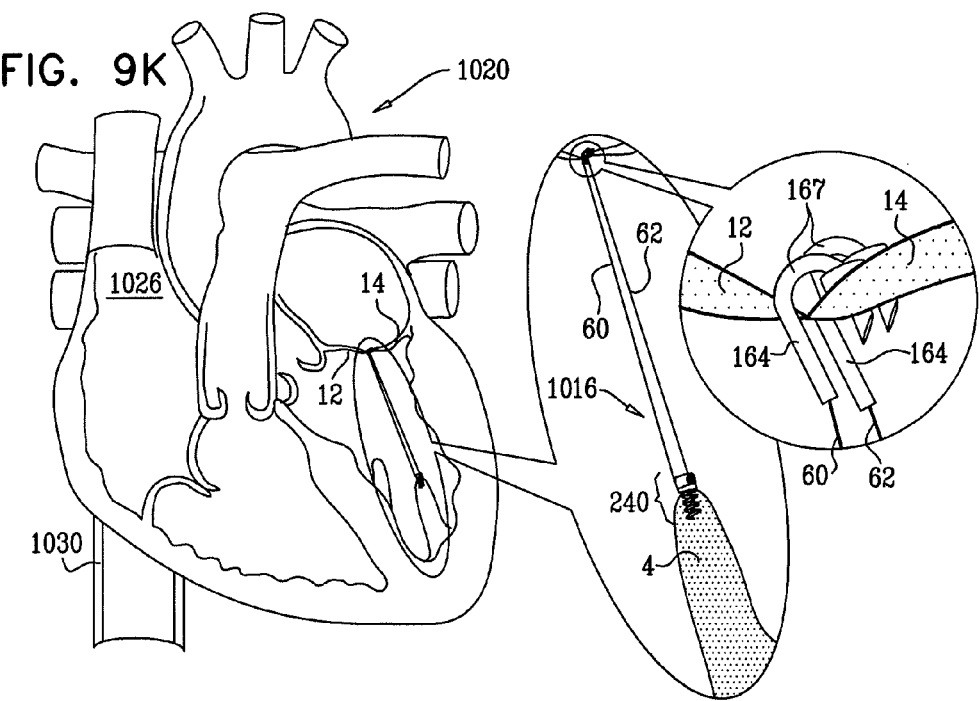

Delivery tool 1020 is withdrawn from the heart, leaving implant assembly 1016 implanted in the left ventricle and leaflets, as shown in FIG. 9K. Typically, screwdriver housing 28 is disengaged from spool assembly 240 by gently pulling on the screwdriver housing.

For some applications, delivery tool 1020 comprises one or more return guide wires 160 and 162. The distal ends of the guide wires are coupled to spool assembly 240, and the proximal ends of the guide wires pass through advancement tube 1034. The guide wires enable the surgeon to reengage delivery tool 1020 to spool assembly 240 if necessary, after the delivery tool has been disengaged and withdrawn from the heart, as described hereinabove with reference to FIG. 9K. To reengage, the surgeon advances screwdriver housing 28 of delivery tool 1020 over the guide wires until the housing arrives at the spool, and pushes the housing onto the spool, thereby reengaging the screwdriver housing to the housing surrounding the spool. For example, the surgeon may decide to tighten or loosen longitudinal members 60 and 62 after viewing images of the functioning of the valve.

Once the surgeon determines that implant assembly 1016 has been properly implanted and configured, guide wires 160 and 162 are decoupled from spool assembly 240, such as by cutting (step not shown). For some applications, return guide wires 160 and 162 comprise a single guide wire that is looped through spool assembly 240. To decouple the guide wire from the spool assembly, the surgeon releases one end of the guide wire and pulls on the other end.

Reference is now made to FIGS. 10A-G, which are schematic illustrations of another system for implanting and adjusting repair chords, and a transcatheter procedure for implanting the chords in a heart, in accordance with an embodiment of the present invention. Except as described hereinbelow, this system and procedure are similar to the system and procedure described hereinabove with reference to FIGS. 9A-K.

Figure 10A:
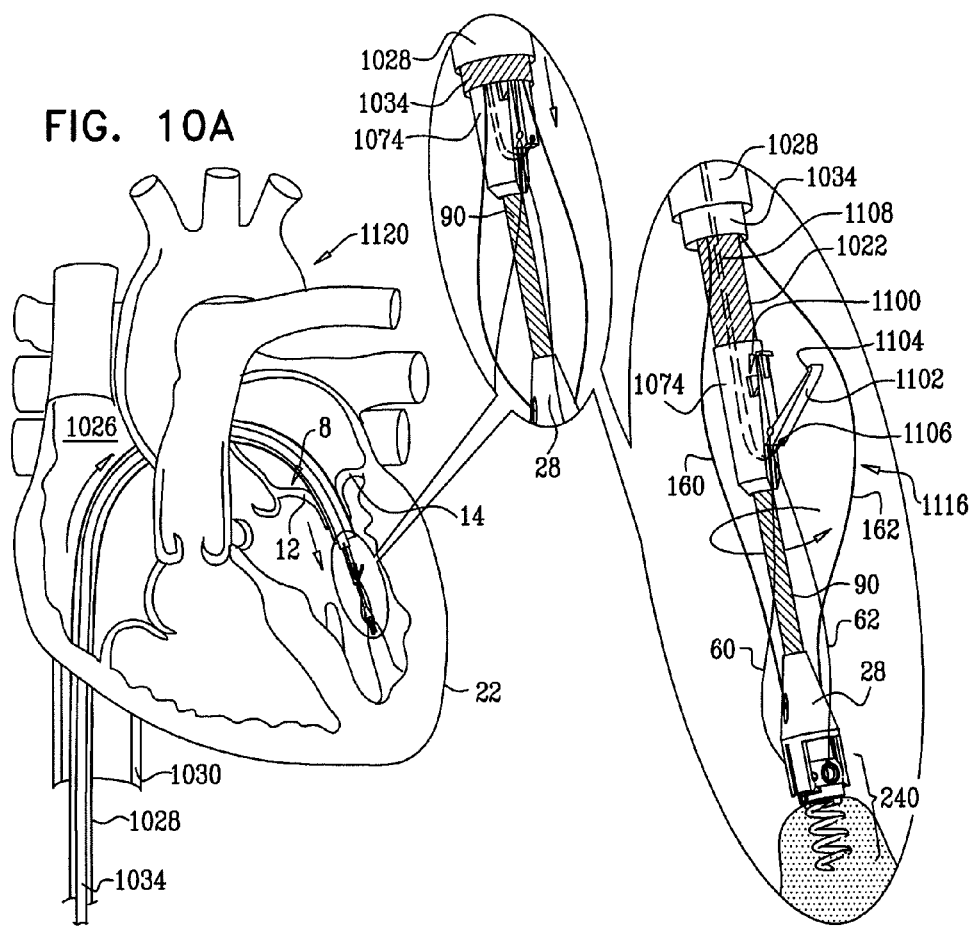
FIGS. 10A-G are schematic illustrations of another system for implanting and adjusting repair chords, and a transcatheter procedure for implanting the chords in a heart, in accordance with an embodiment of the present invention.
Figure 10B:
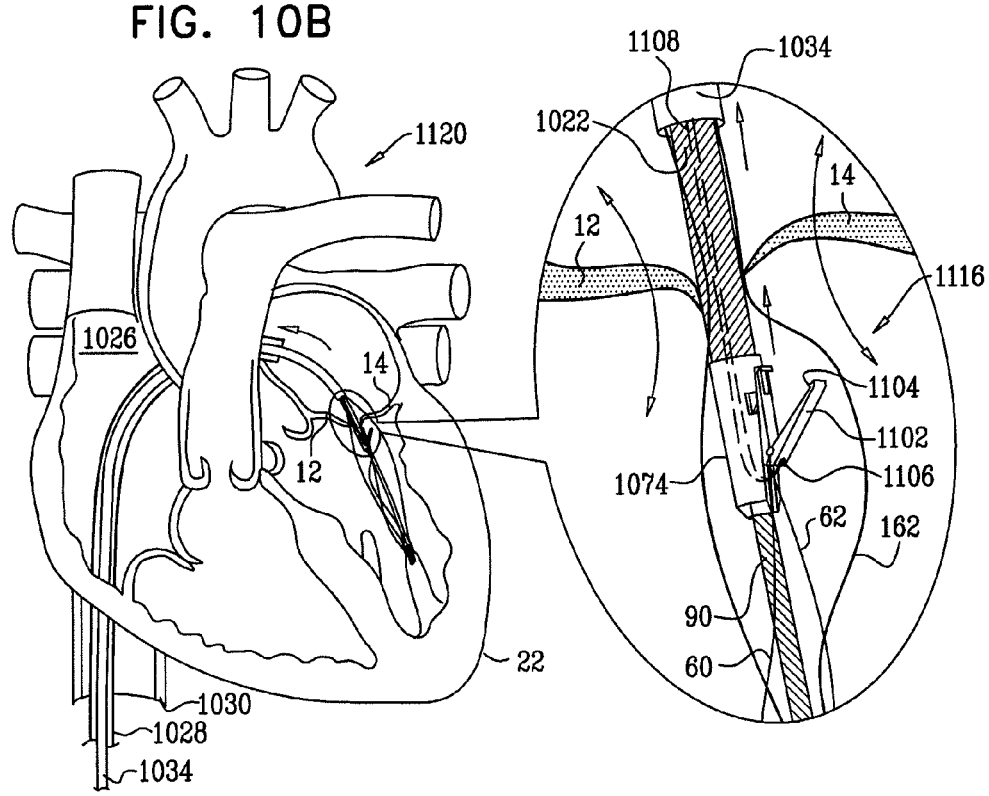
Figure 10C:
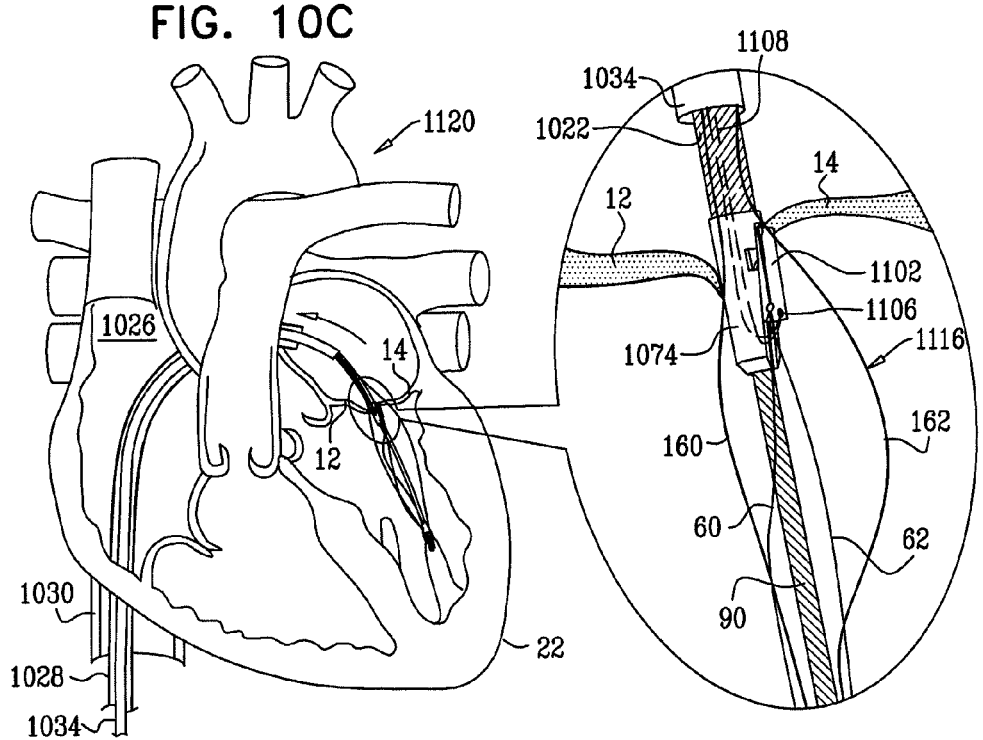
Figure 10D:
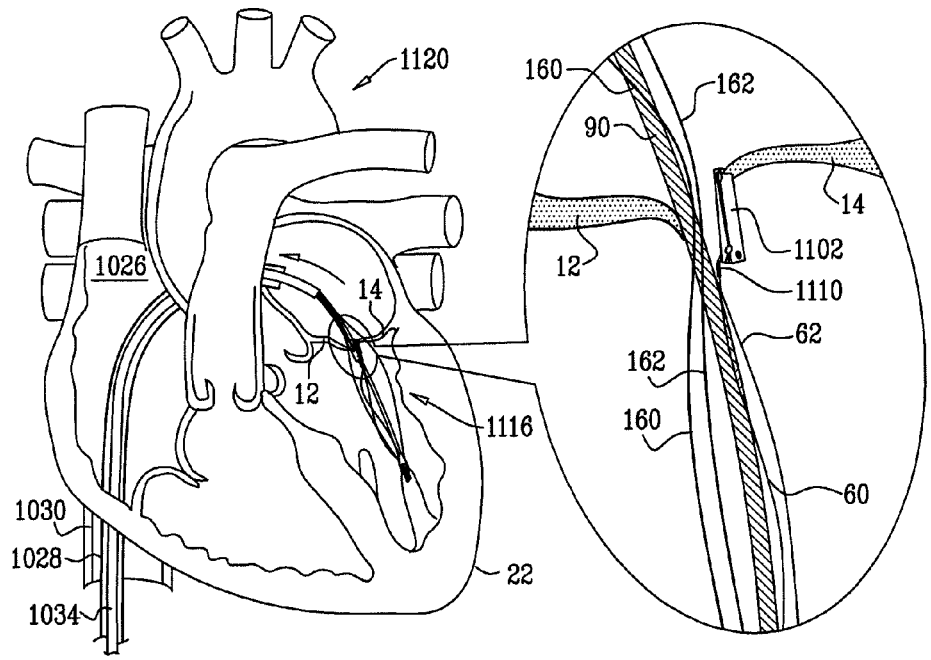
Figure 10E:
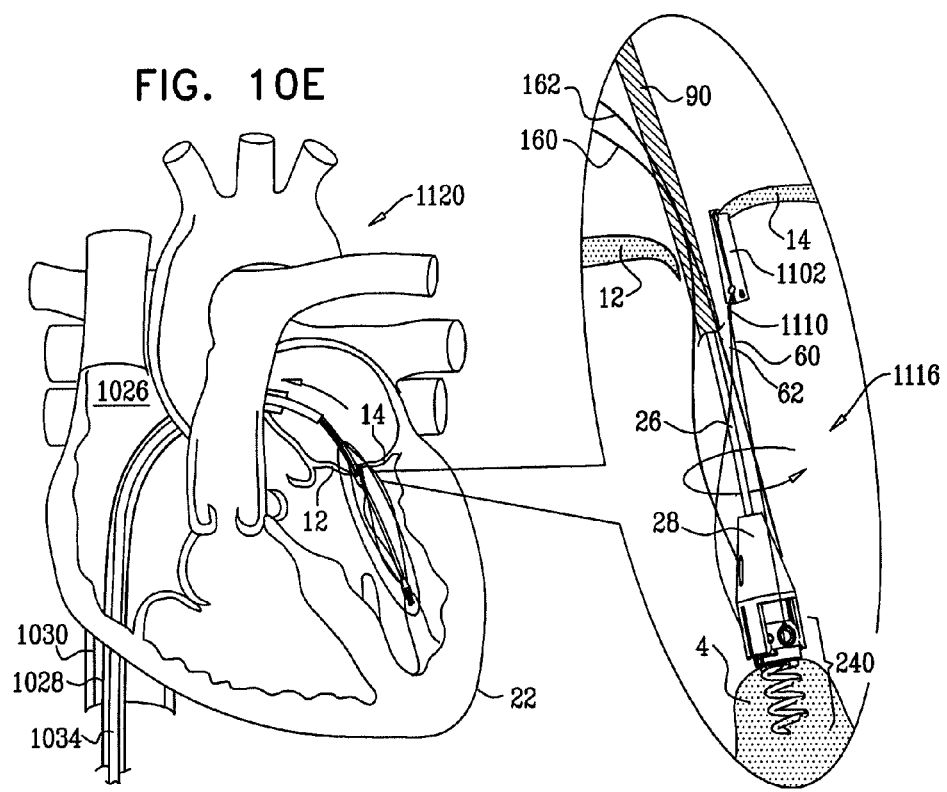
Figure 10F:
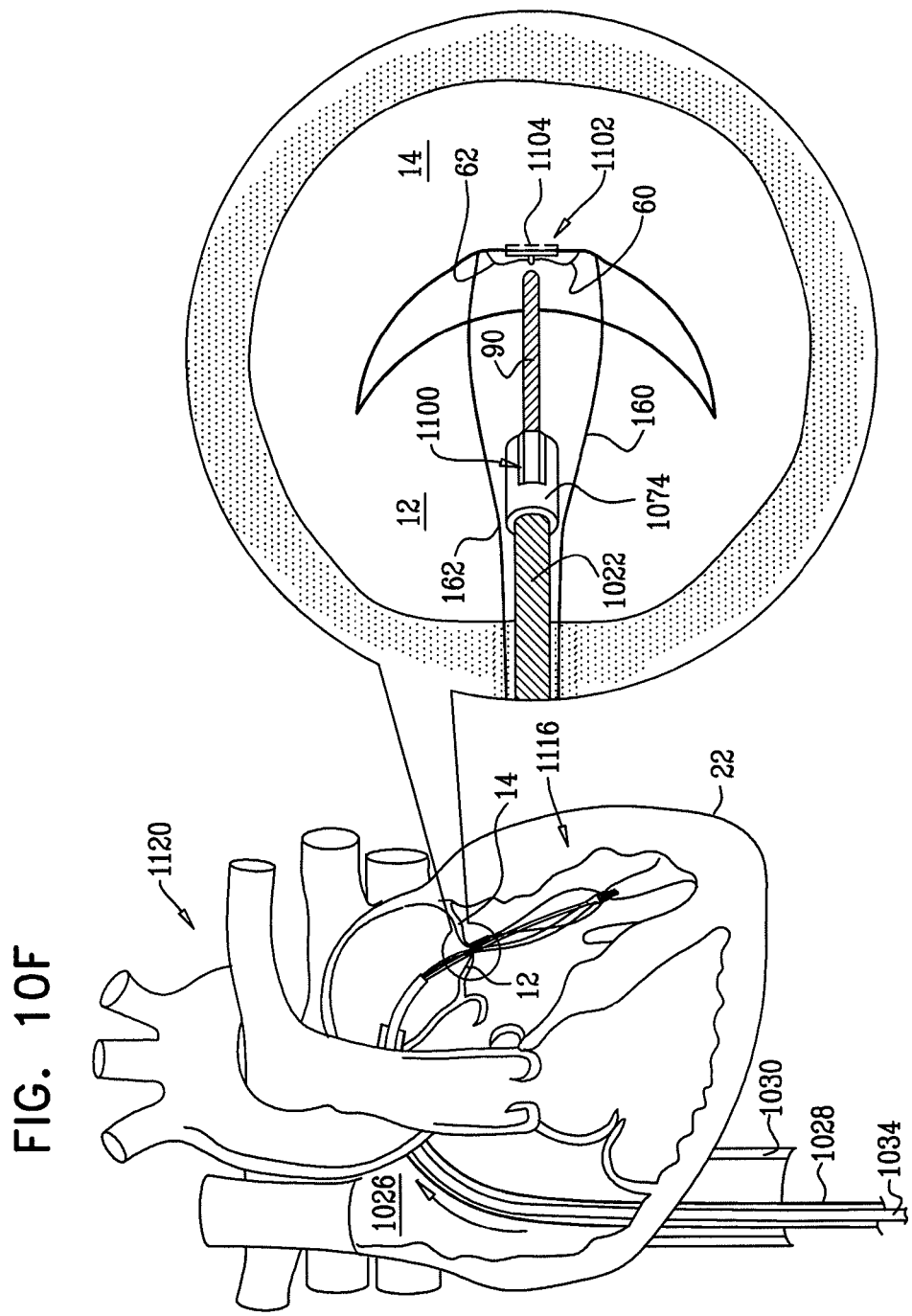
Figure 10G:
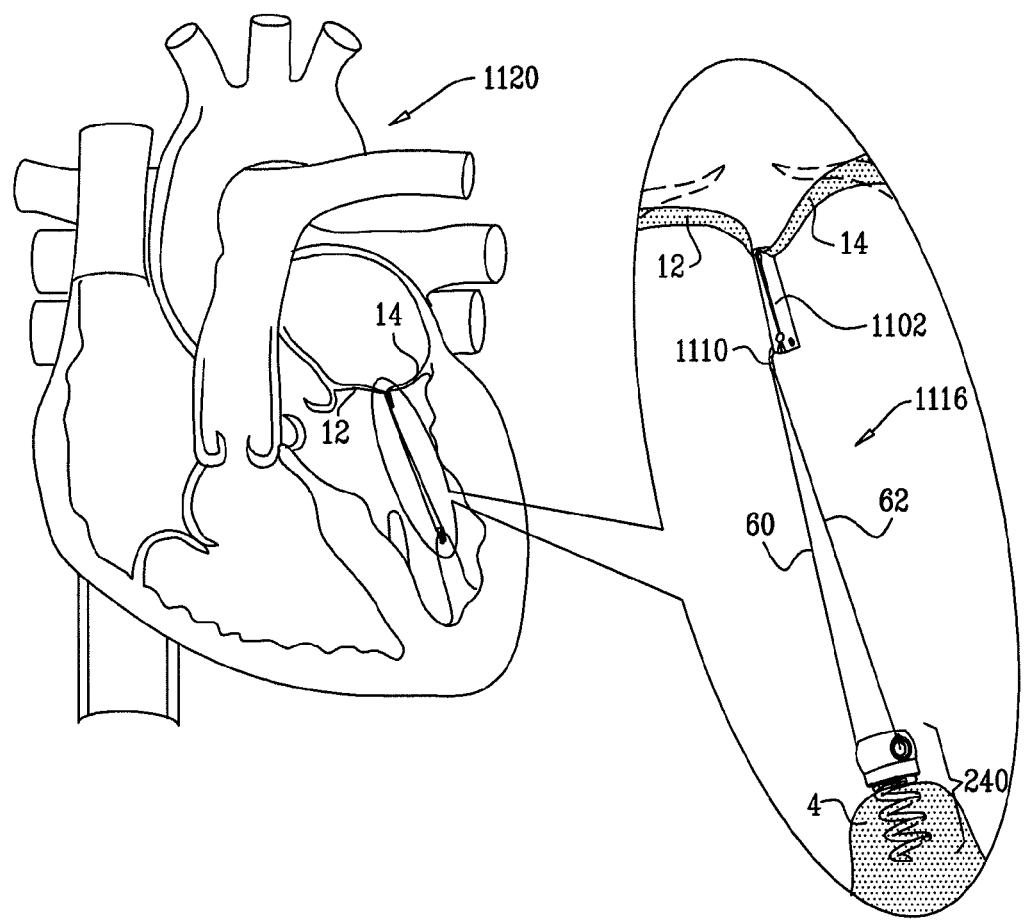

In this embodiment, the one or more leaflet-engaging elements of implant assembly 1116 comprise a clip 1102. Clip 1102 typically is shaped so as to define at least one coupling protrusion 1104. Clip 1102 has a tendency to close, and is initially held open by a cord 1108 that is coupled to a surface of the clip, extends through delivery tool 1120, and is held taught outside of the heart. Once the clip has been advanced to the desired location on the leaflet, as shown in FIG. 10C, cord 1108 is relaxed, allowing the clip to close. The cord is removed, typically by releasing one end thereof and pulling the other end. The positioning of a coupling element holder 1074 between the leaflets helps ensure that the clip engages exactly one of the leaflets. It is noted that in FIG. 10G clip 1102 is shown engaging only a single leaflet (leaflet 14). The clip typically engages the leaflet by clamping the leaflet such that the clip engages atrial and ventricular surfaces of the leaflet. The clip may puncture the leaflet, or may merely press firmly against the leaflet.

Coupling element holder 1074 is shaped to define a groove 1100 which houses clip 1102 during the advancement of tool 1120 toward the ventricle. Groove 1100 functions as a track to facilitate slidable detachment of clip 1102 from holder 1074 following the engaging of clip 1102 to leaflet 14.

Reference is now made to FIGS. 11A-E, which are schematic illustrations of yet another system for implanting and adjusting repair chords, and a transcatheter procedure for implanting the chords in a heart, in accordance with an embodiment of the present invention. Except as described hereinbelow, this system and procedure are similar to the system and procedure described hereinabove with reference to FIGS. 9A-K, and the system and procedure described hereinabove with reference to FIGS. 10A-G.

Figure 11A:
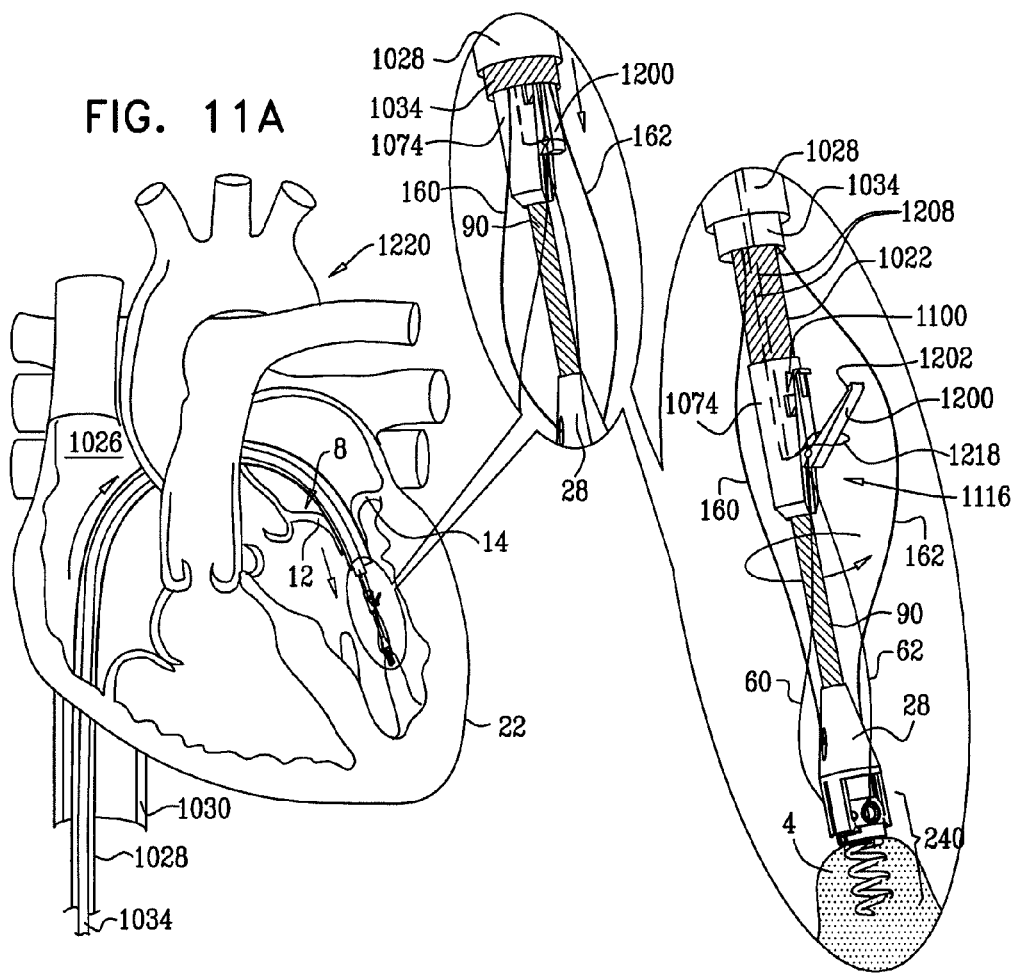
FIGS. 11A-E are schematic illustrations of yet another system for implanting and adjusting repair chords, and a transcatheter procedure for implanting the chords in a heart, in accordance with an embodiment of the present invention.
Figure 11B:
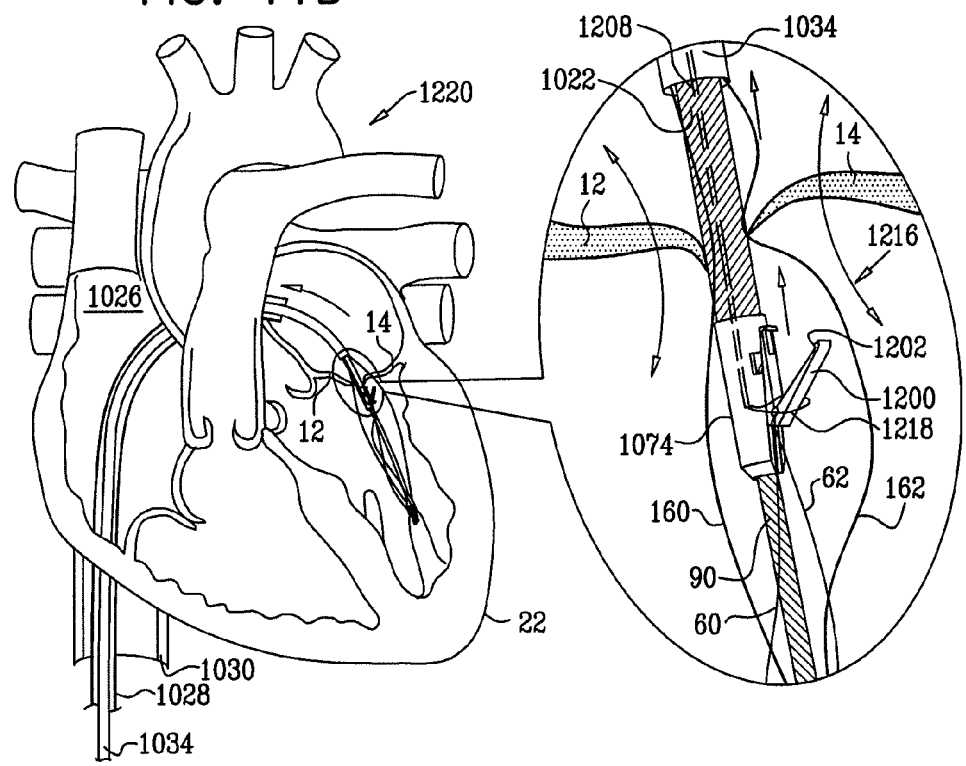
Figure 11C:
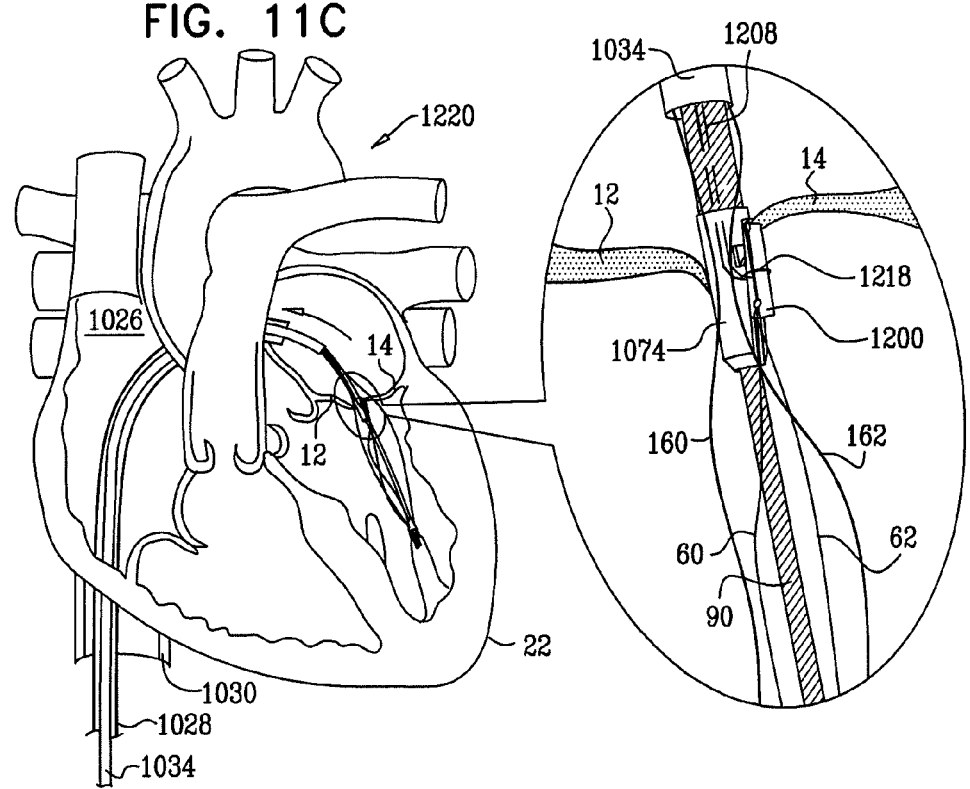
Figure 11D:
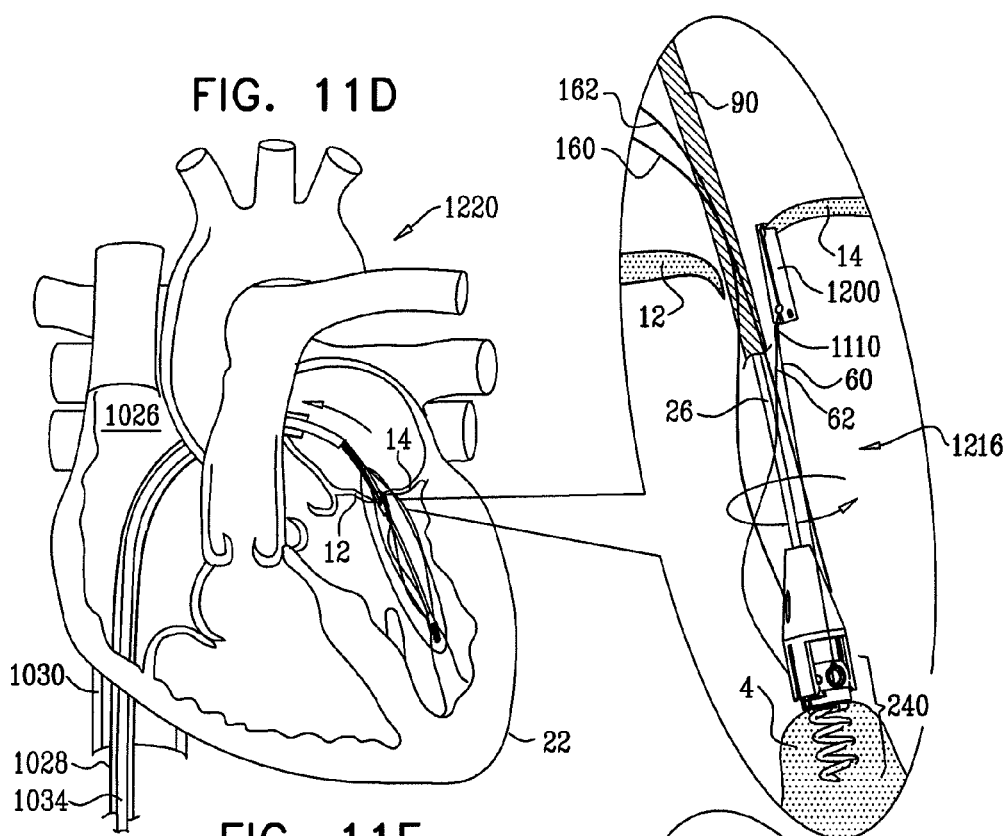
Figure 11E:
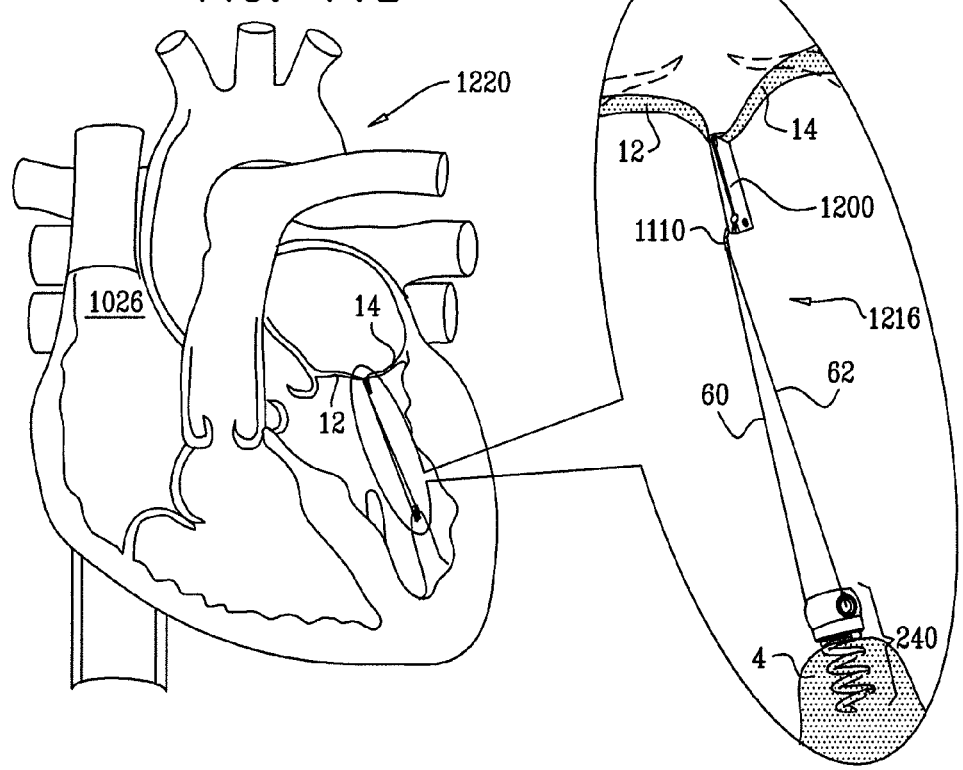
Figure 12A:
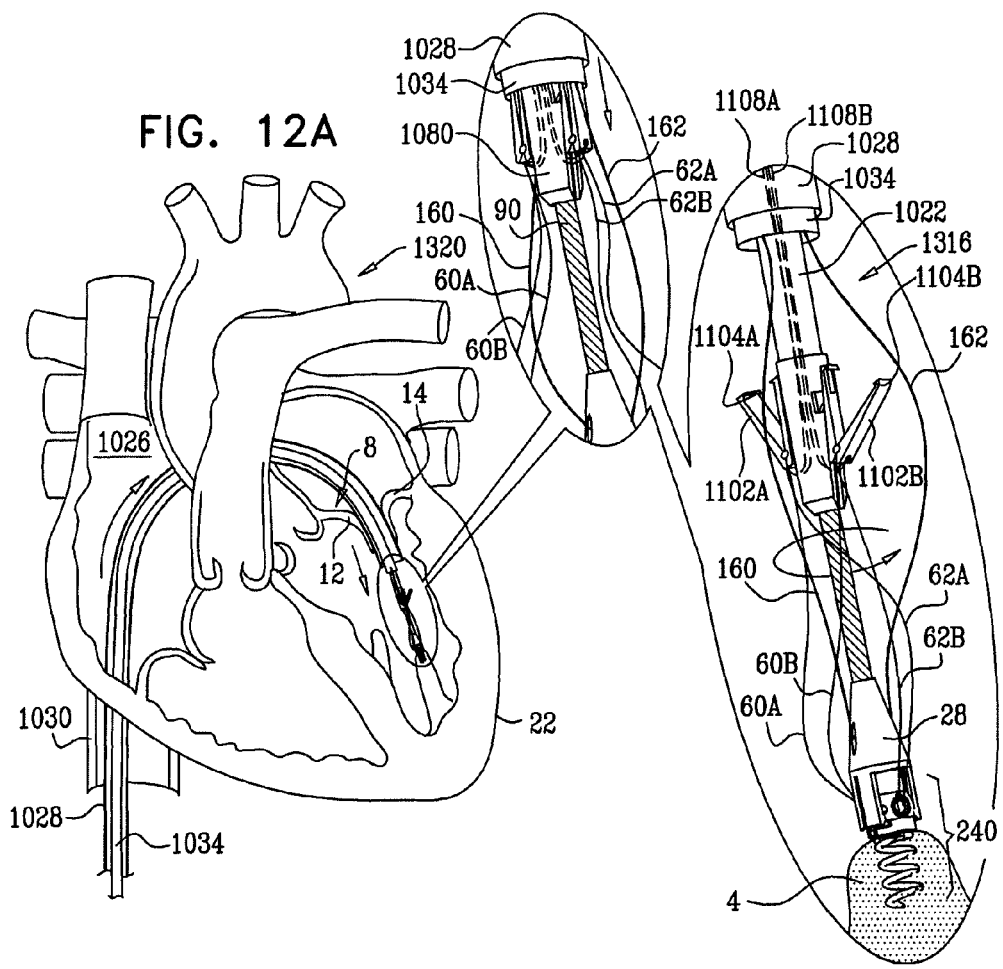
FIGS. 12A-G are schematic illustrations of an additional system for implanting and adjusting repair chords, and a transcatheter procedure for implanting the chords in a heart, in accordance with an embodiment of the present invention.
Figure 12B:
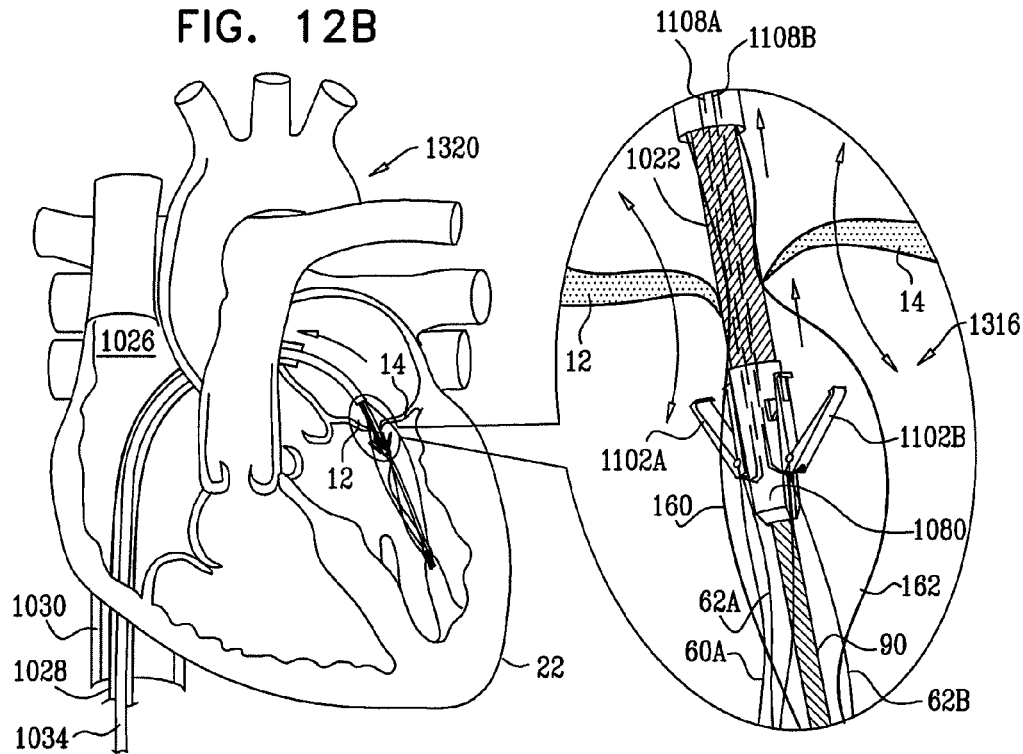
Figure 12C:
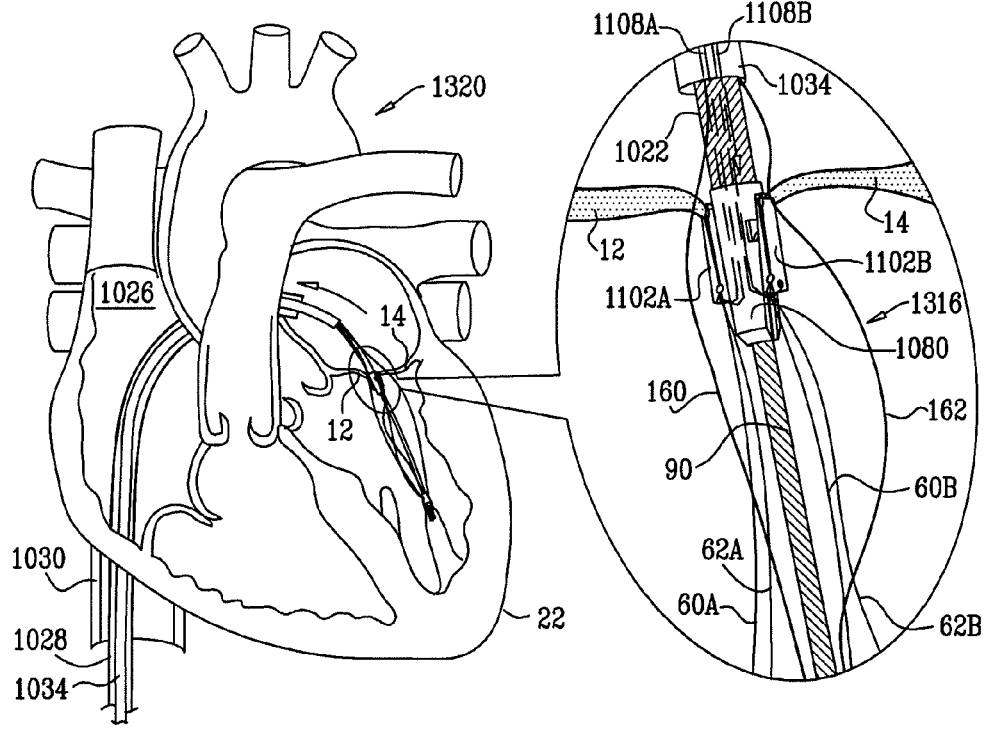
Figure 12D:
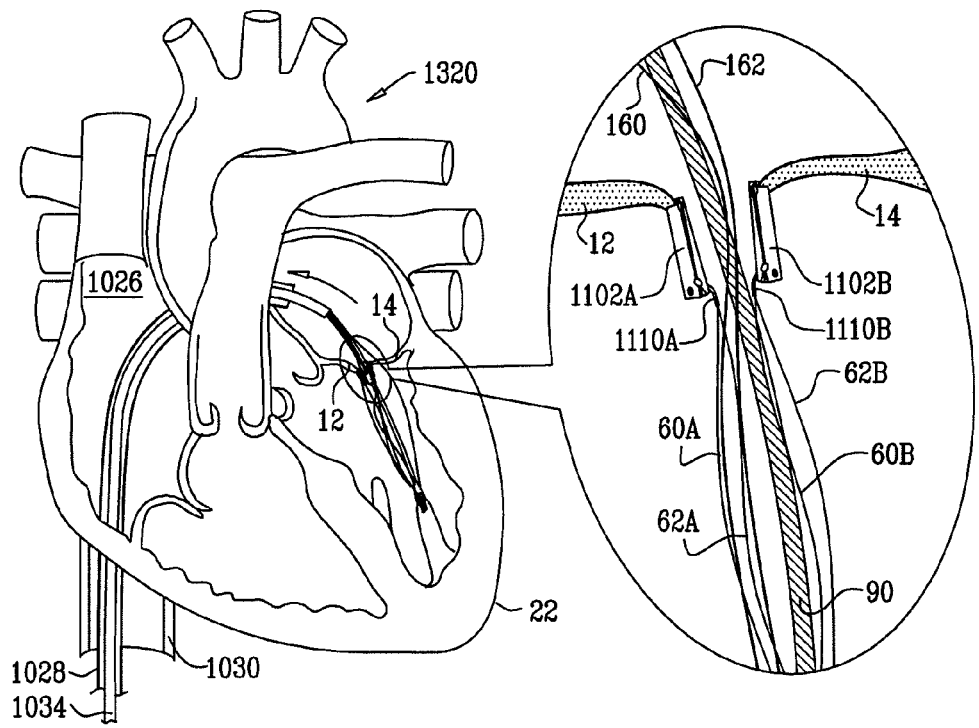
Figure 12E:
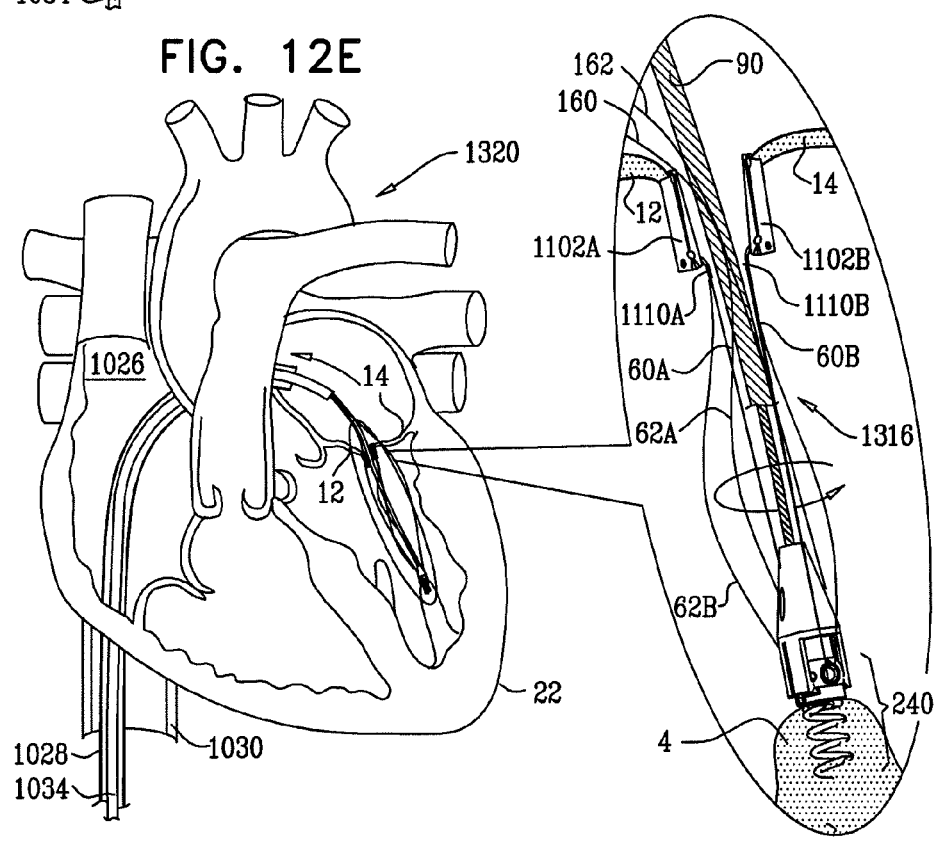
Figure 12F:
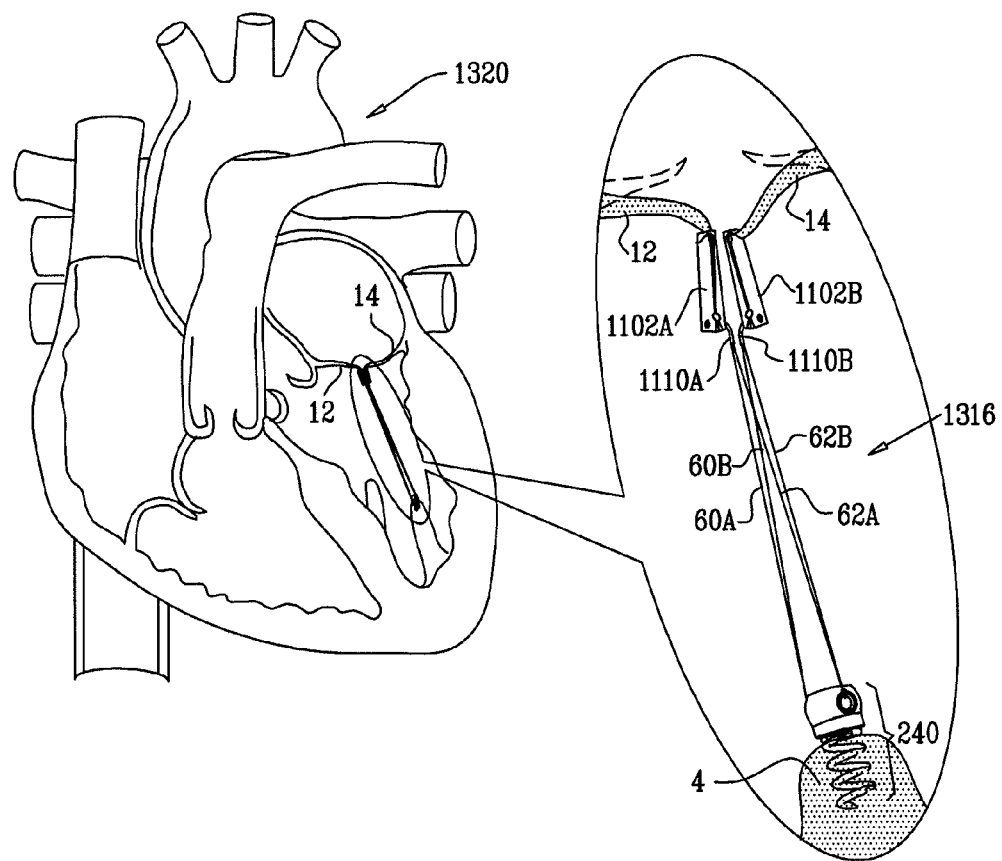
Figure 12G:
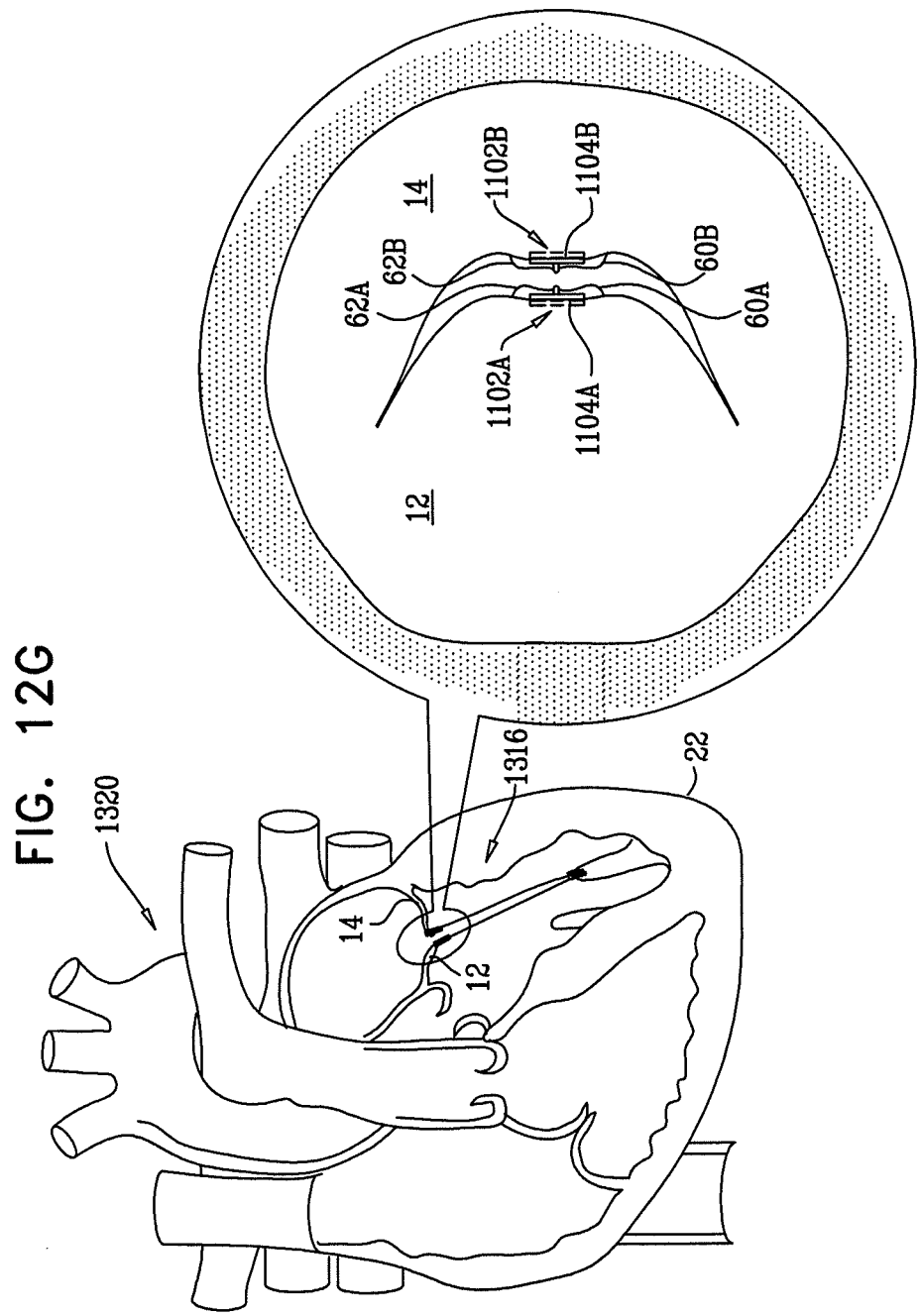

In this embodiment, the one or more leaflet-engaging elements of implant assembly 1116 comprise a clip 1200. Clip 1200 typically is shaped so as to define at least one coupling protrusion 1202. Clip 1200 has a tendency to open. In order to close the clip, a cord 1208 is provided. A distal-most portion 1218 of the cord is looped around clip 1200. Once the clip has been advanced to the desired location on the leaflet, as shown in FIG. 11C, the surgeon pulls on both ends of the cord, thereby causing the clip to become locked close. The cord is removed, typically by releasing one end thereof and pulling the other end. The positioning of coupling element holder 1074 between the leaflets helps ensure that the clip engages exactly one of the leaflets. The clip typically engages the leaflet by clamping the leaflet such that the clip engages atrial and ventricular surfaces of the leaflet. The clip may puncture the leaflet, or may merely press firmly against the leaflet. It is noted that in FIG. 10E clip 1102 is shown engaging only a single leaflet (leaflet 14). For some applications, longitudinal members 60 and 62 are directly coupled to clip 1102, while for other applications the members are indirectly coupled, such as by a hook 1110.

Reference is now made to FIGS. 12A-G, which are schematic illustrations of an additional system for implanting and adjusting repair chords, and a transcatheter procedure for implanting the chords in a heart, in accordance with an embodiment of the present invention. Except as described hereinbelow, this system and procedure are similar to the system and procedure described hereinabove with reference to FIGS. 10A-G. In this embodiment, an implant assembly 1316 comprises two clips 1102A and 1102B, two cords 1108A and 1108B, and two sets of longitudinal members 60A and 62A, and 60B and 62B, coupled to respective ones of the clips. The clips engage respective ones of the leaflets.

In an embodiment of the present invention, the system of FIGS. 12A-G instead comprises two clips 1200, as described hereinabove with reference to FIGS. 11A-E.

Figure 13:
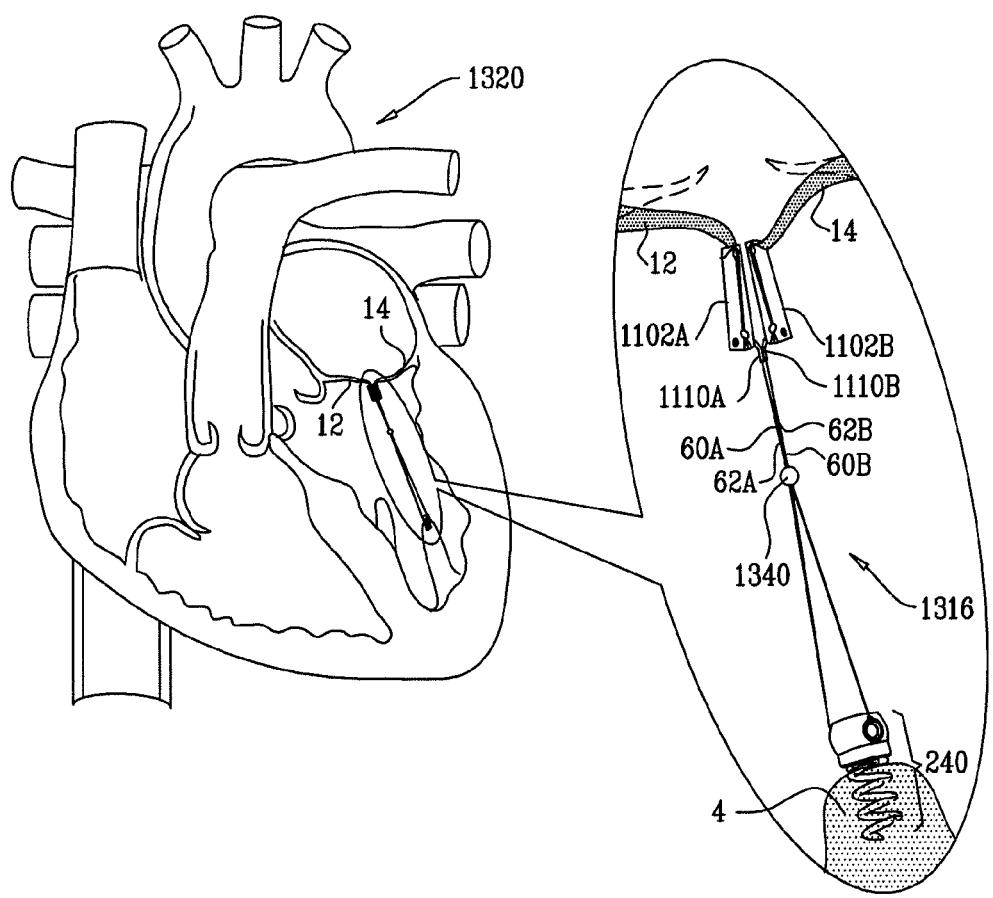
FIG. 13 is a schematic illustration of another configuration of the system of FIGS. 12A-G, in accordance with an embodiment of the present invention.

Reference is made to FIG. 13, which is a schematic illustration of another configuration of the system of FIGS. 12A-G, in accordance with an embodiment of the present invention. In this configuration, implant assembly 1316 further comprises at least one bead 1340, that is threaded over longitudinal members 60A, 62A, 60B, and 62B. The surgeon adjusts the position of the bead along the longitudinal members in order to set the degree to which clips 1102A and 1102B are free to move with respect to one another. Typically, the bead is pulled proximally by the delivery tool used to implant spool assembly 240. Alternatively, the bead may be pulled by shaft 1022. In general, as the bead is positioned closer to the clips, the clips are more constrained in their motion with respect to one another, and the leaflets are drawn closer together. For some applications, the bead comprises a fixation mechanism (e.g., a crimping mechanism), which is configured to fix the bead to the longitudinal members once the bead has been positioned at a desire location along the members.

In an embodiment of the present invention, the bead of FIG. 13 is applied to the two-clip embodiment of the system of FIGS. 12A-G, as described hereinabove.

Reference is now made to FIGS. 14A-E, which are schematic illustrations of yet an additional system for implanting and adjusting repair chords, and a transcatheter procedure for implanting the chords in a heart, in accordance with an embodiment of the present invention. Except as described hereinbelow, this system and procedure are similar to the system and procedure described hereinabove with reference to FIGS. 9A-K.

Figure 14A:
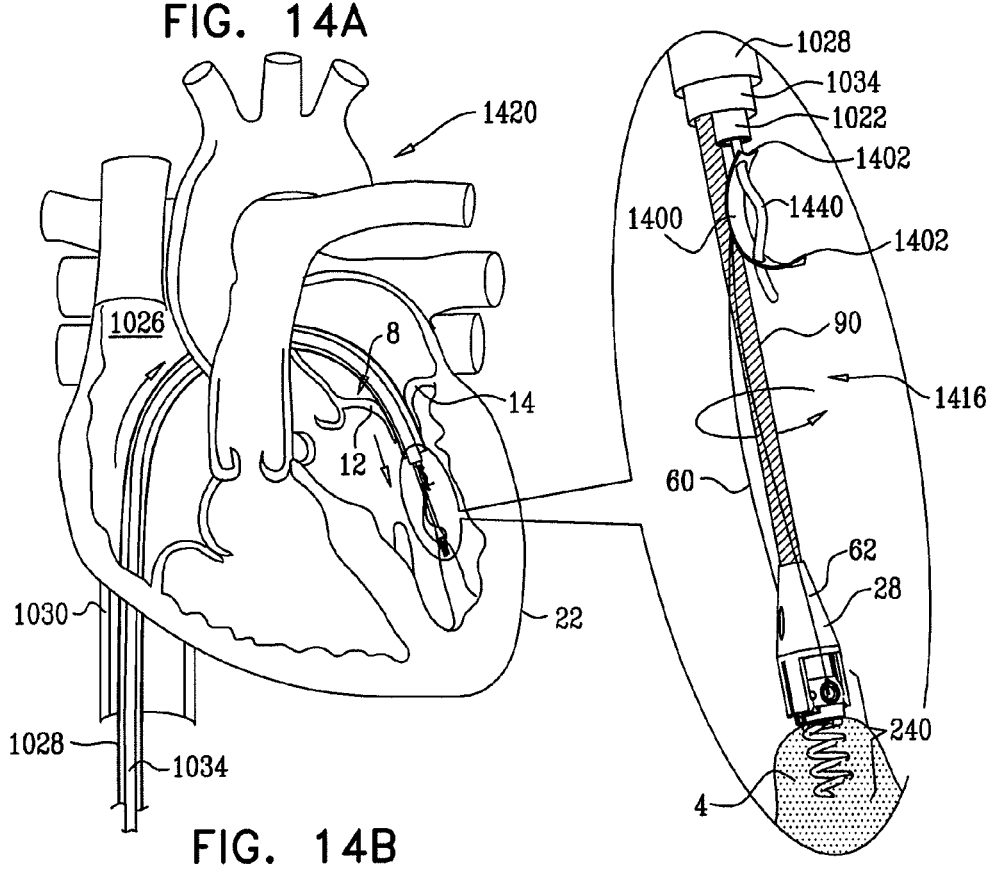
Figure 16A:
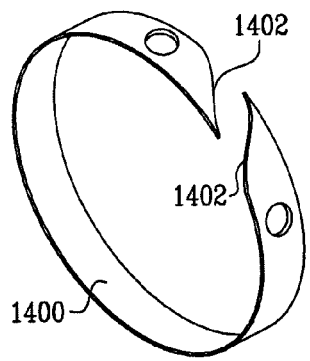
FIGS. 16A-B are schematic illustrations of another configuration of the non-continuous ring of the system of FIGS. 14A-E, in accordance with an embodiment of the present invention.
Figure 16B:
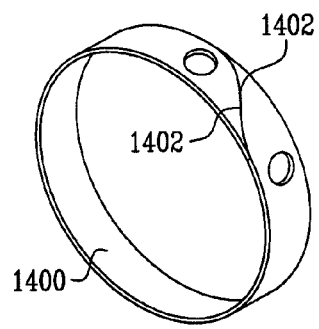

In this embodiment, the one or more leaflet-engaging elements comprise at least one non-continuous ring 1400. Non-continuous ring 1400 is configured to assume extended and annular positions. In the extended position, as shown in FIG. 14A, ends 1402 of the non-continuous ring are separated from one another. In the annular position, as shown in FIG. 14D, the non-continuous ring assumes an annular configuration in which ends 1402 are near one another, e.g., within 0 mm and 1 mm, such as within 0 mm to 0.5 mm, of one another, typically separated only by tissue of the leaflet, or touching one another, such as end-to-end or with the ends overlapping one another along the ring by up to 1 mm, such as shown in FIGS. 16A-B, described hereinbelow. Non-continuous ring 1400 is configured to have a tendency to assume the annular position. A delivery tool 1420 comprises a deforming rod 1440, which is configured to initially hold ring 1400 in the extended position, as shown in FIG. 14A. For example, the ring may be shaped so as to define one or more holes therethrough, through which the deforming rod passes. For some applications, the deforming rod is curved (as shown), while for other applications, the deforming rod is straight (configuration not shown). The deforming rod protrudes from the distal end of surrounding shaft 1022, and is withdrawable into the shaft.

Figure 14B:
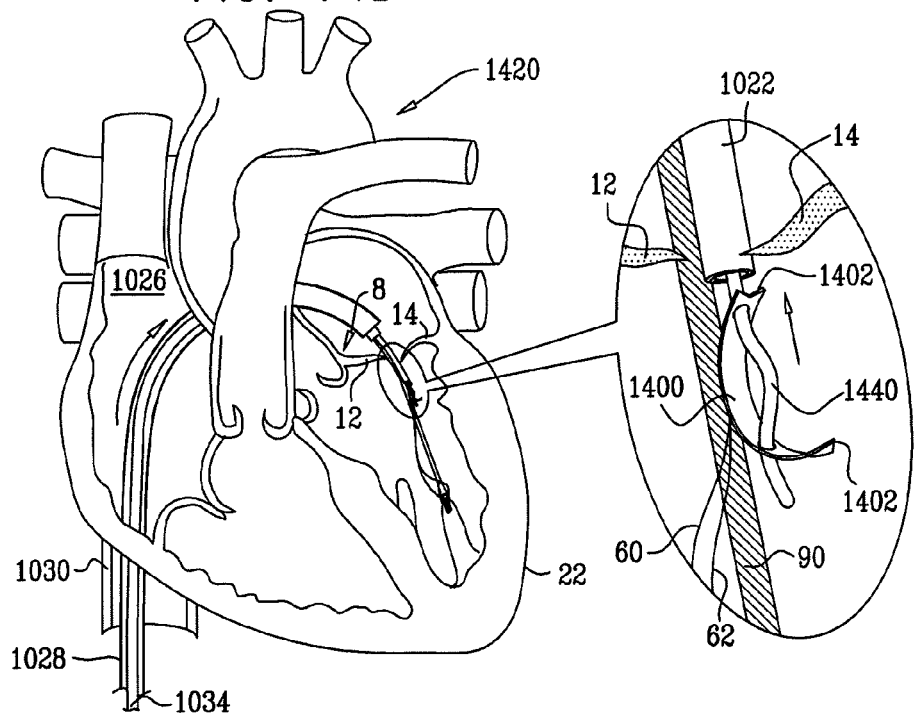
Figure 14E:
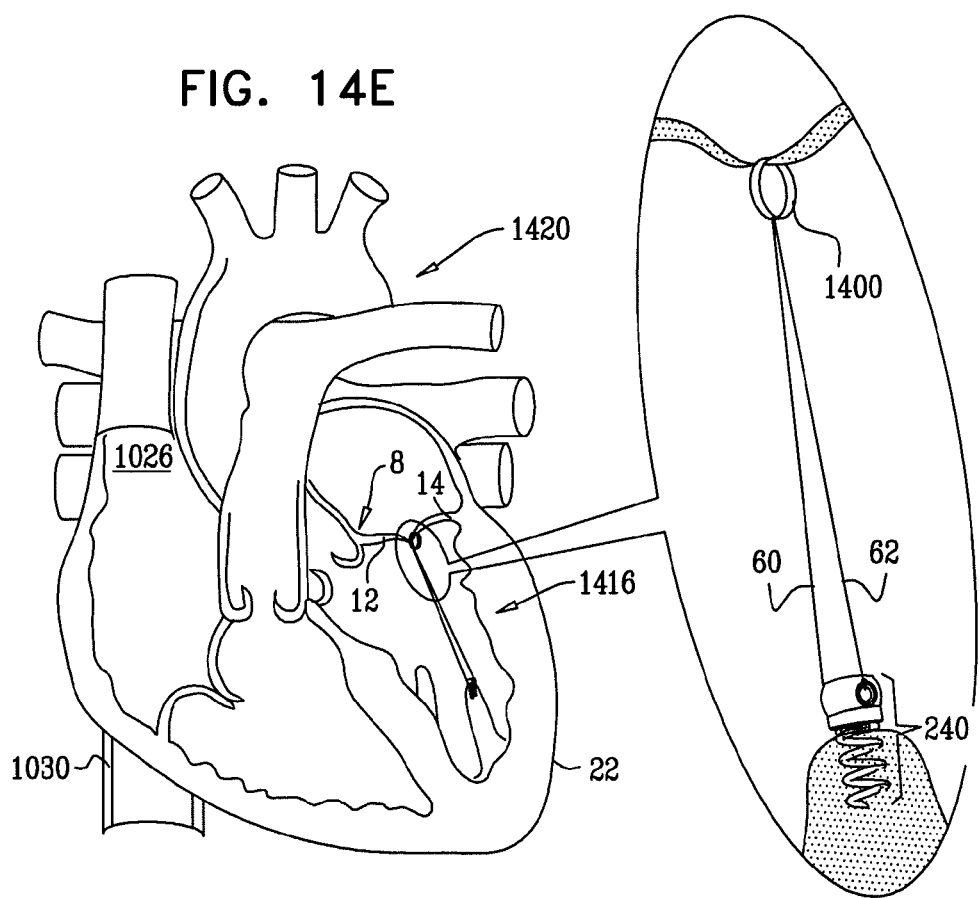

After the anchor of spool assembly 240 has been coupled to tissue of papillary muscle 4, as shown in FIG. 14A, surrounding shaft 1022 is withdrawn proximally toward leaflets 12 and 14, as shown in FIG. 14B. The non-continuous ring is positioned in the vicinity of one of the leaflets, and deforming rod 1440 is withdrawn in a proximal direction into surrounding shaft 1022, the distal end of which pushes against one end of the non-continuous ring, as shown in FIG. 14C. After the deforming rod has been fully separated from the non-continuous ring, the ring assumes the annular position, as shown in FIG. 14D, in which ends 1402, which are generally sharp, engage the leaflet. The ends may puncture the leaflet, or may merely press firmly against the leaflet. Also as shown in FIG. 14D, torque-delivering tool 26 (within central shaft 90) is rotated to rotate spool 46 of spool assembly 240, thereby wrapping longitudinal members 60 and 62 around spool 46, and shortening the effective length of the longitudinal members, as described hereinabove. This shortening has the effect of bringing the prolapsed leaflet (leaflet 14 in the figures) toward the ventricle, as shown in FIG. 14E.

For some applications, one of ends 1402 of the non-continuous ring is shaped so as to define an opening, and the other of the ends is shaped so as to at least partially enter the opening.

Figure 15A:
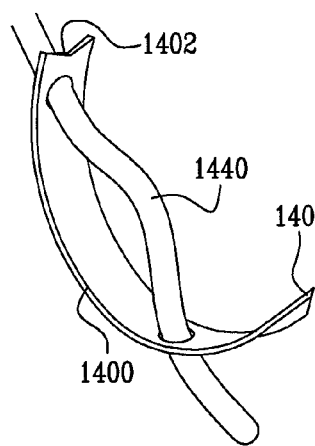
FIGS. 15A-C are schematic illustrations of a non-continuous ring and a deforming rod of the system of FIGS. 14A-E, in accordance with an embodiment of the present invention.
Figure 15B:
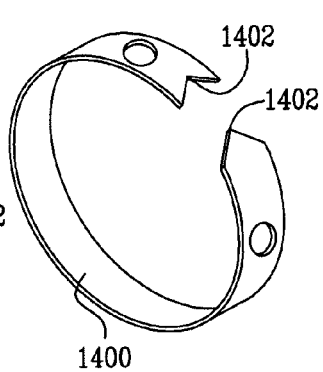
Figure 15C:
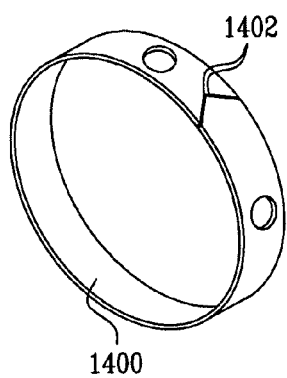

FIGS. 15A-C are schematic illustrations of non-continuous ring 1400 and deforming rod 1440, in accordance with an embodiment of the present invention. As can be seen, ends 1402 of the non-continuous ring are V-shaped. Such a shape enables ring 1400 to either puncture the leaflet or firmly compress a portion of the leaflet between ends 1402.

FIGS. 16A-B are schematic illustrations of another configuration of non-continuous ring 1400, in accordance with an embodiment of the present invention. In this configuration, ends 1402 of the non-continuous ring are curved, such that the ends overlap one another along the ring. Such a shape enables ring 1400 to either puncture the leaflet or firmly compress a portion of the leaflet between ends 1402.

Reference is now made to FIGS. 15A-C and 16A-B. For some applications, rings 1400 described herein may be used as tissue anchors for other portions of tissue of the patient, e.g., the papillary muscle of the patient. For example, ring 1400 may replace helical anchor 50 of assembly 240 so as to facilitate implantation of adjustment mechanism 40 at papillary muscle 4.

Reference is now made to FIGS. 17A-G, which are schematic illustrations of still another system for implanting and adjusting repair chords, and a transcatheter procedure for implanting the chords in a heart, in accordance with an embodiment of the present invention. Except as described hereinbelow, this system and procedure are similar to the system and procedure described hereinabove with reference to FIGS. 9A-K.

In this embodiment, the one or more leaflet-engaging elements comprise at least one butterfly clip 1500. A distal end of a surrounding shaft 1522 is shaped so as to initially hold the butterfly clip in a collapsed position. Petals 1523 of the butterfly comprise a superelastic material (e.g., Nitinol) that causes the butterfly to open when released from surrounding shaft 1522.

Figure 17A:
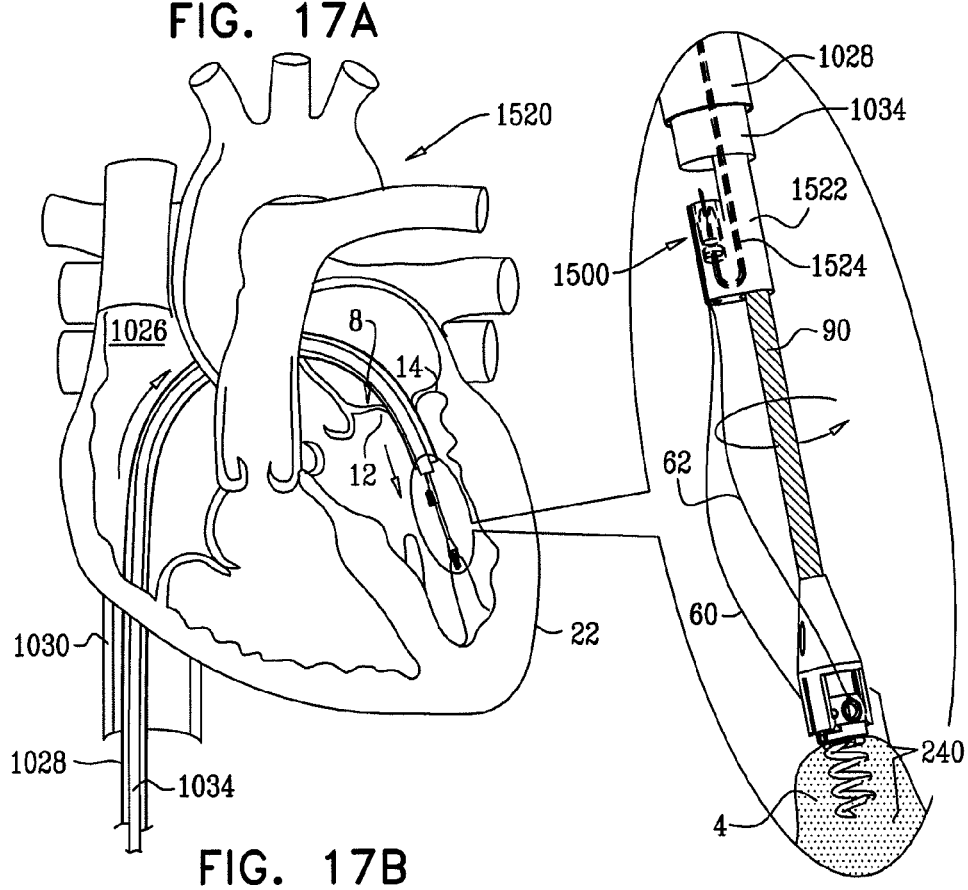

During the transcatheter implantation procedure, as shown in FIG. 17A, a delivery tool 1520 and the implant assembly are advanced into the left ventricle. All or a portion of the delivery tool is rotated (e.g., central shaft 90) in order to screw the helical anchor of spool assembly 240 into tissue of papillary muscle 4.

Figure 17B:
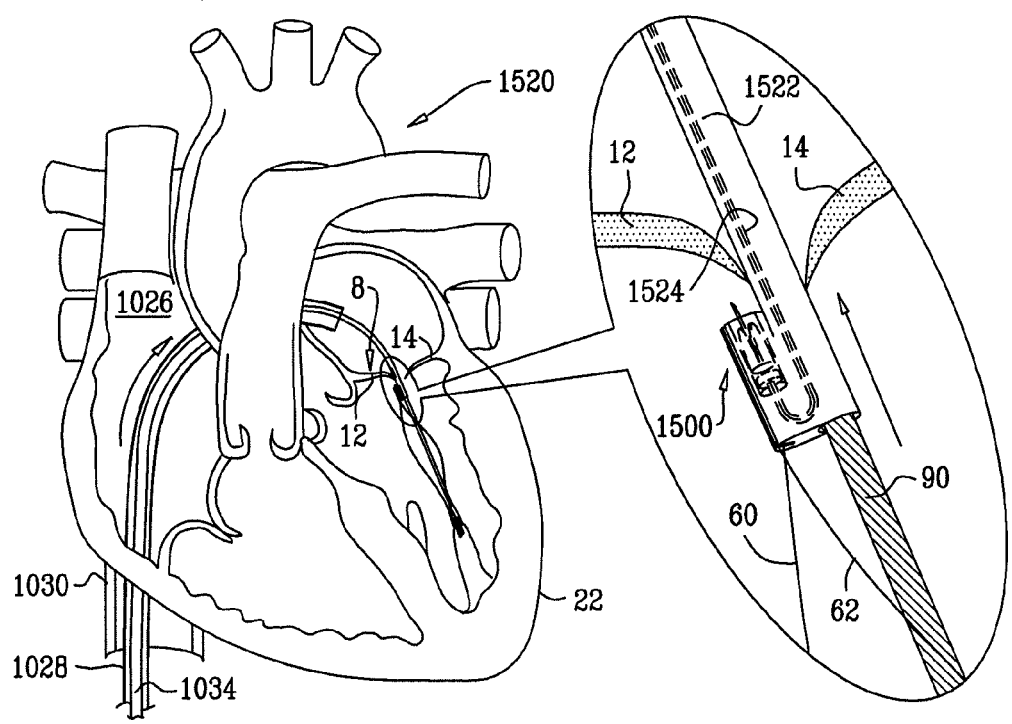

As shown in FIG. 17B, surrounding shaft 1522 is withdrawn proximally toward the left atrium, while maintaining the distal end of central shaft 90 in place and within the ventricle. At this step of the procedure, butterfly clip 1500 remains in the ventricle.

Figure 17C:
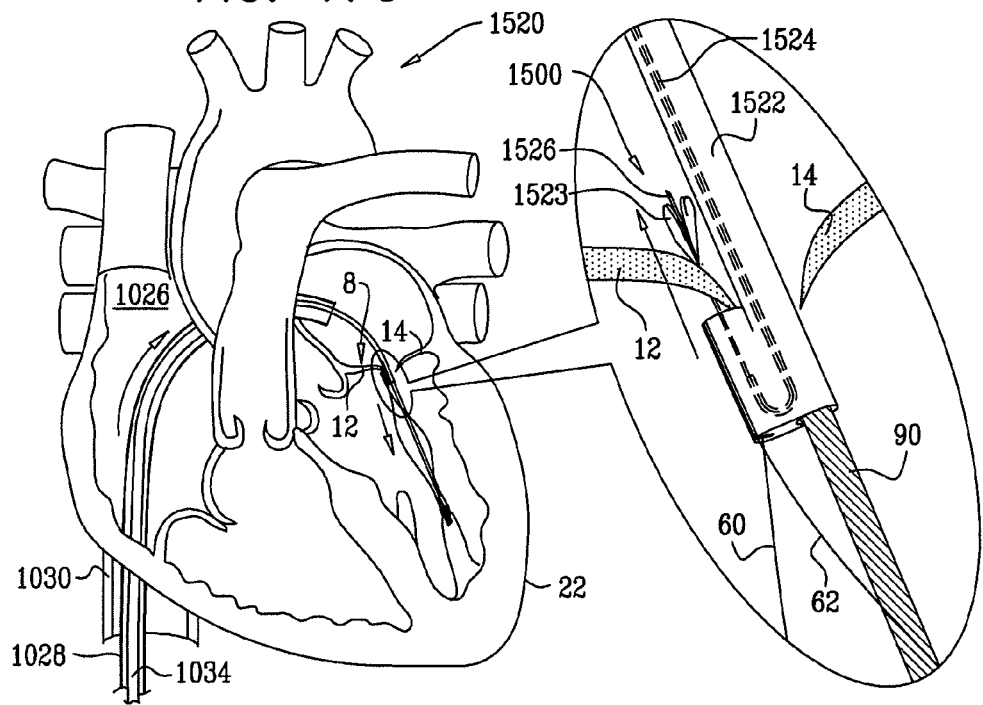
Figure 17D:
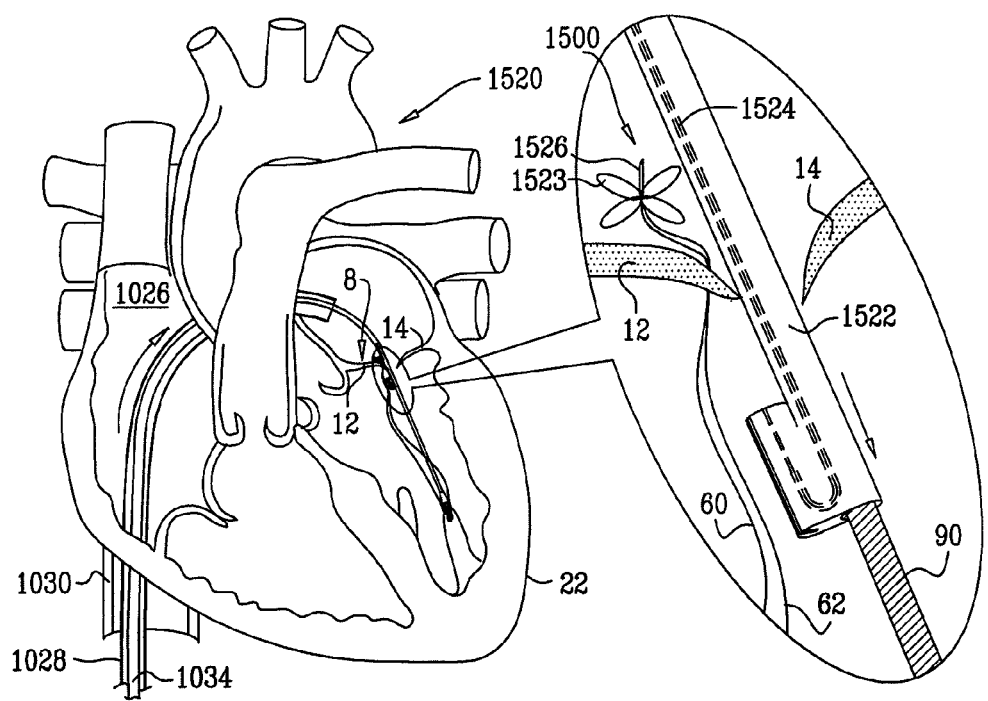

As shown in FIG. 17C, one or more stiff cords 1524 that pass through surrounding shaft 1522 push the butterfly clip out of the distal end of the shaft and against the ventricular surface of one of the leaflets, so that the butterfly clip penetrates the ventricular surface and emerges from the atrial surface of the leaflet. The butterfly clip typically comprises a sharp needle 1526 to aid with this penetration. As shown in FIG. 17D, upon emerging from the atrial surface, the butterfly clip, because of its superelastic properties, unfolds, thereby coupling the clip to the leaflet.

Figure 17E:
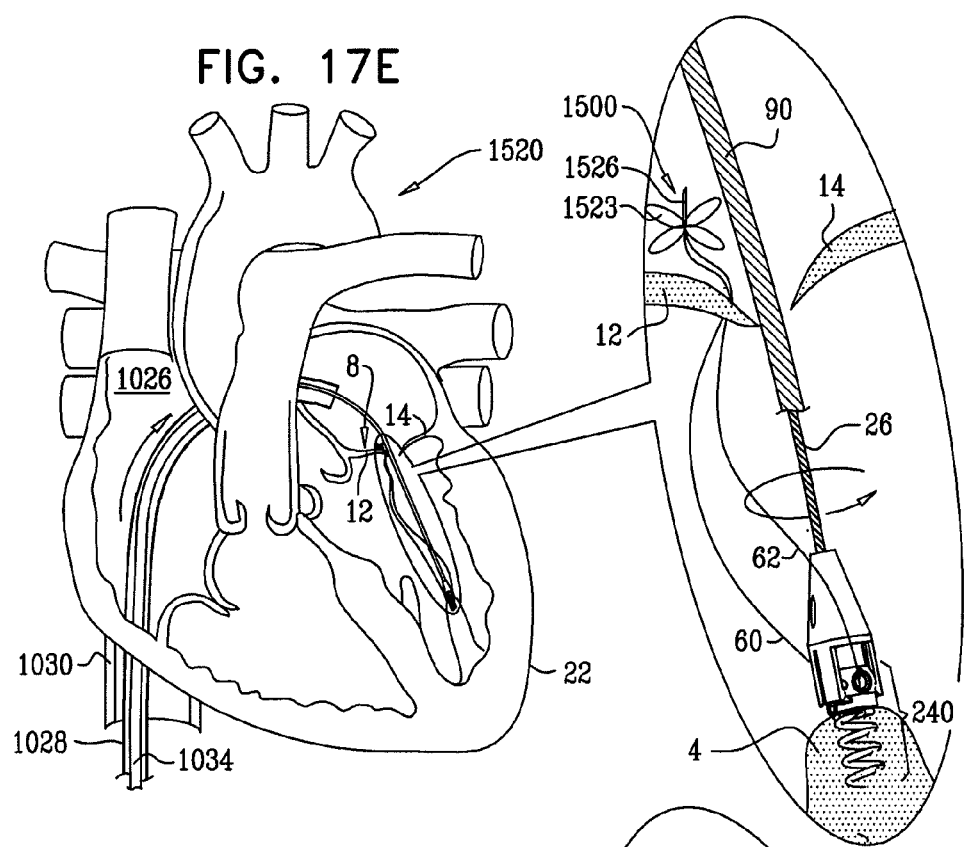
Figure 17F:
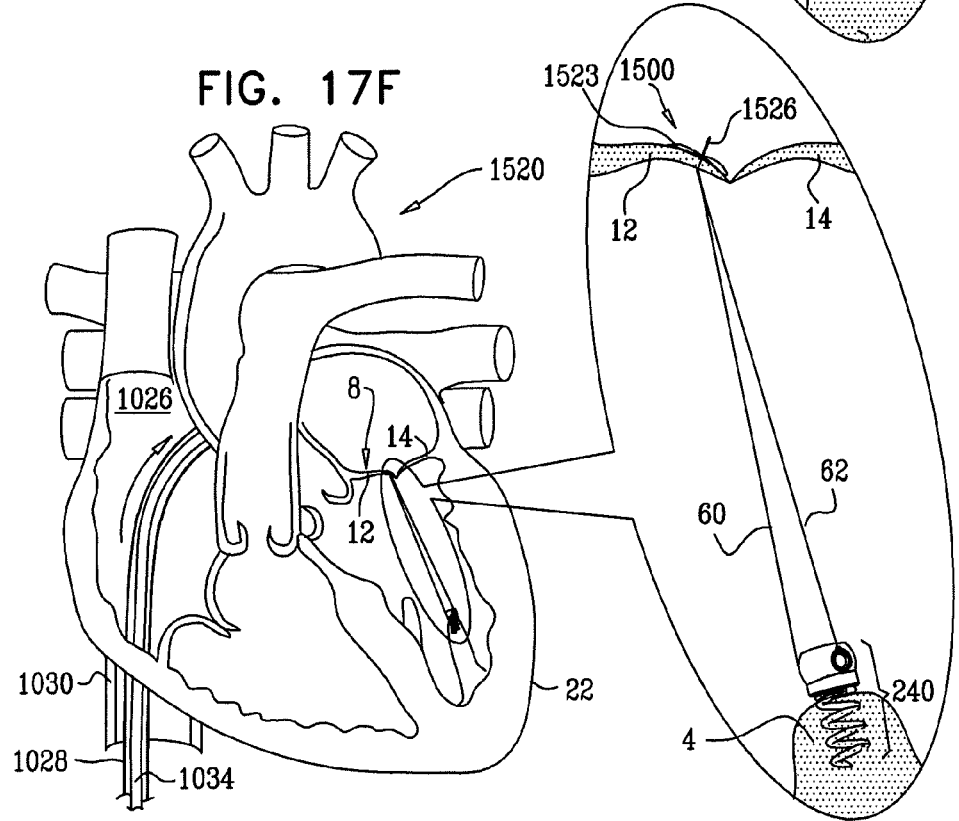

As shown in FIG. 17E, torque-delivering tool 26 (within central shaft 90) is rotated to rotate spool 46 of spool assembly 240, thereby wrapping longitudinal members 60 and 62 around spool 46, and shortening the effective length of the longitudinal members, as described hereinabove. This shortening has the effect of tightening butterfly clip 1500 against the atrial surface of the leaflet (as shown in FIG. 17F), and bringing the prolapsed leaflet (leaflet 14 in the figures) toward the ventricle.

Delivery tool 1520 is withdrawn from the heart, leaving the implant assembly implanted in the left ventricle and leaflet, as shown in FIG. 17K.

Reference is now made to FIGS. 18A-D, which are schematic illustrations of yet another system for implanting and adjusting repair chords, and a transcatheter procedure for implanting the chords in a heart, in accordance with an embodiment of the present invention. Except as described hereinbelow, this system and procedure are similar to the system and procedure described hereinabove with reference to FIGS. 9A-K.

Figure 18A:
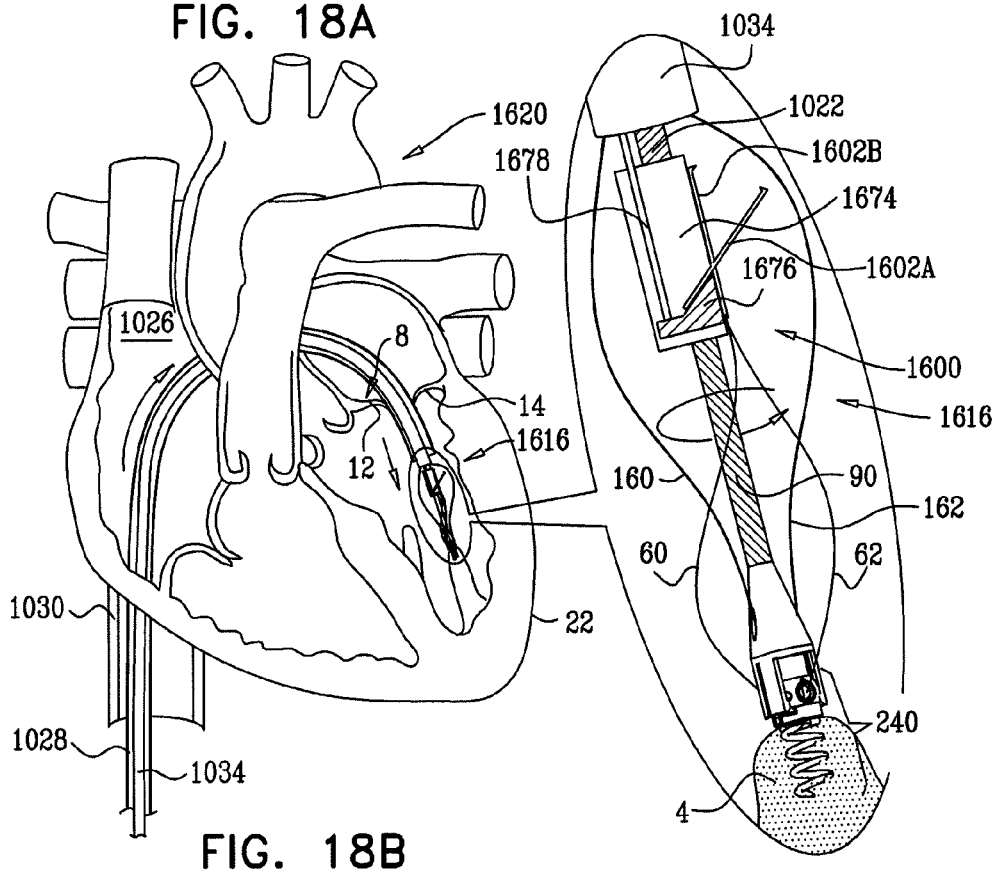
FIGS. 18A-D are schematic illustrations of yet another system for implanting and adjusting repair chords, and a transcatheter procedure for implanting the chords in a heart, in accordance with an embodiment of the present invention.
Figure 18B:
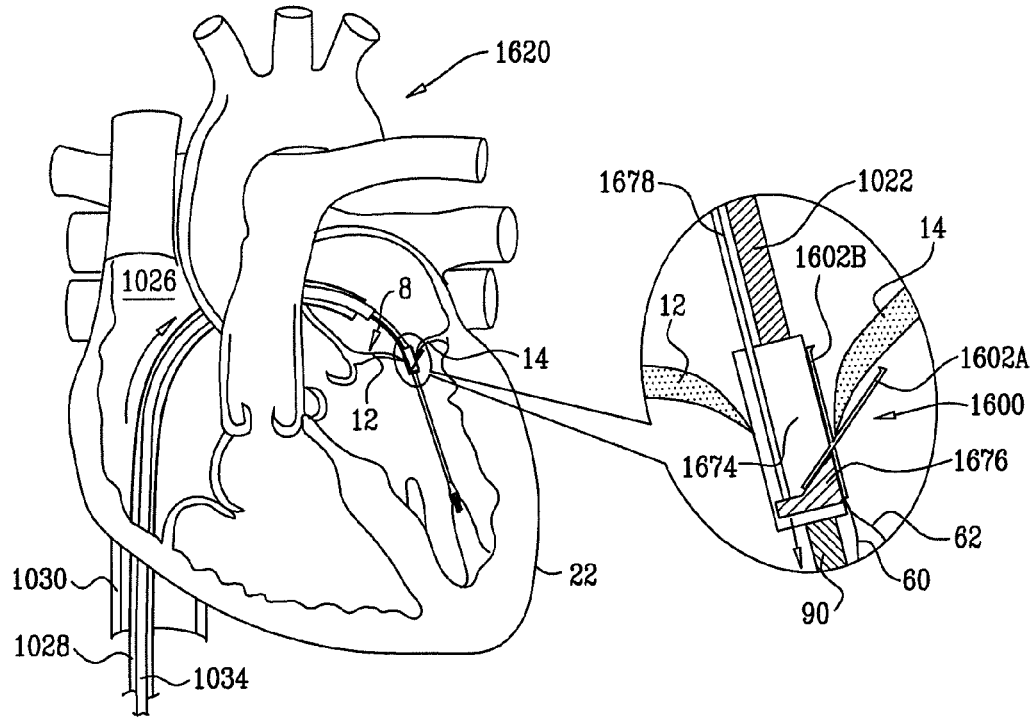
Figure 18C:
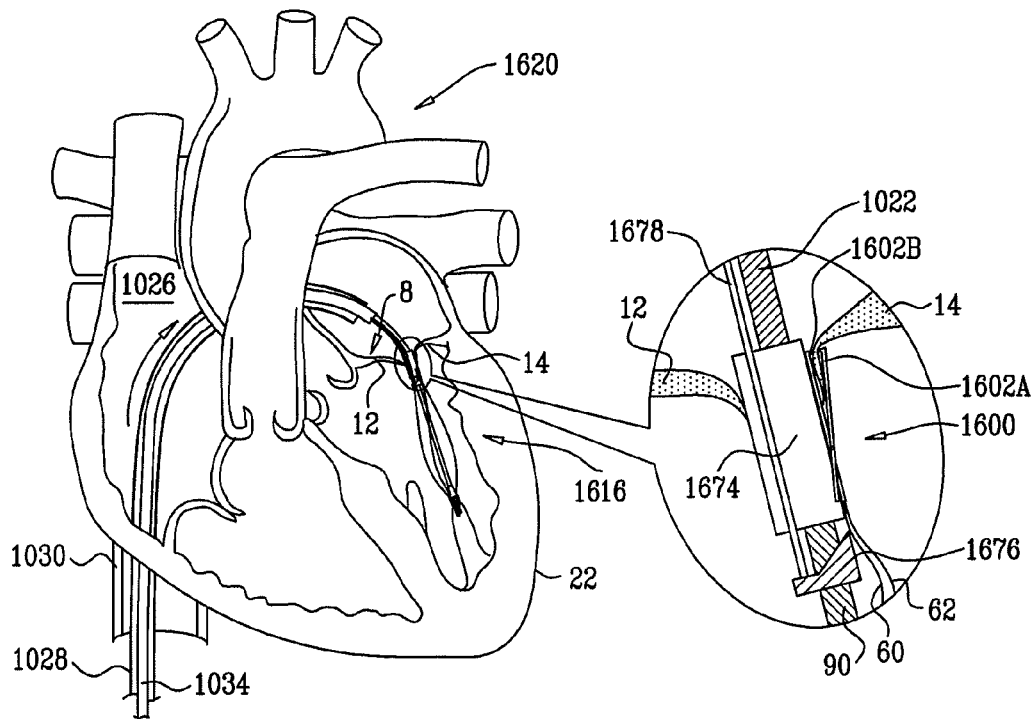
Figure 18D:
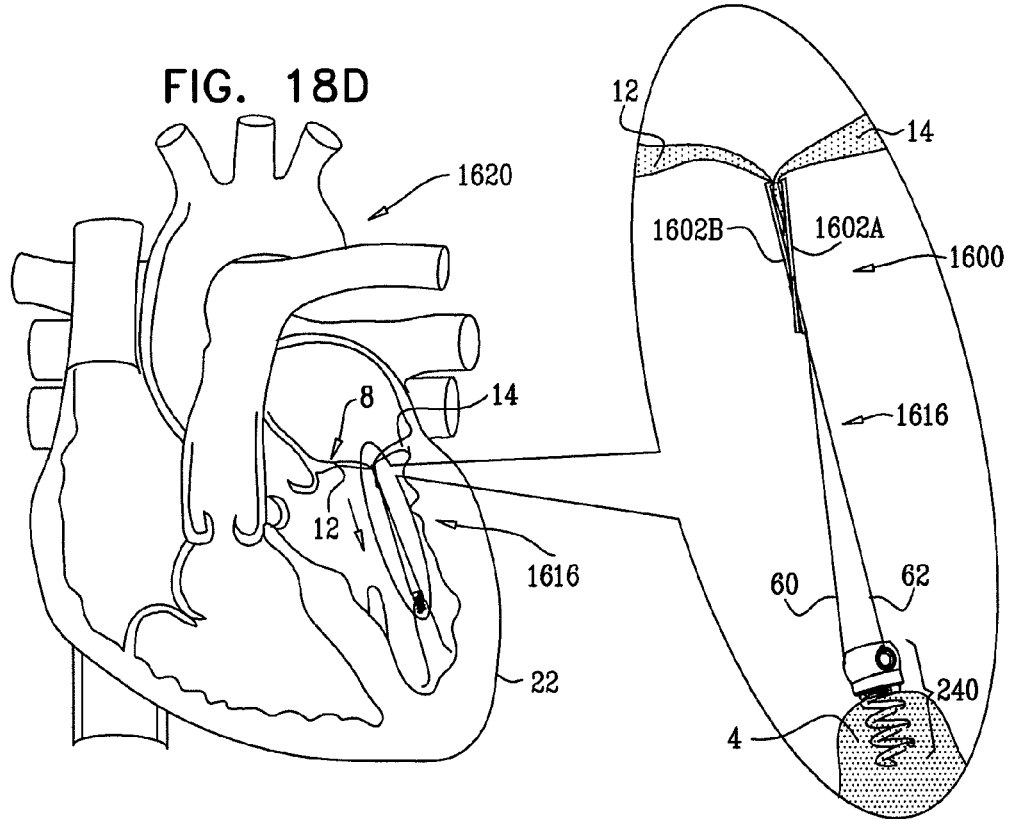

In this embodiment, the one or more leaflet-engaging elements comprise at least one clip 1600 that comprises two jaws 1602A and 1602B, which are configured to assume a closed position when in a resting state. For example, clip 1600 may comprise a spring configured to close the jaws (spring not shown in figures). A coupling element holder 1674 of surrounding shaft 1022 comprises a restraining element 1676 that is configured to hold the jaws separated and the clip in an open position. For some applications, the restraining element is positioned between the non-coupling ends of the jaws beyond the pivot. Pushing restraining element 1676 away from the jaws releases the jaws, allowing them to assume their resting closed position. For example, the restraining element may be configured to be pushed in a distal direction, as shown in FIG. 18B, such as by a rod 1678.

Figure 19:
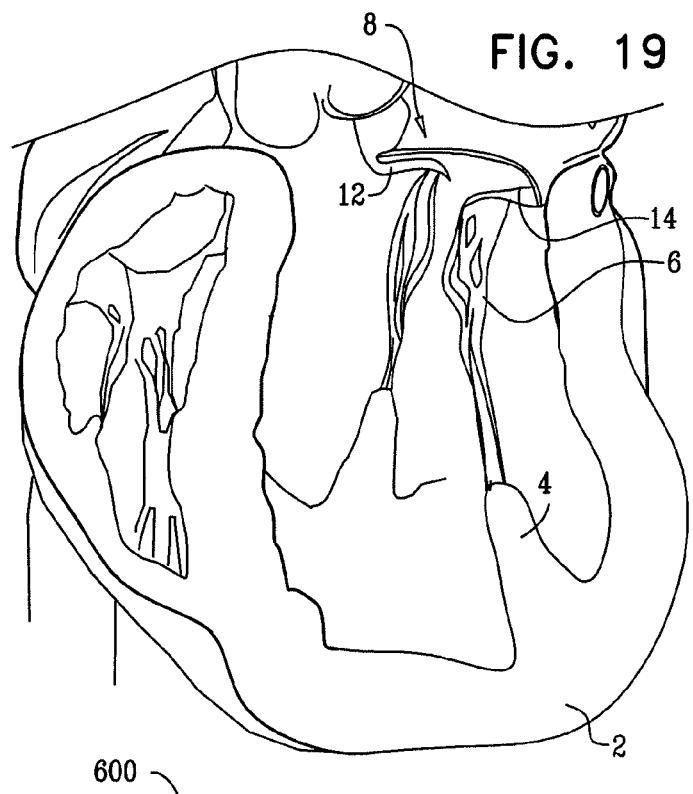

Reference is now made to FIGS. 19, 20A-B, and 21 which are schematic illustrations of respective systems for repairing malpositioning of the wall of the ventricle of the patient, in accordance with respective embodiments of the present invention. FIG. 19 is a schematic illustration of heart 2 in a weakened state in which the wall of the left ventricle is malpositioned and weakened. As a result, leaflets 12 and 14 of mitral valve 8 are malpositioned and are distanced from one another.

Figure 20A:
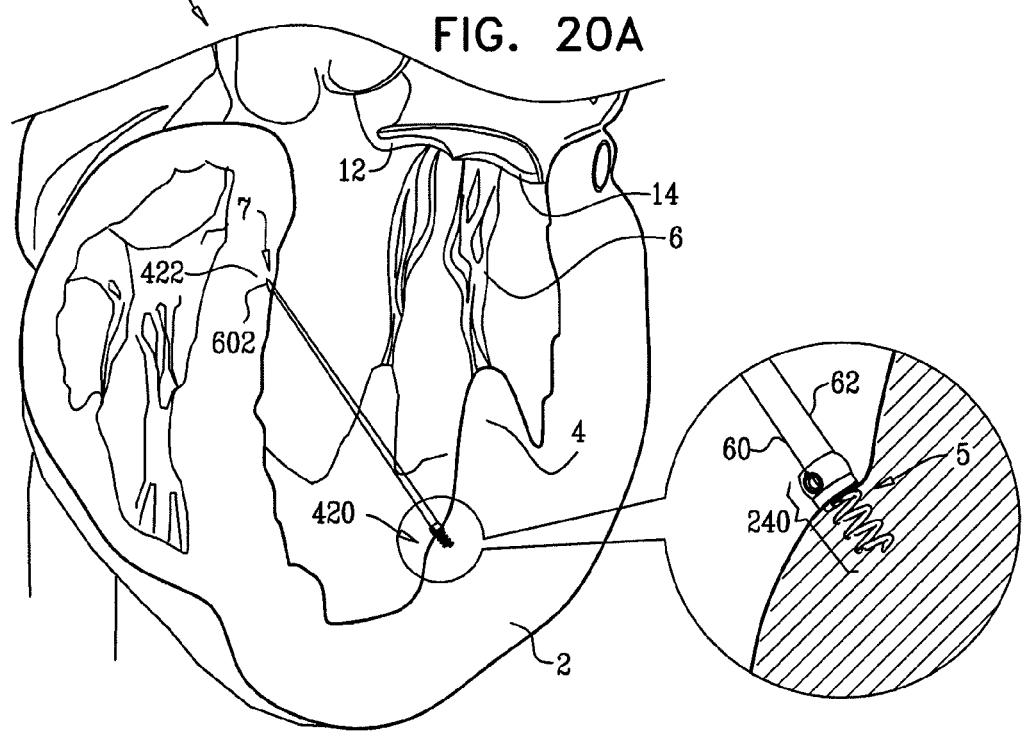

FIG. 20A shows system 600 comprising spool assembly 240 implanted at a first portion 420 of heart tissue which faces and surrounds the left ventricle of heart 2. First implantation site 5 thus comprises first portion 420 of heart tissue. Spool assembly 240 is implanted via tool 20 at site 5 in a manner as described hereinabove with reference to FIGS. 5A-G. The free ends of longitudinal members 60 and 62 are coupled to a second portion 422 of heart tissue which faces and surrounds the left ventricle of heart 2. Second implantation site 7 thus comprises second portion 422 of heart tissue, e.g., at the septum, by way of illustration and not limitation. The free ends of longitudinal members 60 and 62 are coupled to the heart tissue using any suitable attachment means 602, e.g., sutures, knotting, or tissue anchors such as helical anchors. Spool 46 of adjustment mechanism 40 is rotated by tool 20, as described hereinabove, thereby pulling tight longitudinal members 60 and 62 and thereby reducing a length of longitudinal members 60 and 62 between first and second implantation sites 5 and 7. In response to the pulling of longitudinal members 60 and 62, first and second portions 420 and 422 of the heart tissue are pulled toward one another. Consequently, the dimensions of the heart wall are restored to physiological dimensions, and leaflets 12 and 14 are drawn toward one another.

FIG. 20B shows system 700 for adjusting a distance between two portions of a heart wall of the left ventricle of the patient. Longitudinal members 60 and 62 are coupled at first portions thereof to spool 46 of adjustment mechanism 40. Respective free ends of each member 60 and 62 are coupled to opposing first and second portions of the heart wall which faces and surrounds the ventricular lumen of heart 2. The free end of longitudinal member 62 is coupled to first implantation site 5 using a first helical anchor 750 by way of illustration and not limitation. For example, the free end of longitudinal member 62 is coupled to first implantation site 5 using sutures, knots, or any tissue anchor known in the art. The free end of longitudinal member 60 is coupled to second implantation site 7 using a second helical anchor 750 by way of illustration and not limitation. For example, the free end of longitudinal member 60 is coupled to second implantation site 7 using sutures, knots, or any tissue anchor known in the art. In such a configuration, adjustment mechanism 40 is disposed between longitudinal members 60 and 62 and is not directly coupled to heart tissue.

Following the attaching of longitudinal members 60 and 62 to implantation sites 5 and 7, respectively, spool 46 of adjustment mechanism 40 may be rotated using tool 20, in a manner as described hereinabove. As described hereinabove, using tool 20, spool 46 of adjustment mechanism 40 is rotated in order to adjust a distance between first and second implantation sites 5 and 7. Responsively, the first and second portions of the ventricle wall are drawn together. Consequently, the dimensions of the heart wall are restored to physiological dimensions, and leaflets 12 and 14 are drawn toward one another.

FIG. 21 is a schematic illustration of a system 800 for adjusting a distance between two portions of a heart wall of the left ventricle of the patient. System 800 comprises a tensioning device 802 coupled at a first end thereof to spool assembly 240. In a manner as described hereinabove, using tool 20, spool assembly 240 is implanted at first implantation site 5 in a first portion of tissue of the heart wall that faces and surrounds the ventricular lumen. The free end, i.e., second portion, of tensioning device 802 is attached at second implantation site 7 to a second portion of tissue of the heart wall that faces and surrounds the ventricular lumen. The free end of tensioning device 802 is implanted in heart tissue using a helical anchor by way of illustration and not limitation. For example, the free end of tensioning device 802 may be coupled to second implantation site 7 using sutures, knots, or any tissue anchor known in the art.

Tensioning device 802 comprises a flexible material, e.g., ePTFE or nitinol, and is shaped to define a coiled portion 806 that has a length of between 20 mm and 50 mm and a diameter of between 0.5 mm and 3.0 mm. Tensioning device 802 comprises wire/suture portions 804 on either side of coiled portion 806.

As described hereinabove, using tool 20, spool 46 of adjustment mechanism 40 is rotated in order to adjust a distance between first and second implantation sites 5 and 7. As spool 46 is rotated in a first direction thereof, suture portion 804 that is disposed adjacently to spool assembly 240 is wrapped around spool 46. Tensioning device 802 is tightened and shortened in response to the wrapping of portion 804 around spool 46. As device 802 is tightened, a force is applied to coiled portion 806 of tensioning device 802. Coiled portion 806 applies a supplemental pulling force to help pull the opposing first and second portions of the ventricle wall toward one another. Consequently, the dimensions of the heart wall are restored to physiological dimensions, and leaflets 12 and 14 are drawn toward one another.

Reference is again made to FIGS. 19-20. It is to be noted that the scope of the present invention includes the use of systems 600, 700, and 800 for adjusting a distance between any two portions of the heart and not just opposing portions, as described hereinabove. For example, first and second implantation sites 5 and 7 may be on the same side, e.g., the septum, of the wall of the heart.

Figure 22A:
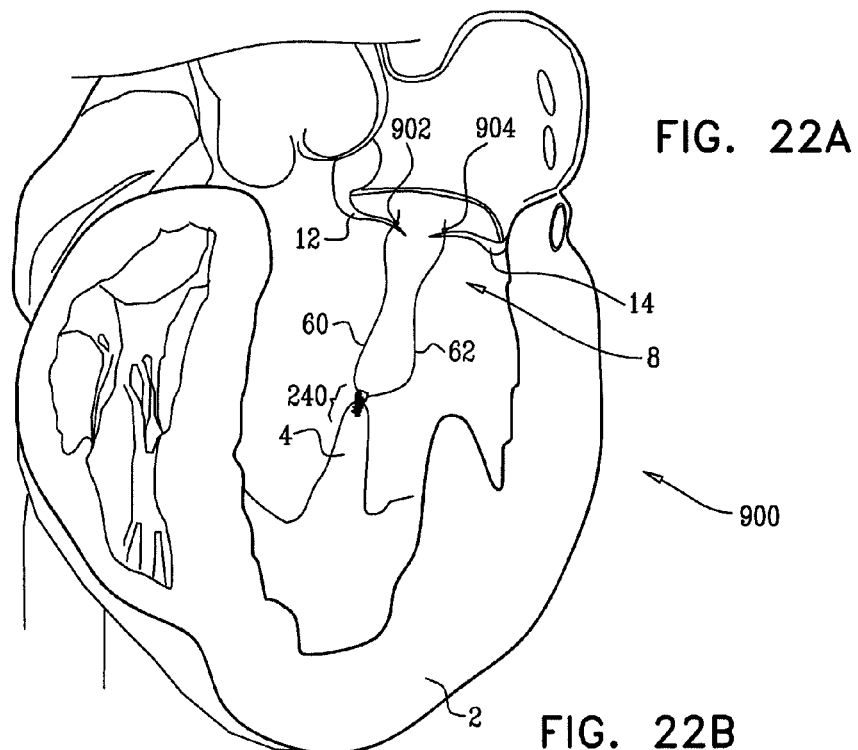
FIGS. 22A-C are schematic illustrations of the repair chords used to draw together leaflets of an atrioventricular valve, in accordance with an embodiment of the present invention.
Figure 22B:
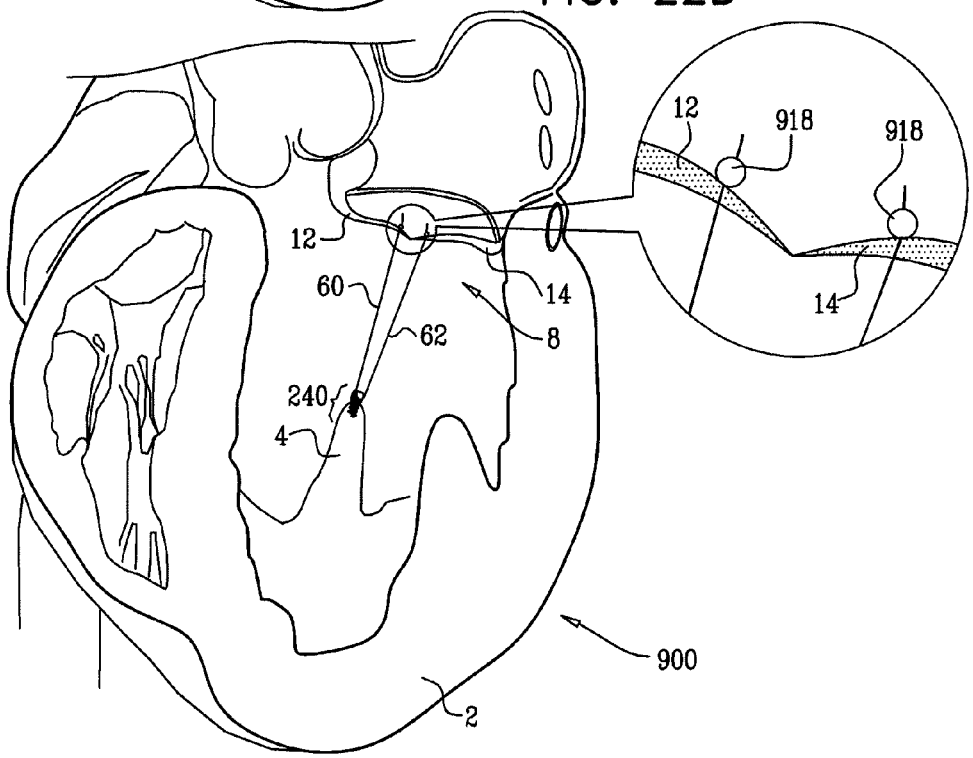
Figure 22C:
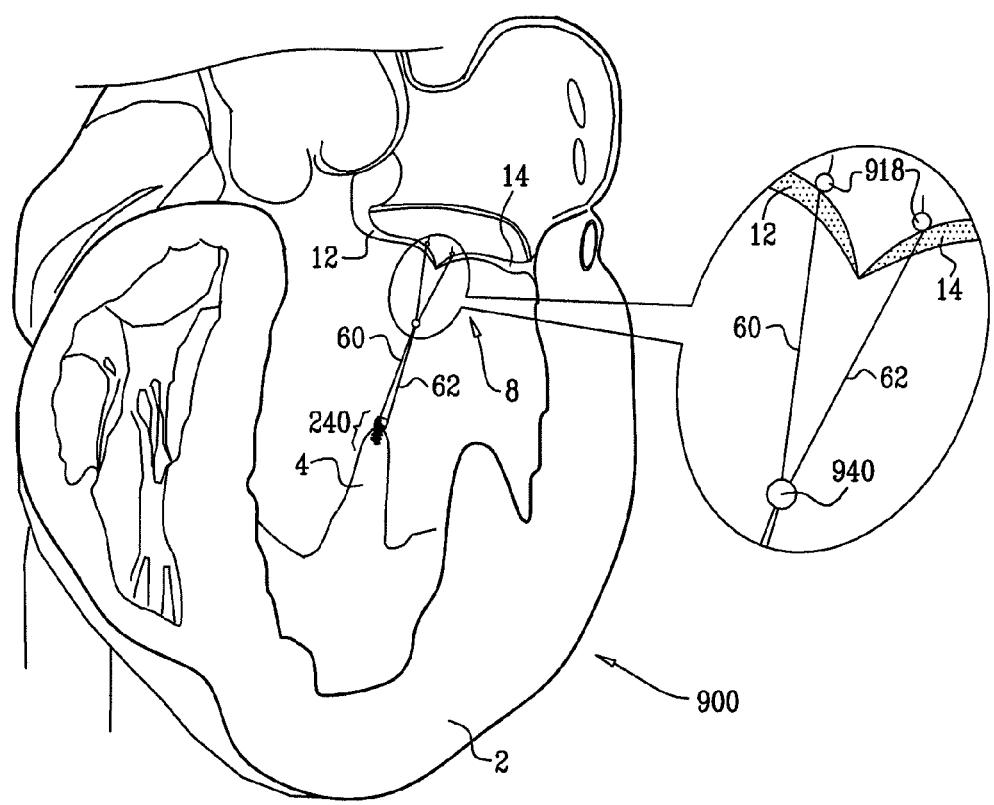

Reference is now made to FIGS. 22A-C which are schematic illustrations of a system 900 for drawing together leaflets 12 and 14 of a mitral valve of the patient, in accordance with an embodiment of the present invention. Spool assembly 240 is implanted in first implantation site 5 at papillary muscle 4 of the left ventricle by way of illustration and not limitation. For example, spool assembly 240 may be implanted in a portion of the heart wall of the ventricle, e.g., the base of the papillary muscle. As described hereinabove, respective first portions of each longitudinal member 60 and 62 are coupled to spool 46 of adjustment mechanism 40. The free end, i.e., second portion, of longitudinal member 60 is coupled, e.g., sutured, anchored, clipped, locked in place with a crimping bead 918, to leaflet 12 at an implantation site 902. The free end, i.e., second portion, of longitudinal member 62 is coupled, e.g., sutured, anchored, clipped, locked in place with a crimping bead 918, to leaflet 14 at an implantation site 904.

As described hereinabove, using tool 20, spool 46 of adjustment mechanism 40 is rotated in order to adjust a length of longitudinal members 60 and 62. As shown in FIG. 22B, longitudinal members 60 and 62 are pulled tight in response to rotation of spool 46 in a first direction thereof. In response to the pulling of longitudinal members 60 and 62 leaflets 12 and 14 are pulled toward one another in order to restore coaptation to valve 8.

It is to be noted that system 900 may be used on the tricuspid valve.

In some embodiments, spool assembly 240 is coupled to first implantation site, e.g., papillary muscle 4, to the base of the papillary muscle, or to any suitable portion of heart tissue facing and surrounding the ventricle. In such an embodiment:

(1) the free end of longitudinal member 60 is coupled to, e.g., sutured to or anchored to, a second implantation site (e.g., another portion of the inner wall of the heart that faces and surrounds the ventricle), (2) the free end of longitudinal member 62 is coupled to, e.g., sutured to or anchored to, a third implantation site (e.g., yet another portion of the inner wall of the heart that opposes the portion of tissue to which the free end of longitudinal member 60 is coupled), and (3) rotation of spool 46 draws the first, second, and third implantation sites toward one another.

In some embodiments, system 900 may be used to provide adjustable artificial chordae tendineae as well as draw together portions of the inner wall of the ventricle, i.e., the portion of the heart tissue which surrounds and faces the ventricular lumen. In such an embodiment, longitudinal member 60 is coupled at a first end thereof to spool 46 and at a second end thereof to a leaflet of the atrioventricular valve. Longitudinal member 62 is coupled at a first end thereof to spool 46 and at a second end thereof to a portion of tissue of the inner wall of the ventricle. As described hereinabove, spool assembly 240 is implanted at first implantation site 5 (e.g., papillary muscle 4, as shown, or any other suitable portion of tissue of the inner wall of the ventricle). In response to rotation of spool 46 of adjustment mechanism, both the leaflet and the portion of tissue of the inner wall of the ventricle are pulled toward spool assembly 240 at implantation site 5.

In the configuration of system 900 shown in FIG. 22C, the implant assembly further comprises at least one bead 940, that is threaded over longitudinal members 60 and 62. The surgeon adjusts the position of the bead along the longitudinal members in order to set the degree to which the free ends of the longitudinal members are free to move with respect to one another. In general, as the bead is positioned closer to the valve, the free ends of the longitudinal members are more constrained in their motion with respect to one another, and the leaflets are drawn closer together. For some applications, the bead comprises a fixation mechanism (e.g., a crimping mechanism), which is configured to fix the bead to the longitudinal members once the bead has been positioned at a desire location along the members.

Reference is now made to FIGS. 23A-I, which are schematic illustrations of yet another system for implanting and adjusting repair chords, and a transcatheter procedure for implanting the chords in a heart, in accordance with an embodiment of the present invention. Except as described hereinbelow, this system and procedure are similar to the system and procedure described hereinabove with reference to FIGS. 9A-K.

Figure 23A:
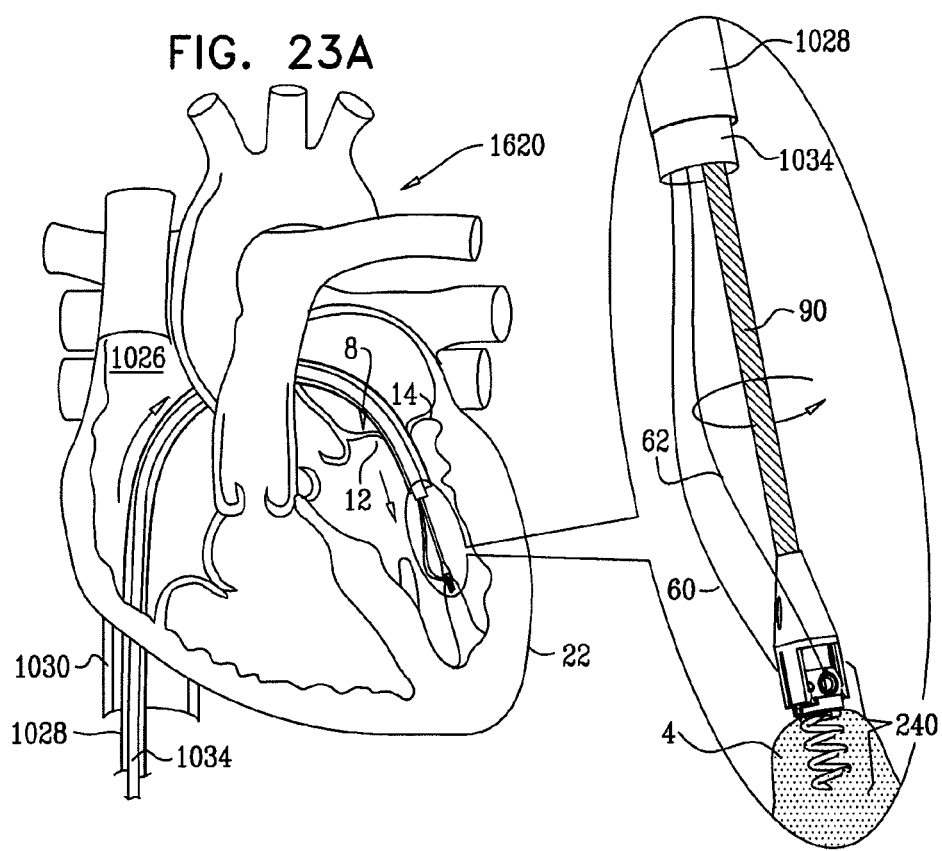
FIGS. 23A-I are schematic illustrations of yet another system for implanting and adjusting repair chords, and a transcatheter procedure for implanting the chords in a heart, in accordance with an embodiment of the present invention.
Figure 23B:
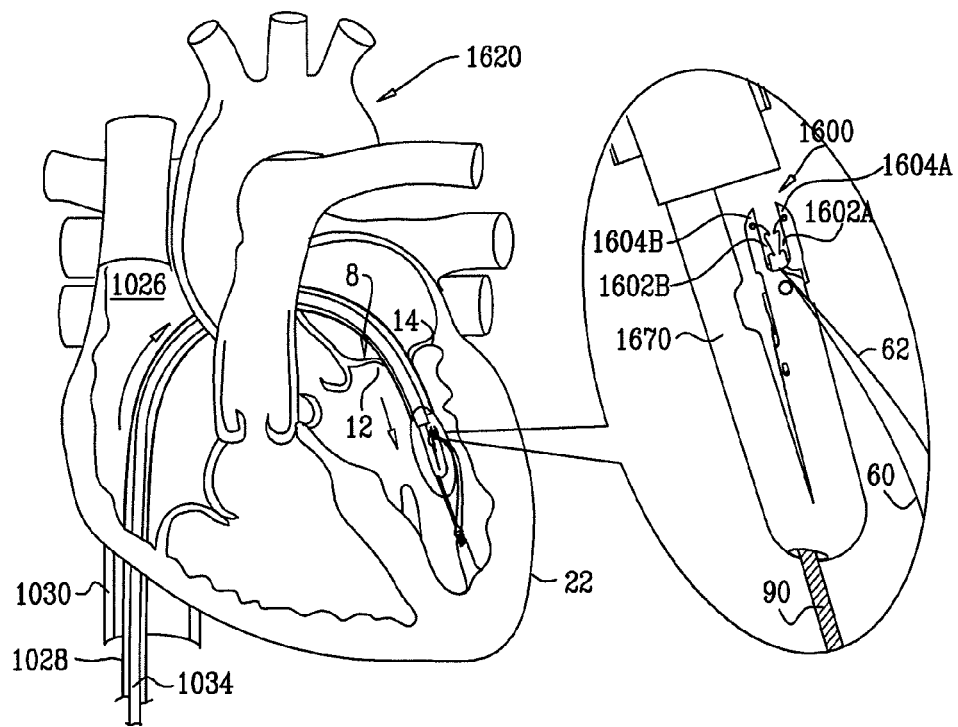
Figure 23C:
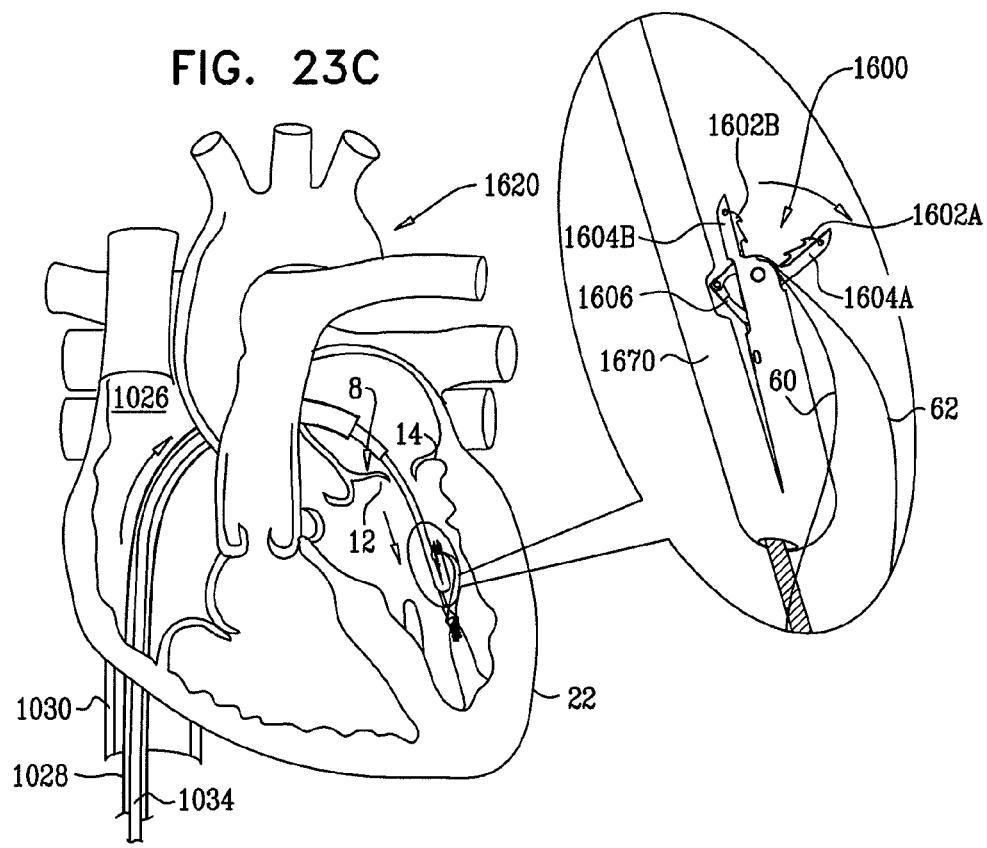

In this embodiment, the one or more leaflet-engaging elements comprise at least one clip 1600 that comprises two clip jaws 1602A and 1602B, which are configured to grasp and engage a leaflet, using one or more anchoring spikes on the clips. A coupling element holder 1670 comprises two tool jaws 1604A and 1604B. Prior to deployment, clip 1600 is held within the tool jaws of the coupling element holder, with clip jaws 1602A and 1602B aligned with and partially covering tool jaws 1604A and 1604B, respectively, as shown in FIGS. 23B and 23C. The tool jaws and clip jaws are shown in a closed position in FIG. 23B. Coupling element holder 1670 is advanced into the left ventricle in this position. Subsequently, as shown in FIG. 23C, the tool jaws are opened, such as by moving tool jaw 1604A using an actuator 1606. Opening of the tool jaws opens the clip jaws.

Figure 23D:
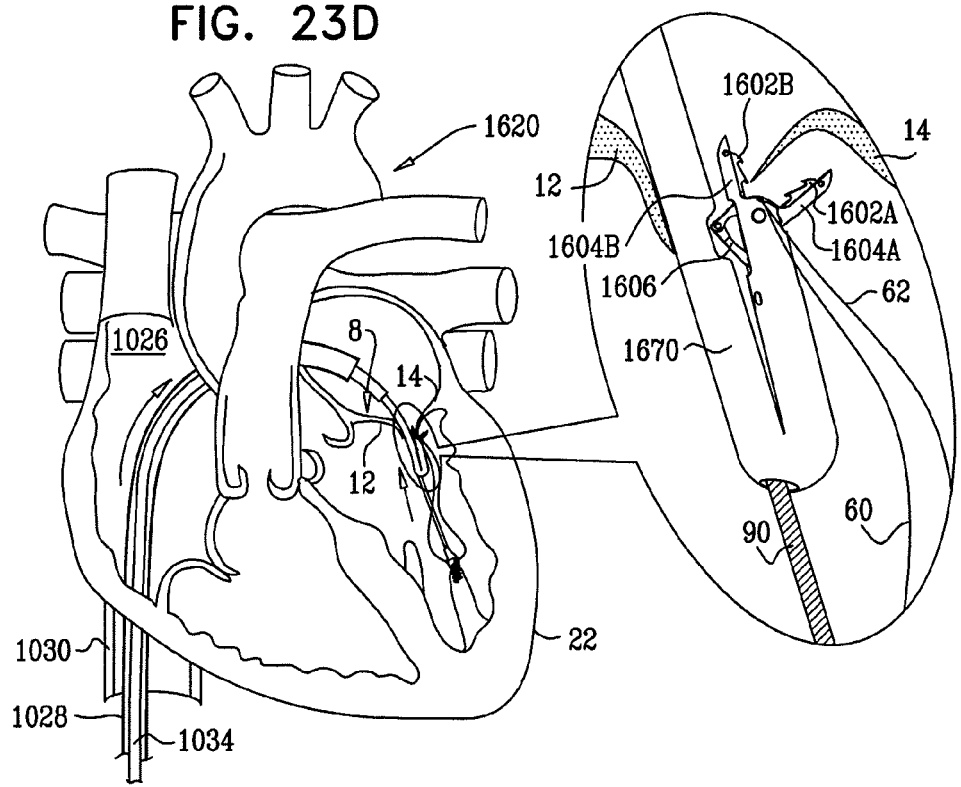
Figure 23E:
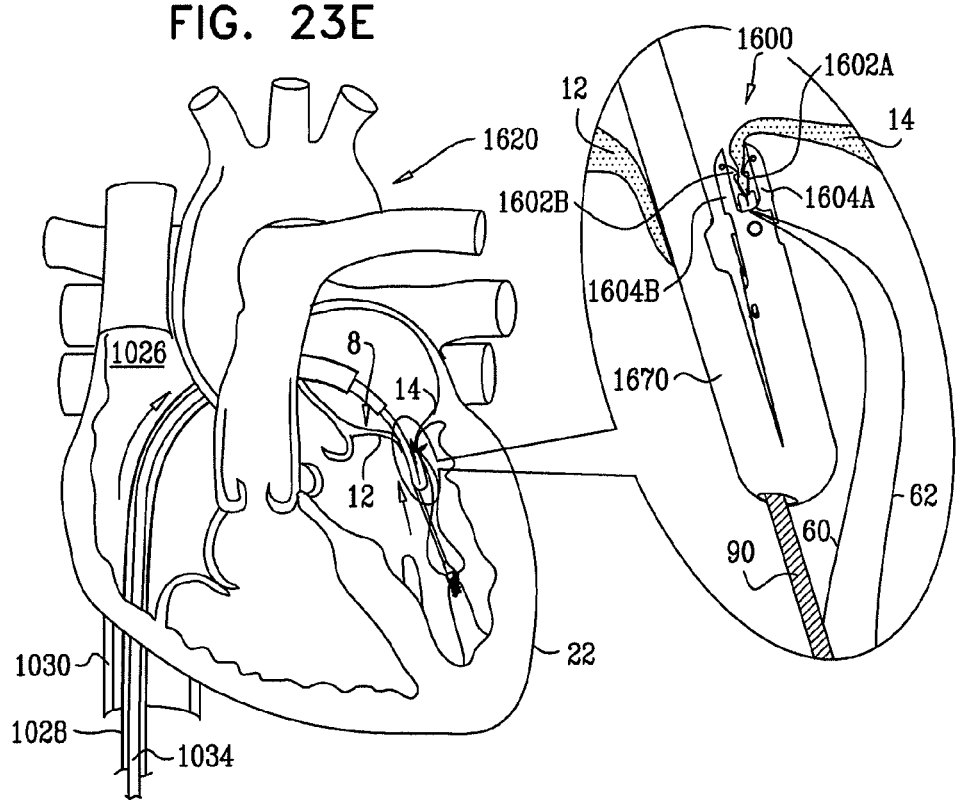

As shown in FIG. 23D, coupling element holder 1670 is withdrawn proximally towards leaflets 12 and 14. The open clip jaws are positioned in a vicinity of one of the leaflets (for example, leaflet 14, as shown in the figure). In order to engage the leaflet with clip 1600, as shown in FIG. 23E, if necessary the surgeon may manipulate the coupling element holder (e.g., to push the clip against the leaflet, and/or slightly withdraw and advance the holder one or more times). Alternatively or additionally, the natural motion of the leaflet may engage the leaflet with the clip. It is noted that before and after this engagement occurs, the leaflets are free to open and close during the natural cardiac cycle. The clip jaws are closed onto the leaflet by closing the tool jaws. Typically, a safety pin 1608 (shown most clearly in FIG. 23I) locks the clip jaws closed.

Figure 23F:
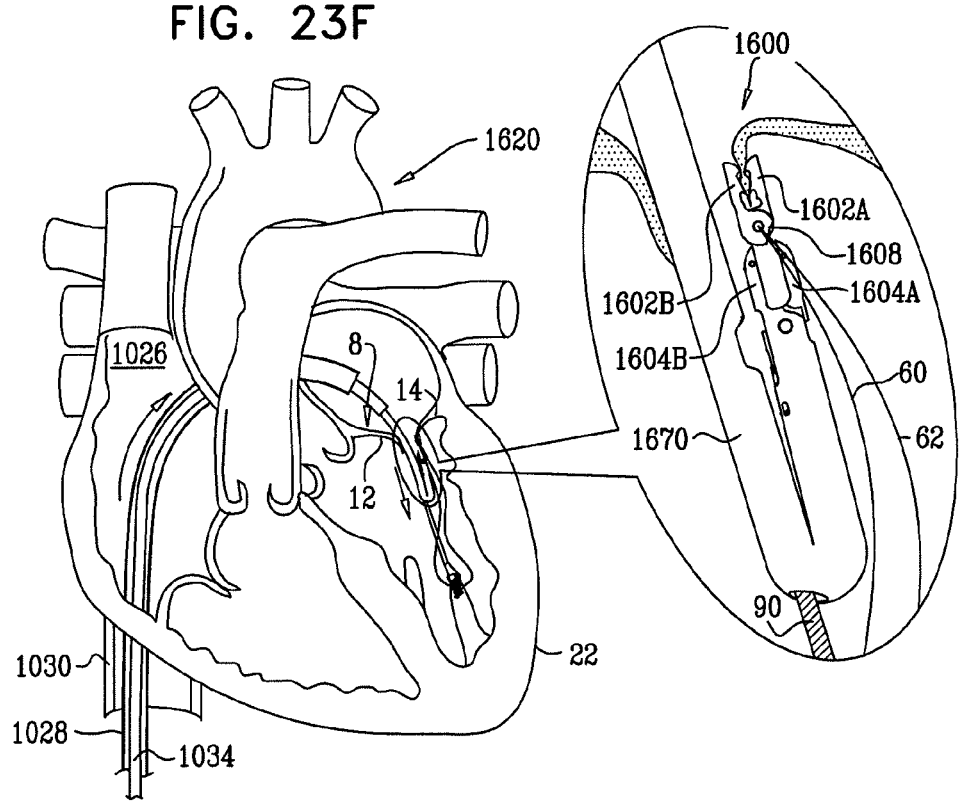
Figure 23G:
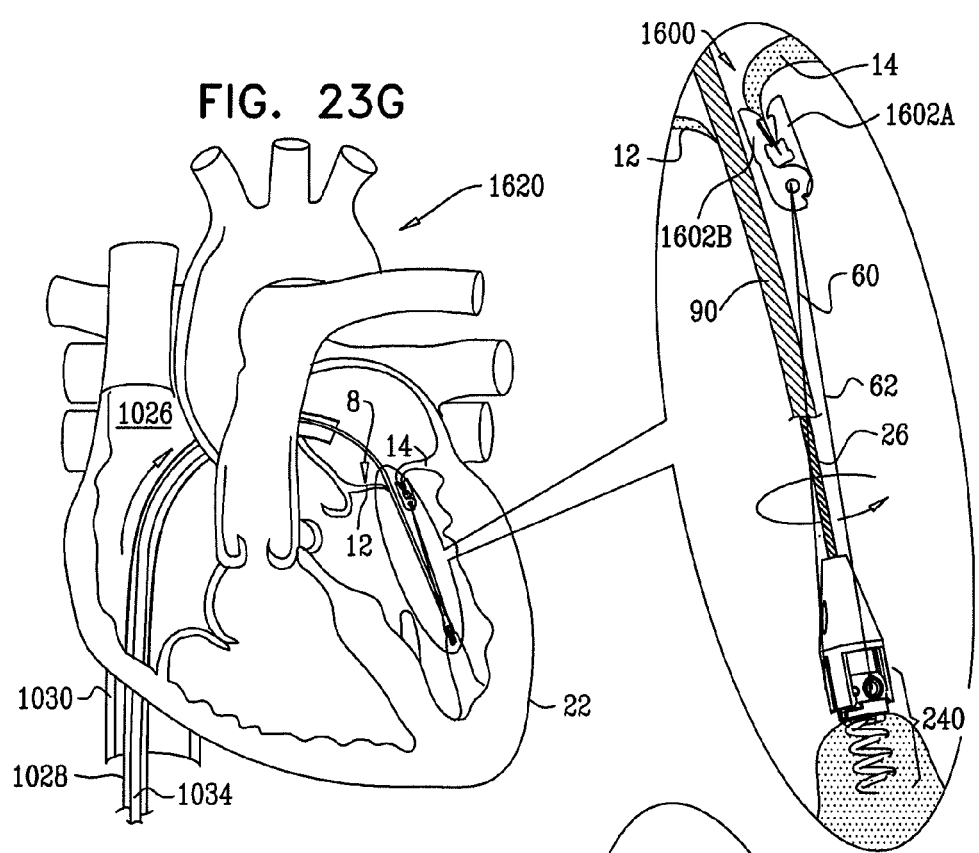
Figure 23H:
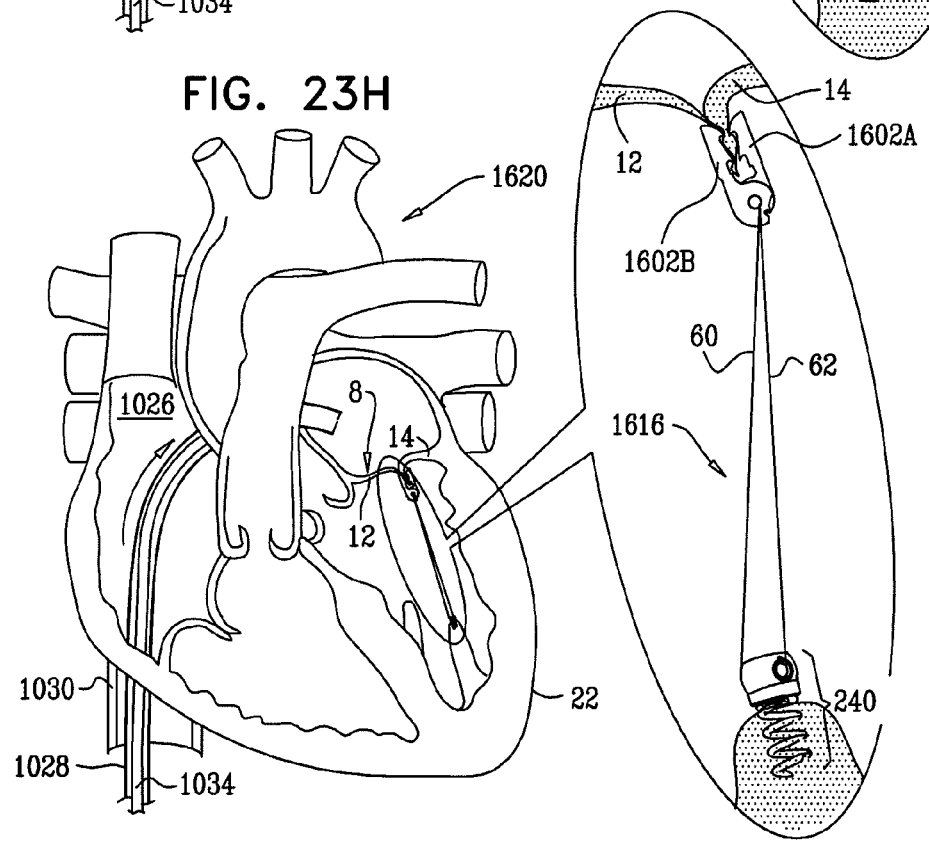
Figure 23I:
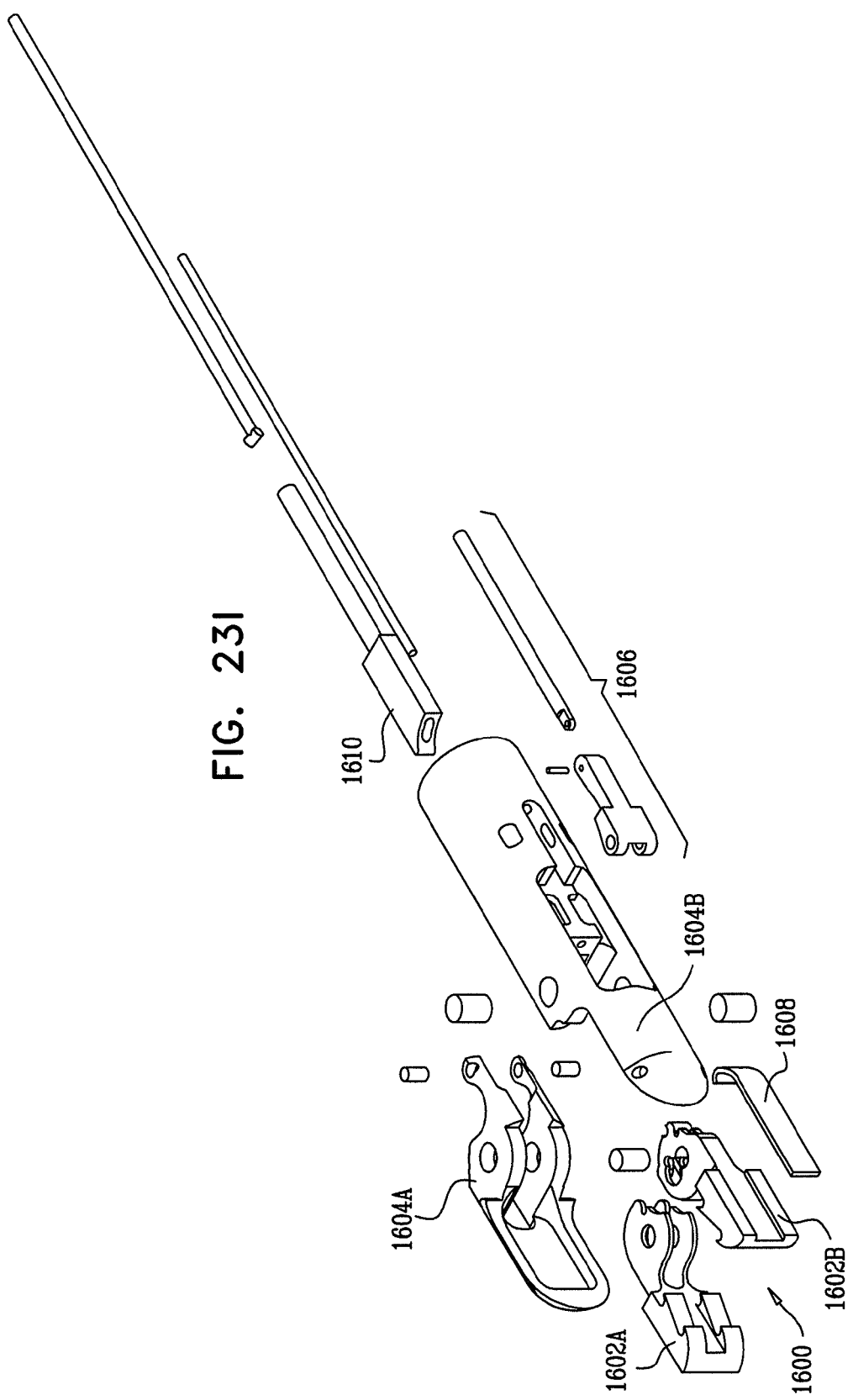

As shown in FIG. 23F, clip 1600 is released from the tool jaws, such as by using an clip release actuator 1610 (shown in FIG. 23I). Coupling element holder 1670 is then withdrawn from the ventricle. As shown in FIG. 23G, torque-delivering tool 26 (within central shaft 90) is rotated to rotate spool 46 of spool assembly 240, thereby wrapping longitudinal members 60 and 62 around spool 46, and shortening the effective length of the longitudinal members, as described hereinabove. Delivery tool 1620 is withdrawn from the heart, leaving implant assembly 1616 implanted in the left ventricle and leaflets, as shown in FIG. 23H.

FIG. 23I is a schematic illustration of the components of clip 1600 and a distal portion of coupling element 1670, in accordance with an application of the present invention. For clarity of illustration, the components are shown disassembled.

Reference is now made to FIGS. 1-23I. It is to be noted that the shortening of longitudinal members 60 and 62 described herein is reversible. That is, rotating spool 46 in a rotational direction that opposes the rotational direction used to shorten the longitudinal members, unwinds respective portions of the longitudinal members from around spool 46. Unwinding the portion of the longitudinal members from around spool 46 thus slackens the remaining portions of the longitudinal members that are disposed between first and second implantation sites 5 and 7. Responsively, the longitudinal members are elongated (i.e., with respect to their shortened states state prior to the unwinding).

Reference is yet again made to FIGS. 1-23I. It is to be noted that following initial adjustment of the repair chords, the repair chords may be further adjusted at a later state following the initial implantation thereof. Using real-time monitoring, tactile feedback and optionally in combination with fluoroscopic imaging, tool 20 may be reintroduced within the heart and engage spool 46.

It is to be noted that systems 10, 400, 500, and 900 may be used as artificial chordae tendineae to replace stretched native chordae tendineae of a left ventricle or of a right ventricle. For some applications, spool assembly 240 is coupled to the papillary muscle. For some applications, spool assembly 240 is coupled to a portion of the wall of the ventricular lumen.

It is to be noted that systems 600, 700, and 800 may be may be used in order to repair malposition of portions of the wall of a left ventricle or of a right ventricle.

Reference is still yet again made to FIGS. 1-23I. It is to be noted that first implantation site 5 may be any portion of tissue that faces and surrounds the ventricle of the heart of the patient. For example, first implantation site 5 may include a first portion of tissue of an inner wall of the ventricle at the base of the papillary muscle or any other suitable location along the inner wall. First implantation site 5 may also include tissue of the papillary muscle. It is to be noted that second implantation site 7 may be any portion of tissue that faces and surrounds the ventricle of the heart of the patient.

For example, second implantation site 7 may include a second portion of tissue of an inner wall of the ventricle at the septum, or any other suitable location along the inner wall. Second implantation site 7 may also include a leaflet of an atrioventricular valve of the heart of the patient.

Reference is still yet again made to FIGS. 1-23I. It is to be noted that systems described herein may be used to repair the heart during open-heart, minimally-invasive, and transcatheter procedures. For embodiments in which delivery tool 20 is introduced within the heart during minimally-invasive and transcatheter procedures, shaft 22, torque-delivering tool 26, and overtube 90 are longer than as shown hereinabove. For such applications, suture needle 64 coupled to the longitudinal member is coupled to needle holder 70 of tool 20 in a manner in which needle 64 faces outward. In such a configuration, the piercing portion, e.g., a barbed portion, of needle 64 is exposed from slit 72 of holder 70. In such an embodiment, needle holder 70 may be coupled to a distal portion of shaft 22.

For transcatheter procedures, delivery tool 20 is advanced toward the heart through an advancement catheter, e.g., a 12-13 F catheter. The advancement catheter facilitates atraumatic advancement of tool 20 through vasculature of the patient by providing an overtube which covers the outwardly-facing needle 64 of tool 20.

The advancement catheter is positioned in the heart in a manner in which a distal end thereof is disposed within the ventricle of the patient and a portion of the advancement catheter extends between the leaflets of the atrioventricular valve of the patient. Tool 20 is advanced through the advancement catheter until a distal end thereof is disposed in the vicinity of first implantation site 5 and subsequently facilitates the implantation of spool assembly 240 in tissue of the ventricle at first implantation site 5. Following the implantation of spool assembly 240 in first implantation site 5, the advancement catheter and multilumen shaft 22 are retracted proximally such that the distal-most ends of the advancement catheter and shaft 22 are disposed proximally to the atrioventricular valve. The advancement catheter is retracted further in order to expose the outwardly-facing needle 64 from within the advancement catheter. Delivery tool 20 is then manipulated, e.g., pushed laterally, such that the piercing portion, e.g., the barbed portion, of needle 64 is disposed adjacently to and punctures a leaflet of the atrioventricular valve. The barbed portion remains disposed coupled to the leaflet, and thereby the second portion of the longitudinal member is coupled to the leaflet.

Spool assembly 240 is then adjusted in a manner as described hereinabove in order to adjust a distance between the second portion of the longitudinal member and spool assembly 240, and thereby create at least one adjustable artificial chorda tendinea that resembles the native chorda tendinea. Following the adjusting of the longitudinal member, delivery tool 20 is decoupled from spool assembly 240, as described hereinabove, and tool 20 and the advancement catheter are extracted from within the body of the patient.

Reference is still yet again made to FIGS. 1-23I. It is to be noted that spool housing 42 and spool 46 may be implanted in a first portion of tissue of the heart independently of tool 20 and tissue anchor 50. In such an embodiment, spool housing 42 is sutured to tissue of the ventricle. Prior to implantation of housing 42, a longitudinal member is coupled to, e.g., knotted to, welded to, looped through, spool 46 at a first portion thereof. The second portion of spool 46 is coupled to, e.g., knotted to, sutured to, or anchored to, a second portion of tissue of the heart. Spool 46 may be rotated using any suitable screwdriver or screwdriver head 95, as described hereinabove.

Reference is still yet again made to FIGS. 1-23I. Spool 46 may be coupled to the heart tissue in a manner in which a central longitudinal axis through spool 46 forms an angle with a surface of the heart tissue of between about 30 and 180 degrees, e.g., between about 75 and 90 degrees, such as about 90 degrees. In some embodiments, spool 46 is coupled to the heart tissue in a manner in which the central longitudinal axis is parallel with the surface of the heart tissue.

Although the techniques described herein are generally described as being performed on the left ventricle and/or mitral valve, the technique may also be performed on the right ventricle and/or tricuspid valve. Additionally, techniques described herein may be used during open-heart, minimally-invasive, and transcatheter procedures, mutatis mutandis.

It is to be noted that the scope of the present invention includes the embodiment of adjusting a length of the artificial chords following initial implantation (i.e., once the delivery tools have been extracted from within the body) in response to the application of energy (e.g., radiofrequency or ultrasound) toward the heart from a source of energy disposed externally to the body of the patient.

For some applications, techniques described herein are practiced in combination with techniques described in one or more of the references cited in the Background section and Cross-references section of the present patent application.

As appropriate, techniques described herein are practiced in conjunction with methods and apparatus described in one or more of the following patent applications, all of which are assigned to the assignee of the present application and are incorporated herein by reference:

PCT Publication WO 06/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed Feb. 16, 2007;

U.S. Provisional Patent Application 61/001,013 to Gross et al., entitled, "Segmented ring placement," filed Oct. 29, 2007;

PCT Patent Application PCT/IL07/001,503 to Gross et al., entitled, "Segmented ring placement," filed Dec. 5, 2007, which published as WO 08/068,756;

U.S. Provisional Patent Application 61/132,295 to Gross et al., entitled, "Annuloplasty devices and methods of delivery therefor," filed Jun. 16, 2008;

U.S. patent application Ser. No. 12/341,960 to Cabiri, entitled, "Adjustable partial annuloplasty ring and mechanism therefor," filed Dec. 22, 2008, which published as US 2010/0161047;

U.S. Provisional Patent Application 61/207,908, to Miller et al., entitled, "Actively-engageable movement-restriction mechanism for use with an annuloplasty structure," filed Feb. 17, 2009;

U.S. patent application Ser. No. 12/435,291 to Maisano et al., entitled, "Adjustable repair chords and spool mechanism therefor," filed May 4, 2009, which published as US 2010/0161041;

U.S. patent application Ser. No. 12/437,103 to Zipory et al., entitled, "Annuloplasty ring with intra-ring anchoring," filed May 7, 2009, which published as US 2010/0286767; and/or PCT Patent Application PCT/IL2009/000593 to Gross et al., entitled, "Annuloplasty devices and methods of delivery therefor," filed Jun. 15, 2009, which published as WO 10/004,546.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. A method, comprising:

positioning, within a lumen of a ventricle of a heart of a patient at an intraventricular site of the ventricle selected from the group consisting of: a papillary muscle and a portion of the inner wall of the ventricle of the patient, a spool coupled to a first end portion of a longitudinal member;

coupling a second end portion of the longitudinal member to a portion of tissue facing the lumen of the ventricle; and rotating the spool, and by the rotating, adjusting a distance between the selected intraventricular site and the portion of tissue facing the lumen of the ventricle.

2. The method according to claim 1, wherein positioning the spool comprises transcatheterally advancing the spool toward the intraventricular site.

3. The method according to claim 1, wherein coupling the second end portion of the longitudinal member to the portion of tissue facing the ventricular lumen comprises coupling the second end portion of the longitudinal member to a leaflet of an atrioventricular valve of the patient.

4. The method according to claim 1, wherein positioning the spool comprises implanting the spool within the lumen of the ventricle at the intraventricular site.

5. The method according to claim 4, wherein implanting the spool within the lumen of the ventricle at the intraventricular site comprises suturing the spool to tissue within the intraventricular site.

6. The method according to claim 4, wherein the spool is coupled to a tissue anchor, and wherein implanting the spool within the lumen of the ventricle at the intraventricular site comprises implanting the tissue anchor in tissue of the ventricle such that a distal end of the tissue anchor is disposed within the tissue of the ventricle and does not extend beyond a pericardium of the heart of the patient.

7. The method according to claim 4, wherein the portion of tissue facing the lumen of the ventricle includes a portion of at least one leaflet of an atrioventricular valve of the patient, wherein the longitudinal member is an artificial chorda tendinea, a first end portion of the artificial chorda tendinea defining the first end portion of the longitudinal member, and wherein the spool is coupled to the first end portion of the artificial chorda tendinea, and wherein implanting the spool comprises:

advancing, between leaflets of the atrioventricular valve and into the ventricle, at least a shaft of a delivery tool, to which shaft the spool is removably coupled, and implanting the spool within the intraventricular site; and while the shaft remains coupled to the spool after implanting the spool, coupling, using a coupling element holder of the delivery tool, at least one leaflet-engaging element to the portion of the at least one leaflet, wherein a second end portion of the artificial chorda tendinea is coupled to the at least one leaflet-engaging element, the second end portion of the artificial chorda tendineae defining the second end portion of the longitudinal member.

8. The method according to claim 7, wherein implanting the spool within the lumen of the ventricle at the intraventricular site comprises implanting the spool at the papillary muscle of the ventricle of the patient.

9. The method according to claim 7, wherein implanting the spool within the lumen of the ventricle at the intraventricular site comprises implanting the spool at the portion of the inner wall of the ventricle of the patient.

10. The method according to claim 7, wherein coupling the at least one leaflet-engaging element to the portion of the at least one leaflet comprises coupling the at least one leaflet-engaging element to exactly one leaflet.

11. The method according to claim 7, wherein coupling the at least one leaflet-engaging element to the portion of the at least one leaflet while the shaft remains coupled to the spool comprises using the shaft to provide a reference force to the leaflet-engaging element.

12. The method according to claim 7, wherein using the coupling element holder of the delivery tool comprises sliding the coupling element holder with respect to the shaft.

13. The method according to claim 7, wherein the at least one leaflet-engaging element is a butterfly clip, which includes a plurality of petals arranged around a needle, and wherein coupling comprises penetrating the needle and petals through a ventricular surface of the at least one leaflet until the needle and petals emerge from an atrial surface of the at least one leaflet, and the petals unfold and couple the clip to the at least one leaflet.

14. The method according to claim 7, further comprising adjusting, from a site outside of a body of the patient, a length of the artificial chorda tendinea.

15. The method according to claim 7, wherein the at least one leaflet-engaging element is a clip, and wherein coupling comprises clamping the clip on the at least one leaflet such that the clip engages atrial and ventricular surfaces of the leaflet.

16. The method according to claim 15, wherein the clip includes two clip jaws, and wherein clamping comprises holding the clip jaws within respective tool jaws of the coupling element holder, and opening and closing the clip jaws using the tool jaws.

17. The method according to claim 7, wherein the at least one leaflet-engaging element is a non-continuous ring, and wherein coupling comprises coupling the non-continuous ring to the at least one leaflet.

18. The method according to claim 17, wherein coupling the non-continuous ring to the at least one leaflet comprises initially holding the non-continuous ring in an extended position using a deforming rod, positioning the non-continuous ring in a vicinity of the at least one leaflet, and thereafter separating the deforming rod from the non-continuous ring such that the non-continuous ring assumes an annular position coupled to the at least one leaflet.

19. The method according to claim 7, wherein the at least one leaflet-engaging element is at least one hook, and wherein coupling comprises puncturing the at least one leaflet with the at least one hook.

20. The method according to claim 19, wherein puncturing the at least one leaflet with the at least one hook comprises sliding the at least one hook proximally to an atrial surface of the at least one leaflet and subsequently puncturing the leaflet by sliding the at least one hook distally.

21. The method according to claim 19, wherein puncturing the at least one leaflet comprises sliding the at least one hook proximally to an atrial surface of the leaflet and allowing the at least one leaflet to engage the at least one hook responsively to beating of the leaflet.

22. The method according to claim 1,
wherein adjusting the distance comprises:
by the rotating of the spool, winding a portion of the longitudinal member around the spool,
by the winding of the portion, shortening a length of the longitudinal member, and
by the shortening of the length of the longitudinal member, drawing together the selected intraventricular site and the portion of tissue facing the lumen of the ventricle.

23. The method according to claim 22, wherein adjusting comprises adjusting, from a site outside of a body of the patient, the length of the longitudinal member.

24. The method according to claim 22,
wherein positioning the spool within the lumen of the ventricle of the heart of the patient at the intraventricular site comprises implanting the spool at a first portion of the inner wall of the ventricle of the patient,
wherein coupling the second end portion of the longitudinal member to the portion of tissue comprises coupling the second end portion of the longitudinal member to a second portion of the inner wall of the ventricle of the patient, and
wherein drawing together the selected intraventricular site and the portion of tissue facing the lumen of the ventricle comprises drawing the first and second portions of tissue of the inner wall of the ventricle toward one another.

25. The method according to claim 22, wherein the longitudinal member defines a first longitudinal member, wherein positioning the spool coupled to the first end portion of the longitudinal member comprises positioning a spool coupled to at least the first longitudinal member and to at least a second longitudinal member at respective first end portions thereof, each longitudinal member having respective second end portions thereof, wherein coupling the second end portion of the longitudinal member to the portion of tissue facing the lumen of the ventricle comprises coupling the second end portion of the first longitudinal member to a first portion of heart tissue facing the ventricular lumen, and wherein the method further comprises:
coupling the second end portion of the second longitudinal member to a second portion of heart tissue facing the ventricular lumen; and
drawing the first and second portions of heart tissue toward one another.

26. The method according to claim 1, further comprising advancing the spool toward the intraventricular site by advancing a portion of a delivery tool that is reversibly coupled to the spool between leaflets of an atrioventricular valve having at least first and second leaflets thereof, and wherein positioning the spool within the lumen of the ventricle at the intraventricular site comprises manipulating the delivery tool to position the spool within the lumen of the ventricle at the intraventricular site.

27. The method according to claim 26, further comprising, after positioning the spool:
decoupling the delivery tool from the spool,
removing the delivery tool from the ventricle, and
subsequently to the removing, accessing the spool at the intraventricular site.

28. The method according to claim 27, wherein accessing the spool comprises recoupling the delivery tool to the spool by advancing the delivery tool along at least one guide wire coupled to the spool.

29. The method according to claim 27, wherein accessing the spool comprises coupling a torque-delivering tool to the spool by advancing the torque-delivering tool through an elongate tube coupled at a first end thereof to the spool and at a second end thereof configured to be coupled to a portion of subcutaneous tissue of the patient.

30. The method according to claim 26, further comprising, after coupling the second end portion of the longitudinal member to the portion of tissue facing the ventricular lumen:
sliding a shaft of the delivery tool with respect to a torque-delivering tool of the delivery tool, and sliding a proximal portion of the shaft into a lumen of a handle portion of the delivery tool; and
subsequently to the sliding, rotating the spool.

31. The method according to claim 30, wherein sliding the shaft comprises:
sliding the shaft until a distal portion of the shaft is disposed proximally to the atrioventricular valve, and
responsively, reducing a diameter of the portion of the delivery tool disposed between the leaflets of the valve.

32. The method according to claim 31, wherein reducing the diameter of the portion of the delivery tool disposed between the leaflets of the valve comprises reducing the diameter to between 0.8 mm and 1.5 mm.

33. The method according to claim 1,
wherein positioning the spool comprises positioning the spool coupled to a mechanical locking element having a surface coupled to a lower surface of the spool, and
wherein the method further comprises:
advancing an elongate tool through a channel provided by the spool;
unlocking the spool from the mechanical locking element by pushing a depressible portion of the surface of the locking element;
responsively to the pushing of the depressible portion, dislodging a protrusion protruding out of a plane of the surface of the mechanical element from within a recess defined by the spool; and
rotating the spool.

34. The method according to claim 33,
wherein, during a first period:
pushing the depressible portion comprises maintaining the protrusion in a position in which it is dislodged from the recess; and
rotating the spool;
wherein the method further comprises, during a second period:
removing the elongate tool from within the channel and facilitating positioning of the protrusion in the recess; and
restricting rotation of the spool.

* * * * *